United States Patent
Normington et al.

(10) Patent No.: US 9,919,003 B2
(45) Date of Patent: Mar. 20, 2018

(54) NICOTINAMIDE MONONUCLEOTIDE DERIVATIVES AND THEIR USES

(71) Applicant: Metro International Biotech, LLC, Birmingham, MI (US)

(72) Inventors: Karl D. Normington, Prides Crossing, MA (US); David A. Sinclair, Chestnut Hill, MA (US); David J. Livingston, Barrington, RI (US); James M. McKearin, Litchfield, NH (US); Bruce Szczpankiewicz, Hopkinton, MA (US); Jonathan N. Kremsky, Arlington, MA (US)

(73) Assignee: Metro International Biotech, LLC, Birmingham, MI (US)

( * ) Notice: Subject to any disclaimer, the term of this patent is extended or adjusted under 35 U.S.C. 154(b) by 0 days.

(21) Appl. No.: 15/463,683

(22) Filed: Mar. 20, 2017

(65) Prior Publication Data

US 2017/0189434 A1 Jul. 6, 2017

Related U.S. Application Data

(62) Division of application No. 15/512,388, filed as application No. PCT/US2016/045855 on Aug. 5, 2016.

(60) Provisional application No. 62/201,447, filed on Aug. 5, 2015.

(51) Int. Cl.
*A01N 43/04* (2006.01)
*A61K 31/70* (2006.01)
*A61K 31/706* (2006.01)
*C07H 19/048* (2006.01)
*C07H 19/04* (2006.01)
*A61K 31/7052* (2006.01)

(52) U.S. Cl.
CPC ........ *A61K 31/706* (2013.01); *A61K 31/7052* (2013.01); *C07H 19/04* (2013.01); *C07H 19/048* (2013.01)

(58) Field of Classification Search
None
See application file for complete search history.

(56) References Cited

U.S. PATENT DOCUMENTS

2012/0328526 A1 12/2012 Kristian

FOREIGN PATENT DOCUMENTS

| CN | 101497638 A | 8/2009 |
| WO | WO-2017/079195 A1 | 5/2017 |

OTHER PUBLICATIONS

Rodionova et al. 2014. Metabolic and bactericidal effects of targeted suppression of NadD and NadE enzymes in mycobacteria. mBio 5(1):e00747-13. doi:10.1128/mBio.00747-13.*
Stein et al. The Journal of Neuroscience (2014), vol. 34(17), pp. 5800-5815.*
Database Registry Chemical Abstracts, Database Accession No. 807266-77-9, CAS Registry No. 807266-77-9 (Jan. 2, 2005).
International Search Report and Written Opinion for International Application No. PCT/US2016/045855 dated Nov. 14, 2016.
Yoshino et al., "Nicotinamide Mononucleotide, a Key NAD+ Intermediate, Treats the Pathology of Diet- and Age-Induced Diabetes in Mice," Cell Metab, 14(4): 528-536 (2011).
Yang et al., "NAD+-dependent Deacetylase SIRT3 Regulates Mitochondrial Protein Synthesis by Deacetylation of the Ribosomal Protein MRPL10," J Biol Chem, 285: 7417-7429 (2010).

* cited by examiner

*Primary Examiner* — Patrick T Lewis
(74) *Attorney, Agent, or Firm* — David P. Halstead; Foley Hoag LLP

(57) ABSTRACT

The invention relates to compositions of nicotinamide mononucleotide derivatives and their methods of use. The invention also relates to methods of preparing nicotinamide mononucleotide derivatives. The invention relates to pharmaceutical compositions and nutritional supplements containing a nicotinamide mononucleotide derivative. The invention relates to methods of using nicotinamide mononucleotide derivatives that promote the increase of intracellular levels of nicotinamide adenine dinucleotide (NAD+) in cells and tissues for treating diseases and improving cell and tissue survival.

37 Claims, No Drawings

NICOTINAMIDE MONONUCLEOTIDE DERIVATIVES AND THEIR USES

RELATED APPLICATIONS

This application is a divisional of U.S. patent application Ser. No. 15/512,388, which is the U.S. national phase of International Patent Application No. PCT/US2016/045855, filed Aug. 5, 2016, which claims the benefit of priority of U.S. Patent Application Ser. No. 62/201,447, filed Aug. 5, 2015, the contents of which are hereby incorporated by reference in their entirety.

BACKGROUND OF THE INVENTION

Nicotinamide adenine dinucleotide (NAD) and its derivative compounds are known as essential coenzymes in cellular redox reactions in all living organisms. Several lines of evidence have also shown that NAD participates in a number of important signaling pathways in mammalian cells, including poly(ADP-ribosyl)ation in DNA repair (Menissier de Murcia et al., EMBO J., (2003) 22, 2255-2263), mono-ADP-ribosylation in the immune response and G protein-coupled signaling (Corda and Di Girolamo, EMBO J., (2003) 22, 1953-8), and the synthesis of cyclic ADP-ribose and nicotinate adenine dinucleotide phosphate (NAADP) in intracellular calcium signaling (Lee, Annu. Rev. Pharmacol. Toxicol., (2001) 41, 317-345). Recently, it has also been shown that NAD and its derivatives play an important role in transcriptional regulation (Lin and Guarente, Curr. Opin. Cell. Biol., (2003) 15, 241-246). In particular, the discovery of Sir2 NAD-dependent deacetylase activity (e.g., Imai et al., Nature, (2000) 403, 795-800; Landry et al., Biochem. Biophys. Res. Commun., (2000) 278, 685-690; Smith et al., Proc. Natl. Acad. Sci. USA, (2000) 97, 6658-6663) drew attention to this new role of NAD.

The Sir2 family of proteins consumes NAD for its deacetylase activity and regulates transcription by deacetylating histones and a number of other transcription regulators.

Because of this absolute requirement for NAD, it has been proposed that Sir2 proteins function as energy sensors that convert the energy status of cells to the transcriptional regulatory status of genes (Imai et al., Nature, (2000) 403, 795-800; Imai et al., Cold Spring Harbor Symp. Quant. Biol., (2000) 65, 297-302). Sir2 proteins produce nicotinamide and O-acetyl-ADP-ribose in addition to the deacetylated protein substrates in their deacetylation reaction (Moazed, Curr. Opin. Cell. Biol., (2001) 13, 232-238; Denu, Trends Biochem. Sci., (2003) 28, 41-48; see also FIG. 1), and nicotinamide is eventually recycled into NAD biosynthesis. Unlike other NAD-dependent biochemical reactions, the NAD-dependent deacetylase activity of the Sir2 family of proteins is generally highly conserved from bacteria to mammals (Frye, Biochem. Biophys. Res. Commun., (2000) 273, 793-798), suggesting that the connection between NAD and Sir2 proteins is ancient and fundamental. In mammals, the Sir2 ortholog, Sirt1/Sir2α, has been shown to regulate metabolism in response to nutrient availability (Bordone and Guarente, Nat. Rev. Mol. Cell Biol., (2005) 6, 298-305). In adipocytes, Sirt1 triggers lipolysis and promotes free fatty acid mobilization by repressing PPAR-gamma, a nuclear receptor that promotes adipogenesis (Picard et al., Nature, (2004) 429, 771-776). In hepatocytes, Sirt1 regulates the gluconeogenic and glycolytic pathways in response to fasting by interacting with and deacetylating PGC-la, a key transcriptional regulator of glucose production in the liver (Rodgers et al., Nature, (2005) 434, 113-118). Additionally, Sirt1 promotes insulin secretion in pancreatic beta cells in response to high glucose partly by repressing Ucp2 expression and increasing cellular ATP levels (Moynihan et al., Cell Metab., (2005) 2, 105-117). While little is known about the regulation of NAD biosynthesis in mammals, NAD biosynthesis may play a role in the regulation of metabolic responses by altering the activity of certain NAD-dependent enzymes such as Sirt1 in a variety of organs and/or tissues.

The NAD biosynthesis pathways have been characterized in prokaryotes by using *Escherichia coli* and *Salmonella typhimurium* (Penfound and Foster, Biosynthesis and recycling of NAD, in *Escherichia coli* and *Salmonella*: Cellular and Molecular Biology, p. 721-730, ed. Neidhardt, F. C., 1996, ASM Press: Washington, D.C.) and recently in yeast (Lin and Guarente, Curr. Opin. Cell. Biol., (2003) 15, 241-246; Denu, Trends Biochem. Sci., (2003) 28, 41-48). In prokaryotes and lower eukaryotes, NAD is synthesized by the de novo pathway via quinolinic acid and by the salvage pathway via nicotinic acid (Penfound and Foster, id.) In yeast, the de novo pathway begins with tryptophan, which is converted to nicotinic acid mononucleotide (NaMN) through six enzymatic steps and one non-enzymatic reaction (Lin and Guarente, Curr. Opin. Cell. Biol., (2003) 15, 241-246). Two genes, BNA1 and QPT1, have been characterized in this pathway in yeast. At the step of NaMN synthesis, the de novo pathway converges with the salvage pathway. The salvage pathway begins with the breakdown of NAD into nicotinamide and O-acetyl-ADP-ribose, which is mainly catalyzed by the Sir2 proteins in yeast. Nicotinamide is then deamidated to nicotinic acid by a nicotinamidase encoded by the PNC1 gene. Nicotinic acid phosphoribosyltransferase (Npt), encoded by the NPT1 gene, converts nicotinic acid to NaMN, which is eventually converted to NAD through the sequential reactions of nicotinamide/nicotinic acid mononucleotide adenylyltransferase (encoded by NMA1 and/or NMA2) and NAD synthetase (encoded by QNS1).

Many aspects of mammalian behavior and physiology are coordinated through interconnected networks of 24-hour central and peripheral oscillators that synchronize cycles of fuel storage and utilization to maintain organismal homeostasis. In mice, circadian disruption has been tied to metabolic disturbance (F. W. Turek et al., Science 308, 1043 (2005); R. D. Rudic et al., PLoS Biol. 2, e377 (2004)), while conversely, high-fat diet alters both behavioral and molecular rhythms (A. Kohsaka et al., Cell Metab. 6, 414 (2007); M. Barnea, Z. Madar, O. Froy, Endocrinology 150, 161 (2009)). The underlying mechanism of the mammalian clock consists of a transcription-translation feedback loop in which CLOCK and BMAL1 activate transcription of Cryptochrome (Cry1 and 2) and Period (Per1, 2, and 3), leading to subsequent repression of CLOCK:BMAL1 by CRY and PER proteins (J. S. Takahashi, H. K. Hong, C. H. Ko, E. L. McDearmon, Nat. Rev. Genet. 9, 764 (2008)). An additional feedback loop involves the transcriptional regulation of Bmal1 by ROR☐ and REV-ERB☐ (N. Preitner et al., Cell 110, 251 (2002); T. K. Sato et al., Neuron 43, 527 (2004)). Previous studies have also implicated a role for cellular NAD+ in the regulation of CLOCK and NPAS2 activity (J. Rutter, M. Reick, L. C. Wu, S. L. McKnight, Science 293, 510 (2001)), an observation consistent with the recent finding that the NAD+-dependent protein deacetylase SIRT1 modulates activity of the clock complex (Y. Nakahata et al., Cell 134, 329 (2008); G. Asher et al., Cell 134, 317 (2008)).

U.S. Pat. No. 8,106,184 describes methods of manufacturing and using nicotinoyl riboside compositions.

U.S. application Ser. No. 11/396,359 describes nicotinamide riboside analogues and their uses.

U.S. application Ser. No. 11/053,185 describes methods and compositions for modulating the life span of eukaryotic and prokaryotic cells and for protecting cells against certain stresses, including modulating the flux of the NAD+ salvage pathway in the cell.

There remains a need for improved compositions and methods of using such compositions for pharmacologic intervention and/or manipulation of the NAD pathway in mammalian cells and tissues.

SUMMARY OF THE INVENTION

The invention relates to compositions of nicotinamide mononucleotide derivatives and their methods of use. In some embodiments, the invention relates to methods of making nicotinamide mononucleotide derivatives. In some embodiments, the invention relates to pharmaceutical compositions and nutritional supplements containing one or more nicotinamide mononucleotide derivatives. In further embodiments, the invention relates to methods of using nicotinamide mononucleotide derivatives that promote the increase of intracellular levels of nicotinamide adenine dinucleotide (NAD+) in cells and tissues for treating diseases and improving cell and tissue survival.

DETAILED DESCRIPTION OF THE INVENTION

The advantages of the present invention include, without limitation, compounds and compositions of nicotinamide mononucleotide derivatives and their methods of use. In some embodiments, the invention relates to methods of making nicotinamide mononucleotide derivatives. In some embodiments, the invention relates to pharmaceutical compositions and nutritional supplements containing one or more nicotinamide mononucleotide derivatives. In further embodiments, the invention relates to methods of using nicotinamide mononucleotide derivatives that promote the increase of intracellular levels of nicotinamide adenine dinucleotide (NAD+) in cells and tissues for treating diseases and improving cell and tissue survival.

Compounds, Compositions and Methods of Treatment

Provided herein are compounds, and their stereoisomers, salts, hydrates, solvates, and crystalline forms thereof, wherein the compound has a structure represented by formula II:

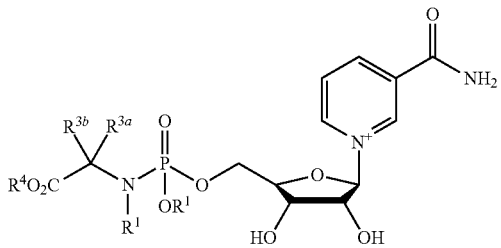

II wherein
(a) $R^1$ is hydrogen; n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, $-N(R^{1'})_2$, $C_{1-6}$ acylamino, $-NHSO_2C_{1-6}$ alkyl, $-SO_2N(R^{1'})_2$, $COR^{1''}$, and $-SO_2C_{1-6}$ alkyl;
$R^{1'}$ is independently hydrogen or alkyl, which includes, but is not limited to, $C_{1-20}$ alkyl, $C_{1-10}$ alkyl, or $C_{1-6}$ alkyl; and
$R^{1''}$ is $-OR'$ or $-N(R^{1'})_2$;

(b) $R^2$ is hydrogen; $C_{1-10}$ alkyl; or $-C(O)CR^{3a}R^{3b}NHR^1$, where n is 2 to 4; or
$R^{3a}$; $R^{3b}$ and $R^2$ together are $(CH_2)_n$ forming a cyclic ring that includes the adjoining N and C atoms;

(c) $R^{3a}$ and $R^{3b}$ are
  (i) independently selected from hydrogen, $C_{1-10}$ alkyl, cycloalkyl, $-(CH_2)_c(NR^{3'})_2$, $C_{1-6}$ hydroxyalkyl, $-CH_2SH$, $-(CH_2)_2S(O)_dMe$, $-(CH_2)_3NHC(=NH)NH_2$, (1H-indol-3-yl)methyl, (1H-imidazol-4-yl)methyl, $-(CH_2)_eCOR^{3''}$, aryl and aryl $C_{1-3}$ alkyl, said aryl groups are optionally substituted with a group selected from hydroxyl, $C_{1-10}$ alkyl, $C_{1-6}$ alkoxy, halogen, nitro and cyano; or
  (ii) $R^{3a}$ and $R^{3b}$ both are $C_{1-6}$ alkyl; or
  (iii) $R^{3a}$ and $R^{3b}$ together are $(CH_2)_f$ so as to form a spiro ring; or
  (iv) $R^{3a}$ is hydrogen and $R^{3b}$ and $R^2$ together are $(CH_2)_n$ so as to form a cyclic ring that includes the adjoining N and C atoms; or
  (v) $R^{3b}$ is hydrogen and $R^{3a}$ and $R^2$ together are $(CH_2)_n$ so as to form a cyclic ring that includes the adjoining N and C atoms; or
  (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or
  (viii) $R^{3a}$ is $CH_3$, $-CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, and $R^{3''}$ is $-OR'$ or $-N(R^{3'})_2$);

c is from 1 to 6,
d is from 0 to 2,
e is from 0 to 3,
f is from 2 to 5,
n is from 2 to 4, and (d) $R^4$ is hydrogen; $C_{1-10}$ alkyl optionally substituted with a lower alkyl, alkoxy, di(lower alkyl)-amino, or halogen; $C_{1-10}$ haloalkyl; $C_{3-10}$ cycloalkyl; cycloalkyl alkyl; cycloheteroalkyl; aminoacyl; aryl, such as phenyl; or heteroaryl, such as, pyridinyl; substituted aryl; or substituted heteroaryl.

In certain embodiments, provided herein are compounds of formula II, and stereoisomers, salts, and crystalline forms thereof.

Provided herein are compounds, and their stereoisomers, salts, hydrates, solvates, and crystalline forms thereof, wherein the compound is selected from

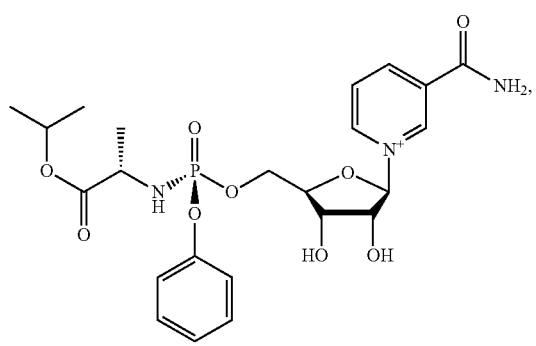

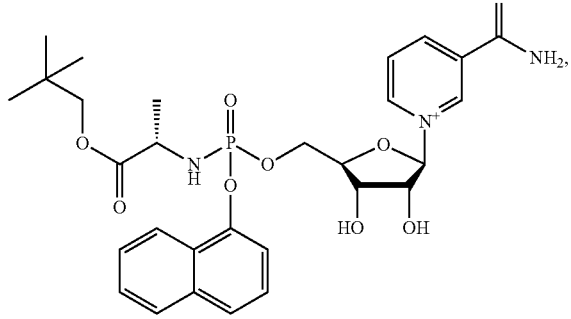

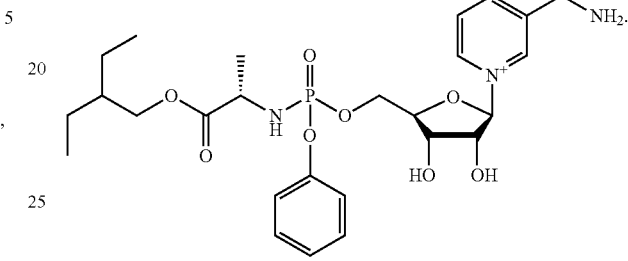

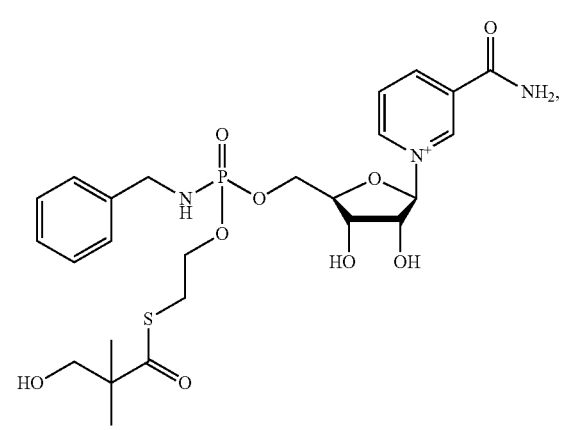

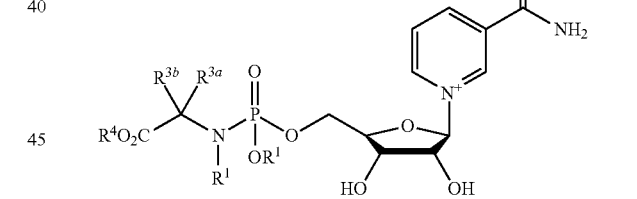

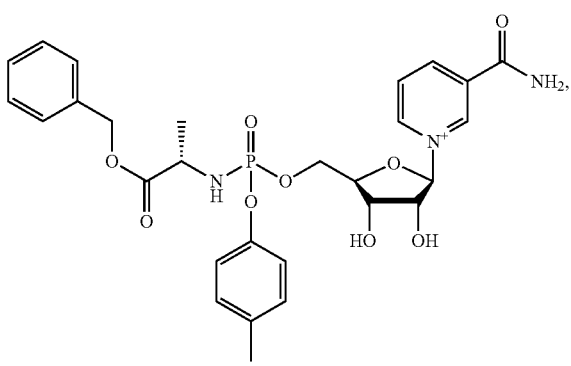

Provided herein are compositions for the treatment and/or prophylaxis of any of the diseases disclosed herein, comprising a pharmaceutically acceptable medium selected from an excipient, carrier, diluent, and equivalent medium, and a compound, or a stereoisomer, salt, hydrate, solvate, or crystalline form thereof, wherein the compound has a structure represented by formula II:

wherein
(a) $R^1$ is hydrogen; n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, $-N(R^{1'})_2$, $C_{1-6}$ acylamino, $-NHSO_2C_{1-6}$ alkyl, $-SO_2N(R^{1'})_2$, $COR^{1''}$, and $-SO_2C_{1-6}$ alkyl;
$R^{1'}$ is independently hydrogen or alkyl, which includes, but is not limited to, $C_{1-20}$ alkyl, $C_{1-10}$ alkyl, or $C_{1-6}$ alkyl; and
$R^{1''}$ is $-OR'$ or $-N(R^{1'})_2$;
(b) $R^2$ is hydrogen; $C_{1-10}$ alkyl; or $-C(O)CR^{3a}R^{3b}NHR^1$, where n is 2 to 4; or
$R^{3a}$; $R^{3b}$ and $R^2$ together are $(CH_2)_n$ forming a cyclic ring that includes the adjoining N and C atoms;
(c) $R^{3a}$ and $R^{3b}$ are
(i) independently selected from hydrogen, $C_{1-10}$ alkyl, cycloalkyl, $-(CH_2)(NR^{3'})_2$, $C_{1-6}$ hydroxyalkyl, —CH₂SH, —(CH₂)₂S(O)$_d$Me, —(CH₂)₃NHC(=NH)NH₂, (1H-indol-3-yl)methyl, (1H-imidazol-4-yl)methyl, —(CH₂)$_e$COR³''', aryl and aryl C₁₋₃ alkyl, said aryl groups are optionally substituted with a group selected from hydroxyl, C₁₋₁₀ alkyl, C₁₋₆ alkoxy, halogen, nitro and cyano; or (ii) R³$^a$ and R³$^b$ both are C₁₋₆ alkyl; or (iii) R³$^a$ and R³$^b$ together are (CH₂)$_f$ so as to form a spiro ring; or (iv) R³$^a$ is hydrogen and R³$^b$ and R² together are (CH₂)$_n$ so as to form a cyclic ring that includes the adjoining N and C atoms; or (v) R³$^b$ is hydrogen and R³$^a$ and R² together are (CH₂)$_n$ so as to form a cyclic ring that includes the adjoining N and C atoms; or (vi) R³$^a$ is H and R³$^b$ is H, CH₃, CH₂CH₃, CH(CH₃)₂, CH₂CH(CH₃)₂, CH(CH₃)CH₂CH₃, CH₂Ph, CH₂-indol-3-yl, —CH₂CH₂SCH₃, CH₂CO₂H, CH₂C(O)NH₂, CH₂CH₂COOH, CH₂CH₂C(O)NH₂, CH₂CH₂CH₂CH₂NH₂, —CH₂CH₂CH₂NHC(NH)NH₂, CH₂-imidazol-4-yl, CH₂OH, CH(OH)CH₃, CH₂((4'-OH)-Ph), CH₂SH, or lower cycloalkyl; or (viii) R³$^a$ is CH₃, —CH₂CH₃, CH(CH₃)₂, CH₂CH(CH₃)₂, CH(CH₃)CH₂CH₃, CH₂Ph, CH₂-indol-3-yl, —CH₂CH₂SCH₃, CH₂CO₂H, CH₂C(O)NH₂, CH₂CH₂COOH, CH₂CH₂C(O)NH₂, CH₂CH₂CH₂CH₂NH₂, —CH₂CH₂CH₂NHC(NH)NH₂, CH₂-imidazol-4-yl, CH₂OH, CH(OH)CH₃, CH₂((4'-OH)-Ph), CH₂SH, or lower cycloalkyl and R³$^b$ is H, where R³' is independently hydrogen or alkyl, which includes, but is not limited to, C₁₋₂₀ alkyl, C₁₋₁₀ alkyl, or C₁₋₆ alkyl, and R³'' is —OR' or —N(R³')₂);

c is from 1 to 6,
d is from 0 to 2,
e is from 0 to 3,
f is from 2 to 5,
n is from 2 to 4, and (d) R⁴ is hydrogen; C₁₋₁₀ alkyl optionally substituted with a lower alkyl, alkoxy, di(lower alkyl)-amino, or halogen; C₁₋₁₀ haloalkyl; C₃₋₁₀ cycloalkyl; cycloalkyl alkyl; cycloheteroalkyl; aminoacyl; aryl, such as phenyl; or heteroaryl, such as, pyridinyl; substituted aryl; or substituted heteroaryl.

Provided herein are methods of treating a disease or disorder associated with NAD+ biosynthesis, comprising administering a compound, or a stereoisomer, salt, hydrate, solvate, or crystalline form thereof, to a subject in need thereof; wherein the compound has a structure represented by formula II:

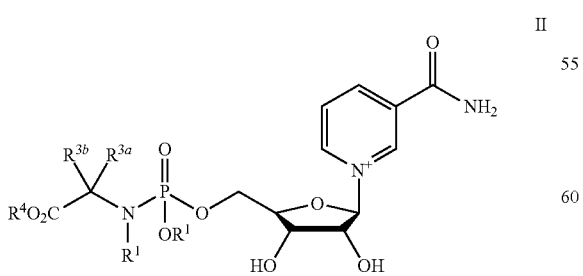

II wherein
(a) R¹ is hydrogen, n-alkyl; branched alkyl; cycloalkyl; or aryl, which includes, but is not limited to, phenyl or naphthyl, where phenyl or naphthyl are optionally substituted with at least one of C₁₋₆ alkyl, C₂₋₆ alkenyl, C₂₋₆ alkynyl, C₁₋₆ alkoxy, F, Cl, Br, I, nitro, cyano, C₁₋₆ haloalkyl, —N(R¹')₂, C₁₋₆ acylamino, —NHSO₂C₁₋₆ alkyl, —SO₂N(R¹')₂, COR¹''', and —SO₂C₁₋₆ alkyl;

R¹' is independently hydrogen or alkyl, which includes, but is not limited to, C₁₋₂₀ alkyl, C₁₋₁₀ alkyl, or C₁₋₆ alkyl, and R¹''' is —OR' or —N(R¹')₂;

(b) R² is hydrogen, C₁₋₁₀ alkyl; or C(O)CR³$^a$R³$^b$NHR¹, where n is 2 to 4; or R³$^a$ or R³$^b$ and R² together are (CH₂)$_n$ forming a cyclic ring that includes the adjoining N and C atoms;

(c) R³$^a$ and R³$^b$ are (i) independently selected from hydrogen, C₁₋₁₀ alkyl, cycloalkyl, —(CH₂)$_c$(NR³)₂, C₁₋₆ hydroxyalkyl, —CH₂SH, —(CH₂)₂S(O)$_d$Me, —(CH₂)₃NHC(=NH)NH₂, (1H-indol-3-yl)methyl, (1H-imidazol-4-yl)methyl, (CH₂)$_e$COR³''', aryl and aryl C₁₋₃ alkyl, said aryl groups optionally substituted with a group selected from hydroxyl, C₁₋₁₀ alkyl, C₁₋₆ alkoxy, halogen, nitro and cyano;

(ii) R³$^a$ and R³$^b$ both are C₁₋₆ alkyl;

(iii) R³$^a$ and R³$^b$ together are (CH₂)$_f$ so as to form a spiro ring;

(iv) R³$^a$ is hydrogen and R³$^b$ and R² together are (CH₂)$_n$ forming a cyclic ring that includes the adjoining N and C atoms;

(v) R³$^b$ is hydrogen and R³$^a$ and R² together are (CH₂)$_n$ forming a cyclic ring that includes the adjoining N and C atoms, where, and where R³' is independently hydrogen or C₁₋₆ alkyl and R³'' is —OR' or —N(R³')₂);

(vi) R³$^a$ is H and R³$^b$ is H, CH₃, CH₂CH₃, CH(CH₃)₂, CH₂CH(CH₃)₂, CH(CH₃)CH₂CH₃, CH₂Ph, CH₂-indol-3-yl, CH₂CH₂SCH₃, CH₂CO₂H, CH₂C(O)NH₂, CH₂CH₂COOH, CH₂CH₂C(O)NH₂, CH₂CH₂CH₂CH₂NH₂, CH₂CH₂CH₂NHC(NH)NH₂, CH₂-imidazol-4-yl, CH₂OH, CH(OH)CH₃, CH₂((4'-OH)-Ph), CH₂SH, or lower cycloalkyl; or (vii) R³$^a$ is CH₃, CH₂CH₃, CH(CH₃)₂, CH₂CH(CH₃)₂, CH(CH₃)CH₂CH₃, CH₂Ph, CH₂-indol-3-yl, CH₂CH₂SCH₃, CH₂CO₂H, CH₂C(O)NH₂, CH₂CH₂COOH, CH₂CH₂C(O)NH₂, CH₂CH₂CH₂CH₂NH₂, CH₂CH₂CH₂NHC(NH)NH₂, CH₂-imidazol-4-yl, CH₂OH, CH(OH)CH₃, CH₂((4'-OH)-Ph), CH₂SH, or lower cycloalkyl and R³$^b$ is H; and c is from 1 to 6,
d is from 0 to 2,
e is from 0 to 3,
f is from 2 to 5,
n is from 2 to 4, and (d) R⁴ is hydrogen, C₁₋₁₀ alkyl, C₁₋₁₀ alkyl optionally substituted with lower alkyl, alkoxy, di(lower alkyl)-amino, or halogen, C₁₋₁₀ haloalkyl, C₃₋₁₀ cycloalkyl, cycloalkyl alkyl, cycloheteroalkyl, aminoacyl, aryl, such as phenyl, heteroaryl, such as, pyridinyl, substituted aryl, or substituted heteroaryl.

Provided herein are methods of treatment as disclosed above and herein, wherein the compound is selected from

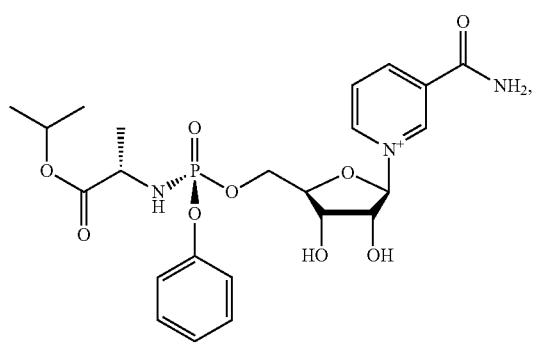

4

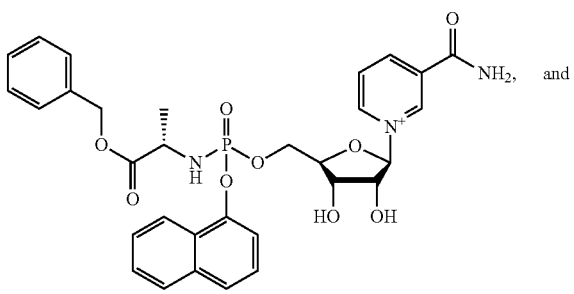

8 and

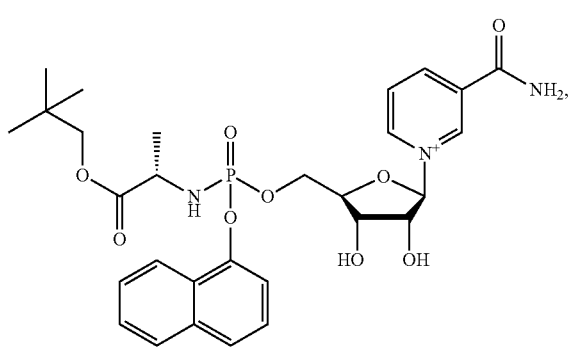

5

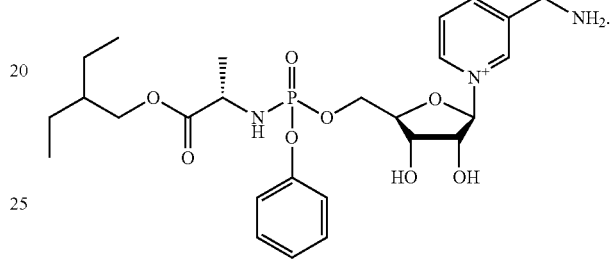

9

Provided herein are compounds, and their stereoisomers, salts, hydrates, solvates, and crystalline forms thereof, wherein the compound has a structure represented by formula III:

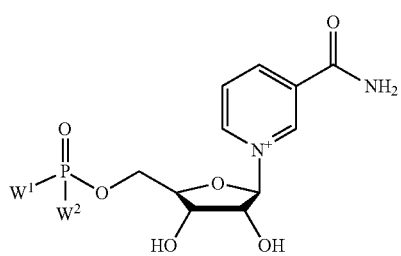

III

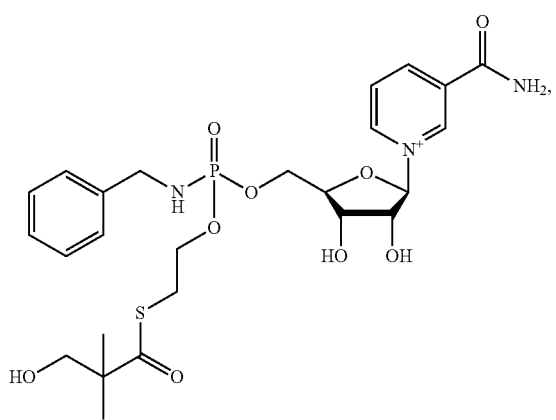

6 wherein each $W^1$ and $W^2$ is independently

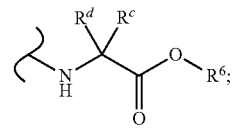

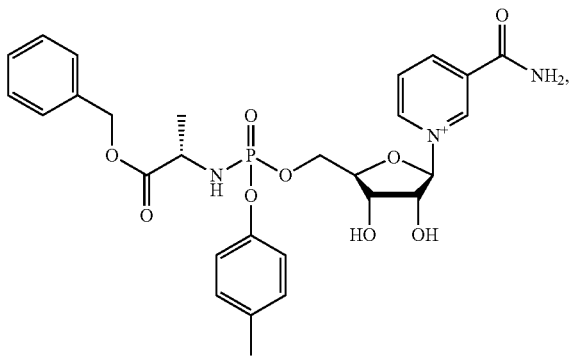

7

(i) each $R^c$ and $R^d$ is independently H, $(C_1$-$C_5)$alkyl, $(C_2$-$C_8)$alkenyl, $(C_2$-$C_8)$alkynyl, $(C_3$-$C_8)$carbocyclyl, $(C_4$-$C_8)$carbocyclylalkyl, aryl$(C_1$-$C_8)$alkyl, heterocyclyl$(C_1$-$C_8)$alkyl, $(C_6$-$C_{20})$aryl, $(C_2$-$C_{20})$heterocyclyl or heteroaryl; or (ii) each $R^c$ is H and each $R^d$ is independently $(C_1$-$C_8)$ alkyl, $(C_2$-$C_8)$alkenyl, $(C_2$-$C_8)$alkynyl, $(C_3$-$C_8)$carbocyclyl, $(C_4$-$C_8)$carbocyclylalkyl, aryl$(C_1$-$C_8)$alkyl, heterocyclyl$(C_1$-$C_8)$alkyl, $(C_6$-$C_{20})$aryl, $(C_2$-$C_{20})$ heterocyclyl or heteroaryl; or (iii) each $R^c$ is H and each $R^d$ is independently $(C_1$-$C_8)$ alkyl, $(C_2$-$C_8)$alkenyl, $(C_2$-$C_8)$alkynyl, $(C_3$-$C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S; or (iv) each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R; or (v) each $R^c$ is H and each $R^d$ is independently $(C_1-C_8)$alkyl; or (vi) each $R^c$ is H and each $R^d$ is independently $(C_1-C_8)$alkyl wherein the chirality of the carbon to which said $R^c$ and $R^d$ is attached is S; or (vii) each $R^c$ is H and each $R^d$ is independently $(C_1-C_8)$alkyl wherein the chirality of the carbon to which said $R^c$ and $R^d$ is attached is R; and each $R^6$ is independently $(C_1-C_8)$alkyl, $(C_2-C_8)$alkenyl, $(C_2-C_8)$alkynyl, $(C_3-C_8)$carbocyclyl or $(C_4-C_8)$carbocyclylalkyl.

In certain embodiments of Formula III, each

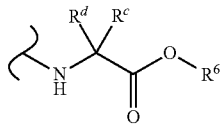

comprises a nitrogen-linked naturally occurring α-amino acid ester.

In some embodiments of Formula III, each $W^1$ and $W^2$ is independently

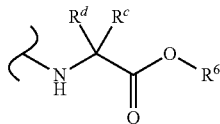

and each $R^6$ is independently $(C_1-C_8)$alkyl.

In certain embodiments, each $R^c$ and $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In certain embodiments, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In certain embodiments, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl, wherein the chirality of the carbon to which said $R^c$ and $R^d$ is attached is S. In certain embodiments, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl, wherein the chirality of the carbon to which said $R^c$ and $R^d$ is attached is R. In certain embodiments, each $R^c$ is H and each $R^d$ is independently $(C_1-C_8)$alkyl. In certain embodiments, each $R^c$ is H and each $R^d$ is independently $(C_1-C_8)$alkyl, wherein the chirality of the carbon to which said $R^c$ and $R^d$ is attached is S. In certain embodiments, each $R^c$ is H and each $R^d$ is independently $(C_1-C_8)$alkyl, wherein the chirality of the carbon to which said $R^c$ and $R^d$ is attached is R.

In certain embodiments, each

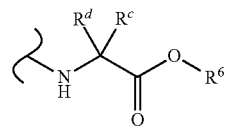

comprises a nitrogen-linked naturally occurring α-amino acid ester.

In some embodiments of Formula III, each $W^1$ and $W^2$ is independently

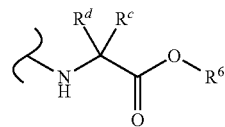

and each $R^6$ is independently $(C_1-C_8)$alkyl.

In certain embodiments, each $R^6$ is independently secondary alkyl. In certain embodiments, each $R^6$ is 2-propyl. In certain embodiments, each $R^c$ is H and each $R^d$ is methyl. In certain embodiments, each $R^c$ is H and each $R^d$ is methyl, wherein the chirality of the carbon to which said $R^c$ and $R^d$ is attached is S. In certain embodiments, each $R^c$ is H and each $R^d$ is methyl, wherein the chirality of the carbon to which said $R^c$ and $R^d$ is attached is R.

In certain embodiments, each

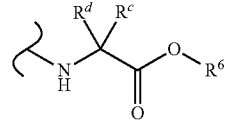

comprises a nitrogen-linked naturally occurring α-amino acid ester.

In some embodiments of Formula III, one of $W^1$ or $W^2$ is $OR^5$ and the other of $W^1$ or $W^2$ is

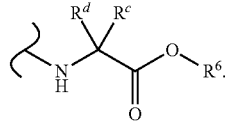

In certain embodiments, $R^5$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In certain embodiments, $R^5$ is $(C_1-C_8)$alkyl. In certain embodiments, $R^5$ is $(C_6-C_{20})$aryl, $(C_2-C_{20})$heterocyclyl or heteroaryl. In certain embodiments, $R^5$ is $(C_6-C_{20})$aryl. In certain embodiments, $R^5$ is phenyl.

In certain embodiments, each

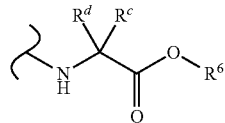

comprises a nitrogen-linked naturally occurring α-amino acid ester.

In some embodiments of Formula III, one of $W^1$ or $W^2$ is $OR^5$ and the other of $W^1$ or $W^2$ is

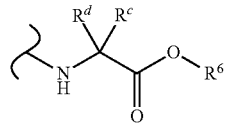

wherein $R^5$ is unsubstituted phenyl.

In certain embodiments, each $R^c$ and $R^d$ is independently H, $(C_1-C_8)$alkyl, $(C_2-C_8)$alkenyl, $(C_2-C_8)$alkynyl, $(C_3-C_8)$ carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In certain embodiments, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In certain embodiments, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl, wherein the chirality of the carbon to which said $R^c$ and $R^d$ is attached is S. In certain embodiments, one of $R^c$ or $R^d$ is H and the other of $R^c$ or $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$ heterocyclyl or heteroaryl, wherein the chirality of the carbon to which said $R^c$ and $R^d$ is attached is R. In certain embodiments, one of $R^c$ or $R^d$ is H and the other of $R^c$ or $R^d$ is $(C_1-C_8)$alkyl. In certain embodiments, one of $R^c$ or $R^d$ is H and the other of $R^c$ or $R^d$ is $(C_1-C_8)$alkyl, wherein the chirality of the carbon to which said $R^c$ and $R^d$ is attached is S. In certain embodiments, one of $R^c$ or $R^d$ is H and the other of $R^c$ or $R^d$ is $(C_1-C_8)$alkyl, wherein the chirality of the carbon to which said $R^c$ and $R^d$ is attached is R. In certain embodiments, the chirality at phosphorus is S. In certain embodiments, the chirality at phosphorus is R.

In certain embodiments, each

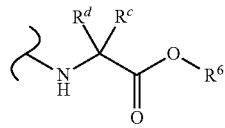

comprises a nitrogen-linked naturally occurring α-amino acid ester.

In some embodiments of Formula III, one of $W^1$ or $W^2$ is $OR^5$ and the other of W or $W^2$ is

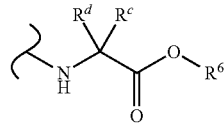

wherein one of $R^c$ or $R^d$ is H and the other of $R^c$ or $R^d$ is methyl.

In certain embodiments, one of $R^c$ or $R^d$ is H and the other of $R^c$ or $R^d$ is methyl, wherein the chirality of the carbon to which said $R^c$ and $R^d$ is attached is S. In certain embodiments, one of $R^c$ or $R^d$ is H and the other of $R^c$ or $R^d$ is methyl, wherein the chirality of the carbon to which said $R^c$ and $R^d$ is attached is R. In certain embodiments, $R^5$ is phenyl.

In certain embodiments, each

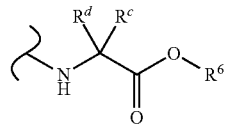

comprises a nitrogen-linked naturally occurring α-amino acid ester.

In some embodiments of Formula III, one of $W^1$ or $W^2$ is $OR^5$ and the other of $W^1$ or $W^2$ is

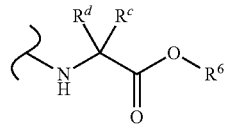

wherein $R^5$ is unsubstituted phenyl, one of $R^c$ or $R^d$ is H and the other of $R^c$ or $R^d$ is methyl.

In certain embodiments, the chirality at phosphorous is R. In certain embodiments, the chirality at phosphorous is S. In certain embodiments the chirality of the carbon to which said $R^c$ and $R^d$ is attached is S. In certain embodiments, the chirality of the carbon to which said $R^c$ and $R^d$ is attached is S and the chirality at phosphorus is S. In certain embodiments, the chirality of the carbon to which said $R^c$ and $R^d$ is attached is S and the chirality at phosphorus is R. In certain embodiments, the chirality of the carbon to which said $R^c$ and $R^d$ is attached is R. In certain embodiments, the chirality of the carbon to which said $R^c$ and $R^d$ is attached is R and the chirality at phosphorus is S. In certain embodiments, the chirality of the carbon to which said $R^c$ and $R^d$ is attached is R and the chirality at phosphorus is R.

In certain embodiments, each

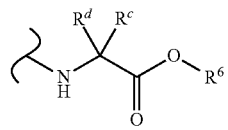

comprises a nitrogen-linked naturally occurring α-amino acid ester.

In some embodiments of Formula III, one of $W^1$ or $W^2$ is $OR^5$ and the other of $W^1$ or $W^2$ is

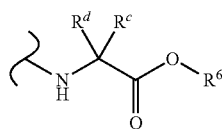

wherein $R^5$ is unsubstituted phenyl and $R^6$ is $(C_1-C_8)$alkyl, $(C_2-C_8)$alkenyl, $(C_2-C_8)$alkynyl, $(C_3-C_8)$carbocyclyl, or $(C_4-C_8)$carbocyclylalkyl.

In certain embodiments, $R^6$ is $(C_1-C_8)$alkyl. In certain embodiments, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In certain embodiments, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl, wherein the chirality of the carbon to which said $R^c$ and $R^d$ is attached is S. In certain embodiments, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl, wherein the chirality of the carbon to which said $R^c$ and $R^d$ is attached is R. In certain embodiments, one of $R^c$ or $R^d$ is H and the other of $R^c$ or $R^d$ is $(C_1-C_8)$alkyl. In certain embodiments, one of $R^c$ or $R^d$ is H and the other of $R^c$ or $R^d$ is $(C_1-C_8)$alkyl, wherein the chirality of the carbon to which said $R^c$ and $R^d$ is attached is S. In certain embodiments, one of $R^c$ or $R^d$ is H and the other of $R^c$ or $R^d$ is $(C_1-C_8)$alkyl, wherein the chirality of the carbon to which said $R^c$ and $R^d$ is attached is R. In certain embodiments, the chirality at phosphorus is S. In certain embodiments, the chirality at phosphorus is R.

In certain embodiments, each

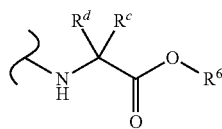

comprises a nitrogen-linked naturally occurring α-amino acid ester.

In some embodiments of Formula III, one of $W^1$ or $W^2$ is $OR^5$ and the other of $W^1$ or $W^2$ is

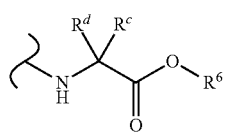

wherein one of $R^c$ or $R^d$ is H and the other of $R^c$ or $R^d$ is methyl and $R^6$ is $(C_1-C_8)$alkyl.

In certain embodiments, $R^6$ is secondary alkyl. In certain embodiments, $R^6$ is 2-propyl. In certain embodiments, the chirality of the carbon to which said $R^c$ and $R^d$ is attached is S. In certain embodiments, the chirality of the carbon to which said $R^c$ and $R^d$ is attached is R. In certain embodiments, $R^5$ is phenyl.

In certain embodiments, each

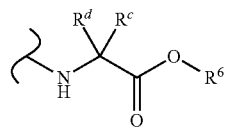

comprises a nitrogen-linked naturally occurring α-amino acid ester.

In some embodiments of Formula III, one of $W^1$ or $W^2$ is $OR^5$ and the other of $W^1$ or $W^2$ is

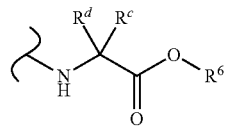

wherein $R^5$ is unsubstituted phenyl, one of $R^c$ or $R^d$ is H and the other of $R^c$ or $R^d$ is methyl and $R^6$ is $(C_1-C_8)$alkyl.

In certain embodiments, $R^6$ is secondary alkyl. In certain embodiments, $R^6$ is 2-propyl. In certain embodiments, the chirality of the carbon to which said $R^c$ and $R^d$ is attached is S. In certain embodiments, the chirality of the carbon to which said $R^c$ and $R^d$ is attached is R.

In certain embodiments, each

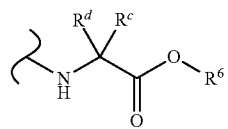

comprises a nitrogen-linked naturally occurring α-amino acid ester.

In certain embodiments, each $R^c$ is H and each $R^d$ is methyl. In certain embodiments, each $R^c$ is H and each $R^d$ is methyl, wherein the chirality of the carbon to which each said $R^c$ and $R^d$ is attached is S. In certain embodiments, each $R^c$ is H and each $R^d$ is methyl, wherein the chirality of the carbon to which each said $R^c$ and $R^d$ is attached is R. In certain embodiments, $R^5$ is phenyl.

In certain embodiments, each $R^6$ is independently $(C_1-C_8)$alkyl. In certain embodiments, each $R^6$ is independently secondary alkyl. In certain embodiments, each $W^1$ and $W^2$ is independently

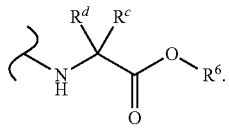

In some embodiments, one of $W^1$ or $W^2$ is $OR^5$ and the other of $W^1$ or $W^2$ is

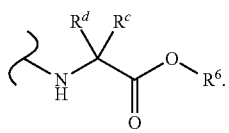

In some embodiments, each

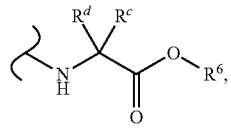

comprises a nitrogen-linked naturally occurring α-amino acid ester.

In certain embodiments, one of $R^c$ or $R^d$ is H and the other of $R^c$ or $R^d$ is methyl. In certain embodiments, one of $R^c$ or $R^d$ is H and the other of $R^c$ or $R^d$ is methyl, wherein the chirality of the carbon to which said $R^c$ and $R^d$ is attached is S. In certain embodiments, one of $R^c$ or $R^d$ is H and the other of $R^c$ or $R^d$ is methyl, wherein the chirality of the carbon to which said $R^c$ and $R^d$ is attached is R. In certain embodiments, $R^5$ is phenyl. In certain embodiments, the chirality at phosphorus is S. In certain embodiments, the chirality at phosphorus is R.

In certain embodiments, each

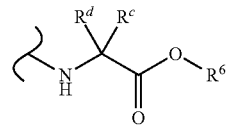

comprises a nitrogen-linked naturally occurring α-amino acid ester.

In certain embodiments, $R^6$ is $(C_1-C_8)$alkyl. In certain embodiments, $R^6$ is secondary alkyl. In certain embodiments, one of $R^c$ or $R^d$ is H and the other of $R^c$ or $R^d$ is methyl. In certain embodiments, one of $R^c$ or $R^d$ is H and the other of $R^c$ or $R^d$ is methyl, wherein the chirality of the carbon to which said $R^c$ and $R^d$ is attached is S. In certain embodiments, one of $R^c$ or $R^d$ is H and the other of $R^c$ or $R^d$ is methyl, wherein the chirality of the carbon to which said $R^c$ and $R^d$ is attached is R. In certain embodiments, $R^5$ is phenyl. In certain embodiments, the chirality at phosphorus is S. In certain embodiments, the chirality at phosphorus is R.

In certain embodiments, each

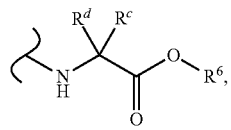

comprises a nitrogen-linked naturally occurring α-amino acid ester.

Provided herein are compounds, and their stereoisomers, salts, hydrates, solvates, and crystalline forms thereof, wherein the compound has a structure represented by formula III:

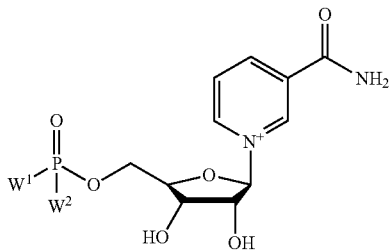

III wherein $W^1$ and $W^2$ are each independently $O^-$ or $OR^5$, and $R^5$ is hydrogen or alkyl; provided that when $W^1$ is $O^-$, and $W^2$ is $OR^5$, then $R^5$ is not hydrogen, methyl or butyl.

In certain embodiments, $R^5$ is $(C_1-C_8)$alkyl. In certain embodiments, $R^5$ is selected from methyl, ethyl, n-propyl, isopropyl, and butyl. In certain embodiments, one $R^5$ is hydrogen and the other $R^5$ is methyl. In certain embodiments, one $R^5$ is hydrogen and the other $R^5$ is methyl. In certain embodiments, one $R^5$ is $O^-$ and the other $R^5$ is $C_2$, $C_3$, or $C_5-C_8$-alkyl. In certain embodiments, both $R^5$ are $(C_1-C_8)$alkyl.

Provided herein are compounds, and their stereoisomers, salts, hydrates, solvates, and crystalline forms thereof, wherein the compound has a structure represented by formula III:

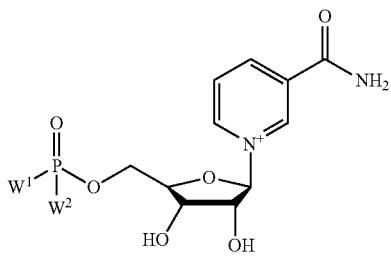

III wherein $W^1$ and $W^2$ are independently selected from the substituents in Table 1. Synthesis and general descriptions of representative substituents can be found, for instance, in U.S. Pat. No. 8,318,682, incorporated herein by reference in its entirety. The variables used in Table 1 (e.g., $W^{23}$, $R^{21}$, etc.) pertain only to Table 1, unless otherwise indicated.

The variables used in Table 1 have the following definitions:

each $R^{21}$ is independently H or $(C_1-C_8)$alkyl;
each $R^{22}$ is independently H, $R^{21}$, $R^{23}$ or $R^{24}$, wherein each $R^{24}$ is independently substituted with 0 to 3 $R^{23}$;
each $R^{23}$ is independently $R^{23a}$, $R^{23b}$, $R^{23c}$ or $R^{23d}$, provided that when $R^{23}$ is bound to a heteroatom, then $R^{23}$ is $R^{23c}$ or $R^{23d}$;
each $R^{23a}$ is independently F, Cl, Br, I, —CN, —$N_3$ or —$NO_2$;
each $R^{23b}$ is independently $Y^{21}$;
each $R^{23c}$ is independently —$R^{2x}$, —$OR^{2x}$, —$N(R^{2x})(R^{2x})$, —$SR^{2x}$, —$S(O)R^{2x}$, —$S(O)_2R^{2x}$, —$S(O)(OR^{2x})$, —$S(O)_2(OR^{2x})$, —$OC(=Y^{21})R^{2x}$, —$OC(=Y^{21})OR^{2x}$, —$OC(=Y^{21})(N(R^{2x})(R^{2x}))$, —$SC(=Y^{21})R^{2x}$, —$SC(=Y^{21})OR^{2x}$, —$SC(=Y^{21})(N(R^2)(R^{2x}))$, —$N(R^{2x})C(=Y^{21})R^{2x}$, —$N(R^{2x})C(=Y^{21})OR^{2x}$, or —$N(R^{2x})C(=Y^{21})(N(R^{2x})(R^{2x}))$;

each $R^{23d}$ is independently —C(=Y$^{21}$)R$^{2x}$; —C(=Y$^{21}$)OR$^{2x}$ or —C(=Y$^{21}$)(N(R$^{2x}$)(R$^{2x}$));

each $R^{2x}$ is independently H, (C$_1$-C$_8$)alkyl, (C$_2$-C$_8$)alkenyl, (C$_2$-C$_8$)alkynyl, aryl, heteroaryl; or two $R^{2x}$ taken together with a nitrogen or oxygen to which they are both attached form a 3 to 7 membered heterocyclic ring wherein any one carbon atom of said heterocyclic ring can optionally be replaced with —O—, —S— or —NR$^{21}$—; and wherein one or more of the non-terminal carbon atoms of each said (C$_1$-C$_8$)alkyl may be optionally replaced with —O—, —S— or —NR$^{21}$—;

each $R^{24}$ is independently (C$_1$-C$_8$)alkyl, (C$_2$-C$_8$)alkenyl, or (C$_2$-C$_8$)alkynyl;

each $R^{25}$ is independently $R^{24}$, wherein each $R^{24}$ is substituted with 0 to 3 $R^{23}$ groups;

each $R^{25a}$ is independently (C$_1$-C$_8$)alkylene, (C$_2$-C$_8$)alkenylene, or (C$_2$-C$_8$)alkynylene, any one of which said (C$_1$-C$_8$)alkylene, (C$_2$-C$_8$)alkenylene, or (C$_2$-C$_8$)alkynylene is substituted with 0-3 $R^{23}$ groups;

each $W^{23}$ is independently $W^{24}$ or $W^{25}$;

each $W^{24}$ is independently $R^{25}$, —C(=Y$^{21}$)R$^{25}$, —C(=Y$^{21}$)W$^{25}$, —SO$_2$R$^{25}$, —SO$_2$W$^{25}$;

each $W^{25}$ is independently carbocycle or heterocycle wherein $W^{25}$ is independently substituted with 0 to 3 $R^{22}$ groups; and each $Y^{21}$ is independently O or S.

TABLE 1

| $W^1$ and $W^2$ Substituents | |
| --- | --- |
| 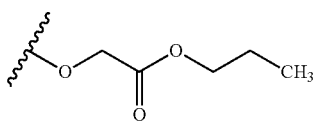 [SMILES: *OCC(=O)OCCC] | 1 |
| 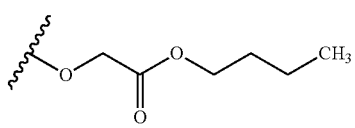 [SMILES: *OCC(=O)OCCCC] | 2 |
| 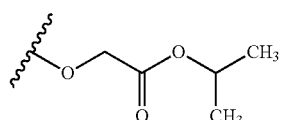 | 3 |
| 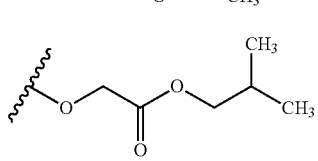 | 4 |
| 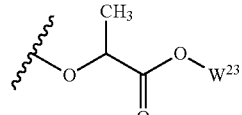 | 5 |
| 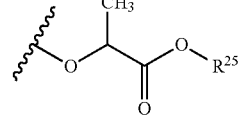 | 6 |
| 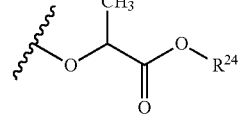 | 7 |

TABLE 1-continued

| $W^1$ and $W^2$ Substituents | |
| --- | --- |
| 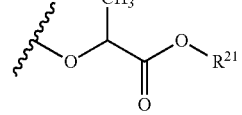 | 8 |
| 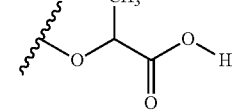 | 9 |
| 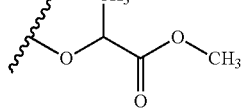 | 10 |
| 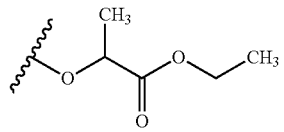 [SMILES: *OC(C)C(=O)OCC] | 11 |
| 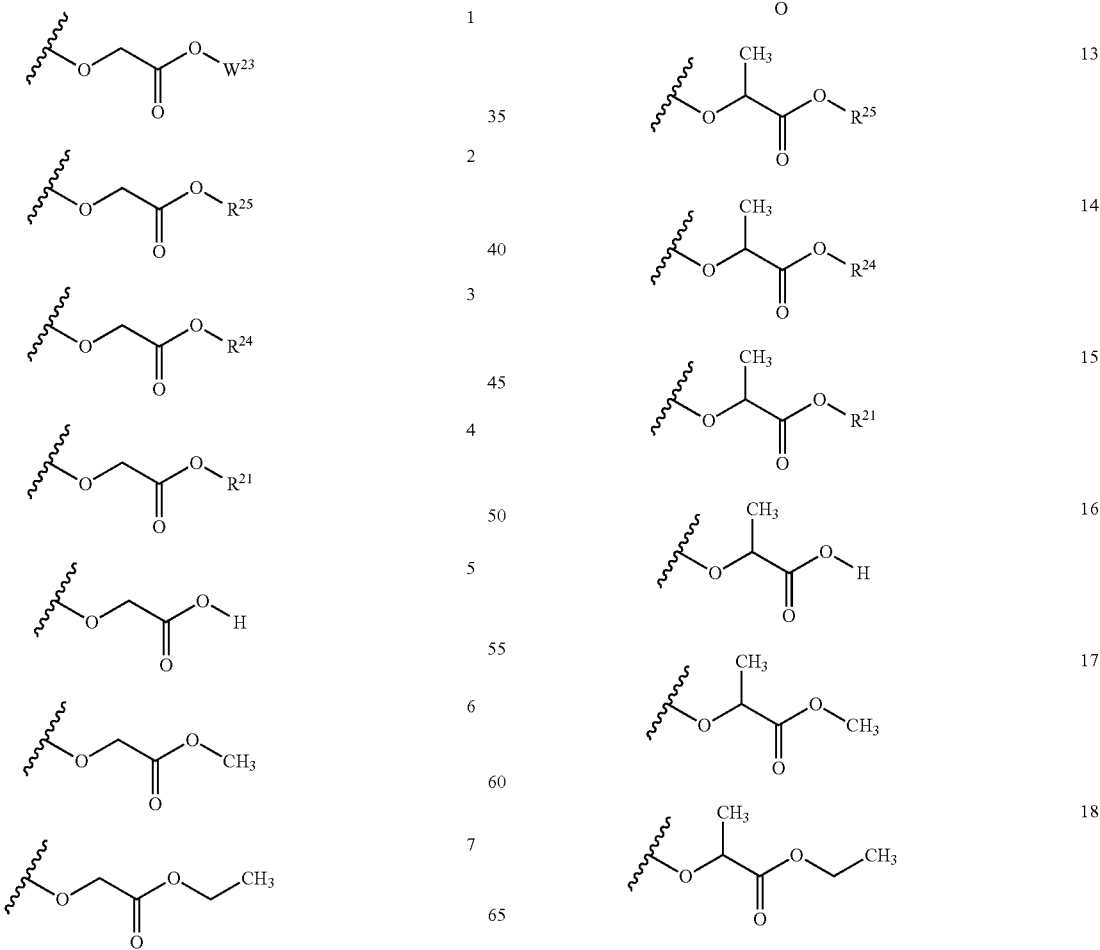 | |

TABLE 1-continued

W¹ and W² Substituents

| # | Structure |
|---|---|
| 19 | 2-(propoxycarbonyl)propoxy (CH₃ on α-C, -O-CH(CH₃)-C(=O)-O-CH₂CH₂CH₃) |
| 20 | 2-(butoxycarbonyl)propoxy |
| 21 | 2-(isopropoxycarbonyl)propoxy |
| 22 | 2-(isobutoxycarbonyl)propoxy |
| 23 | -O-CH(CH₂CH₃)-C(=O)-O-W²³ |
| 24 | -O-CH(CH₂CH₃)-C(=O)-O-R²⁵ |
| 25 | -O-CH(CH₂CH₃)-C(=O)-O-R²⁴ |
| 26 | -O-CH(CH₂CH₃)-C(=O)-O-R²¹ |
| 27 | -O-CH(CH₂CH₃)-C(=O)-OH |
| 28 | -O-CH(CH₂CH₃)-C(=O)-O-CH₃ |
| 29 | -O-CH(CH₂CH₃)-C(=O)-O-CH₂CH₃ |
| 30 | -O-CH(CH₂CH₃)-C(=O)-O-CH₂CH₂CH₃ |
| 31 | -O-CH(CH₂CH₃)-C(=O)-O-CH₂CH₂CH₂CH₃ |
| 32 | -O-CH(CH₂CH₃)-C(=O)-O-CH(CH₃)₂ |
| 33 | -O-CH(CH₂CH₃)-C(=O)-O-CH₂CH(CH₃)₂ |
| 34 | -O-CH(W²³)-C(=O)-O-W²³ |
| 35 | -O-CH(W²³)-C(=O)-O-R²⁵ |
| 36 | -O-CH(W²³)-C(=O)-O-R²⁴ |
| 37 | -O-CH(W²³)-C(=O)-O-R²¹ |
| 38 | -O-CH(R²⁵)-C(=O)-O-W²³ |

TABLE 1-continued

W¹ and W² Substituents

| # | Structure |
|---|---|
| 39 | O-CH(R25)-C(=O)-O-R25 |
| 40 | O-CH(R25)-C(=O)-O-R24 |
| 41 | O-CH(R25)-C(=O)-O-R21 |
| 42 | O-CH(R24)-C(=O)-O-W23 |
| 43 | O-CH(R24)-C(=O)-O-R25 |
| 44 | O-CH(R24)-C(=O)-O-R24 |
| 45 | O-CH(R24)-C(=O)-O-R21 |
| 46 | O-CH(R21)-C(=O)-O-W23 |
| 47 | O-CH(R21)-C(=O)-O-R25 |
| 48 | O-CH(R21)-C(=O)-O-R25 |
| 49 | O-CH(R21)-C(=O)-O-R21 |
| 50 | NH-CH2-C(=O)-O-W23 |
| 51 | NH-CH2-C(=O)-O-R25 |
| 52 | NH-CH2-C(=O)-O-R24 |
| 53 | NH-CH2-C(=O)-O-R21 |
| 54 | NH-CH2-C(=O)-O-H |
| 55 | NH-CH2-C(=O)-O-CH3 |
| 56 | NH-CH2-C(=O)-O-CH2CH3 |
| 57 | NH-CH2-C(=O)-O-CH2CH2CH3 |
| 58 | NH-CH2-C(=O)-O-CH2CH2CH2CH3 |
| 59 | NH-CH2-C(=O)-O-CH(CH3)2 |
| 60 | NH-CH2-C(=O)-O-CH2CH(CH3)2 |

TABLE 1-continued
$W^1$ and $W^2$ Substituents
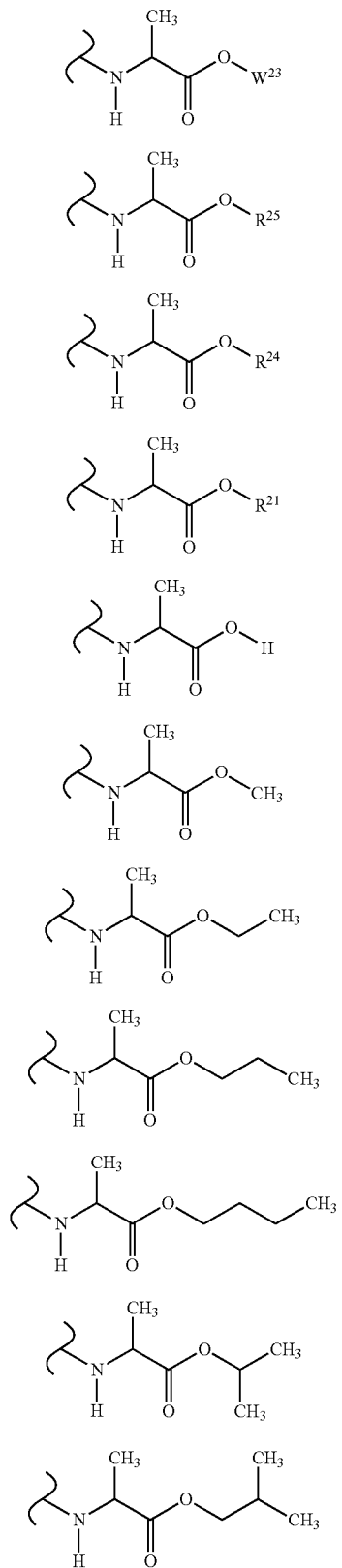
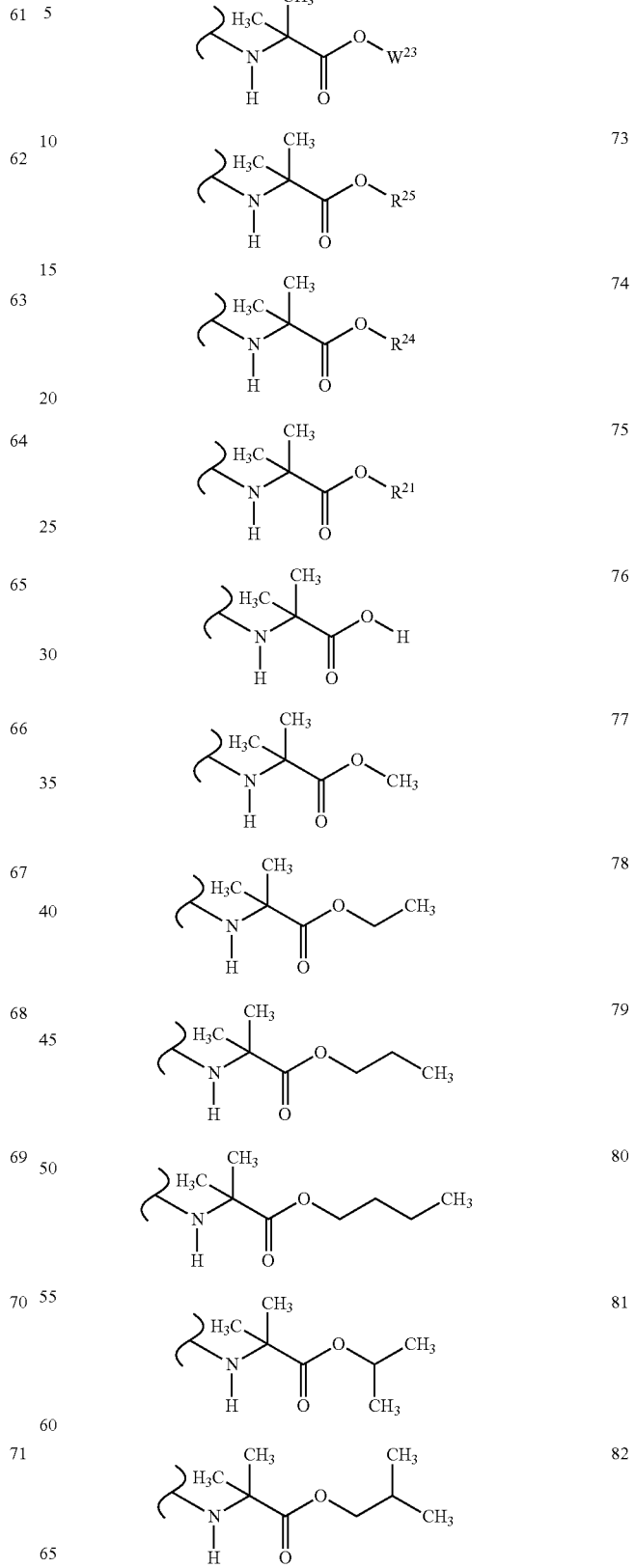

TABLE 1-continued

W¹ and W² Substituents

| Structure | No. |
|---|---|
| N(H)-CH(W²³)-C(=O)-O-W²³ | 83 |
| N(H)-CH(W²³)-C(=O)-O-R²⁵ | 84 |
| N(H)-CH(W²³)-C(=O)-O-R²⁴ | 85 |
| N(H)-CH(W²³)-C(=O)-O-R²¹ | 86 |
| N(H)-CH(R²⁵)-C(=O)-O-W²³ | 87 |
| N(H)-CH(R²⁵)-C(=O)-O-R²⁵ | 88 |
| N(H)-CH(R²⁵)-C(=O)-O-R²⁴ | 89 |
| N(H)-CH(R²⁵)-C(=O)-O-R²¹ | 90 |
| N(H)-CH(R²⁴)-C(=O)-O-W²³ | 91 |
| N(H)-CH(R²⁴)-C(=O)-O-R²⁵ | 92 |
| N(H)-CH(R²⁴)-C(=O)-O-R²⁴ | 93 |
| N(H)-CH(R²⁴)-C(=O)-O-R²¹ | 94 |
| N(H)-CH(R²¹)-C(=O)-O-W²³ | 95 |
| N(H)-CH(R²¹)-C(=O)-O-R²⁵ | 96 |
| N(H)-CH(R²¹)-C(=O)-O-R²⁴ | 97 |
| N(H)-CH(R²¹)-C(=O)-O-R²¹ | 98 |
| N(R²³)-CH₂-C(=O)-O-W²³ | 99 |
| N(R²³)-CH₂-C(=O)-O-R²⁵ | 100 |
| N(R²³)-CH₂-C(=O)-O-R²⁴ | 101 |
| N(R²³)-CH₂-C(=O)-O-R²¹ | 102 |
| N(R²³)-CH₂-C(=O)-O-CH₂CH₂CH₂CH₃ | 107 |
| N(R²³)-CH₂-C(=O)-O-CH(CH₃)₂ | 108 |

TABLE 1-continued
| W¹ and W² Substituents | |
|---|---|
| 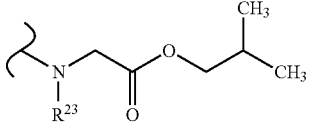 | 109 |
| 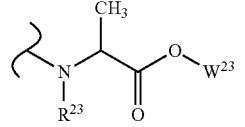 | 110 |
| 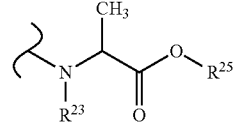 | 111 |
| 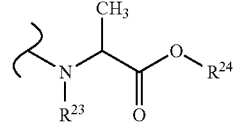 | 112 |
| 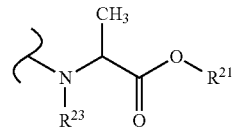 | 113 |
| 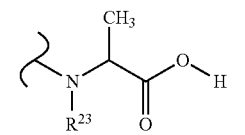 | 114 |
| 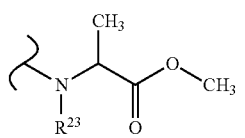 | 115 |
| 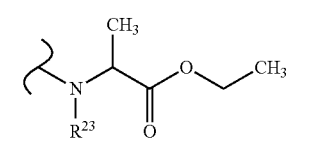 | 116 |
| 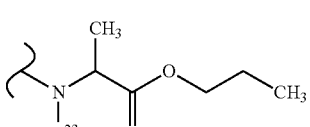 | 117 |
| 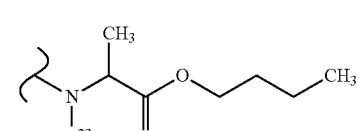 | 118 |
| 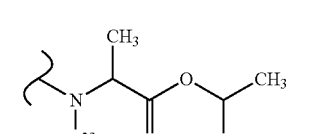 | 119 |
TABLE 1-continued
| W¹ and W² Substituents | |
|---|---|
| 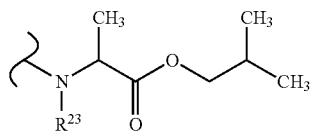 | 120 |
| 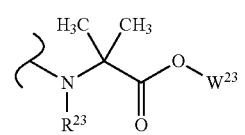 | 121 |
| 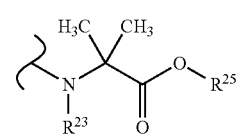 | 122 |
| 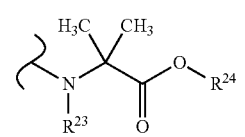 | 123 |
| 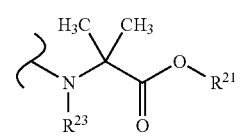 | 124 |
| 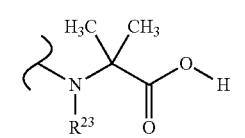 | 125 |
| 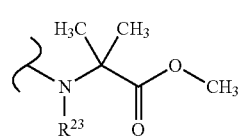 | 126 |
| 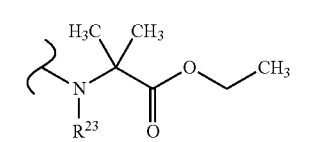 | 127 |
| 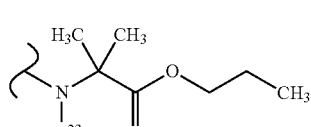 | 128 |
| 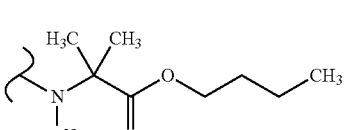 | 129 |
| 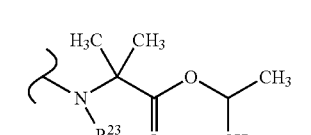 | 130 |

TABLE 1-continued

W¹ and W² Substituents

| Structure | No. |
|---|---|
| (N(R23)-C(CH3)2-C(=O)-O-CH2CH(CH3)CH3) | 131 |
| (N(R23)-CH(W23)-C(=O)-O-W23) | 132 |
| (N(R23)-CH(W23)-C(=O)-O-R25) | 133 |
| (N(R23)-CH(W23)-C(=O)-O-R24) | 134 |
| (N(R23)-CH(W23)-C(=O)-O-R21) | 135 |
| (N(R23)-CH(R25)-C(=O)-O-W23) | 136 |
| (N(R23)-CH(R25)-C(=O)-O-R25) | 137 |
| (N(R23)-CH(R25)-C(=O)-O-R24) | 138 |
| (N(R23)-CH(R25)-C(=O)-O-R21) | 139 |
| (N(R23)-CH(R24)-C(=O)-O-W23) | 140 |
| (N(R23)-CH(R24)-C(=O)-O-R25) | 141 |
| (N(R23)-CH(R24)-C(=O)-O-R24) | 142 |
| (N(R23)-CH(R24)-C(=O)-O-R21) | 143 |
| (N(R23)-CH(R21)-C(=O)-O-R24) | 144 |
| (N(R23)-CH(R21)-C(=O)-O-W23) | 144 |
| (N(R23)-CH(R21)-C(=O)-O-R25) | 145 |
| (N(R23)-CH(R21)-C(=O)-O-R24) | 146 |
| (N(R23)-CH(R21)-C(=O)-O-R21) | 147 |
| (W23) | 148 |
| (R25) | 149 |
| (R24) | 150 |
| (R21) | 151 |
| (H) | 152 |
| (R23) | 153 |
| (O-W23) | 154 |
| (O-R25) | 155 |

TABLE 1-continued
W¹ and W² Substituents
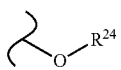 156
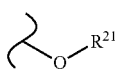 157
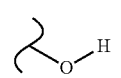 158
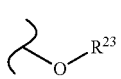 159
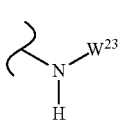 160
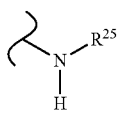 161
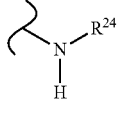 162
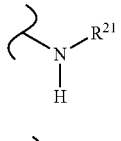 163
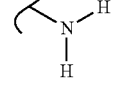 164
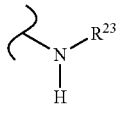 165
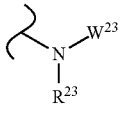 166
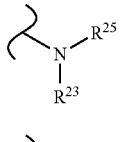 167
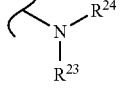 168
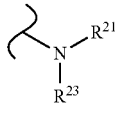 169
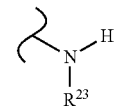 170
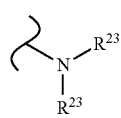 171
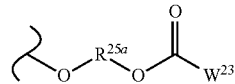 172
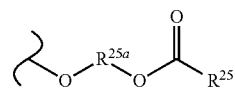 173
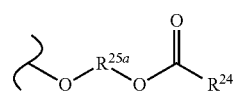 174
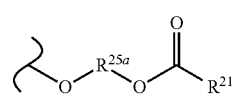 175
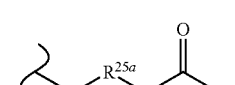 176
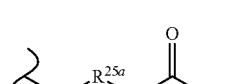 177
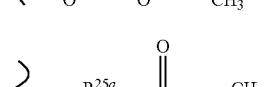 178
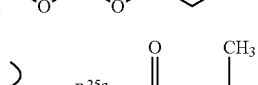 179
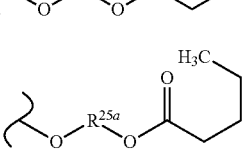 180
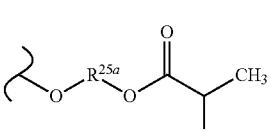 181
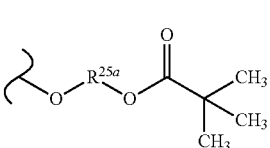 182
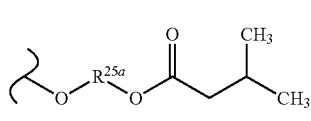 183

TABLE 1-continued

$W^1$ and $W^2$ Substituents

| # | Structure description |
|---|---|
| 184 | –O–R$^{25a}$–O–C(=O)–phenyl |
| 185 | –O–R$^{25a}$–O–C(=O)–CH$_2$–phenyl |
| 186 | –O–CH$_2$–O–C(=O)–W$^{23}$ |
| 187 | –O–CH$_2$–O–C(=O)–R$^{25}$ |
| 188 | –O–CH$_2$–O–C(=O)–R$^{24}$ |
| 189 | –O–CH$_2$–O–C(=O)–R$^{21}$ |
| 190 | –O–CH$_2$–O–C(=O)–H |
| 191 | –O–CH$_2$–O–C(=O)–CH$_3$ |
| 192 | –O–CH$_2$–O–C(=O)–CH$_2$CH$_3$ |
| 193 | –O–CH$_2$–O–C(=O)–CH$_2$CH$_2$CH$_3$ |
| 194 | –O–CH$_2$–O–C(=O)–CH$_2$CH$_2$CH$_2$CH$_3$ |
| 195 | –O–CH$_2$–O–C(=O)–CH(CH$_3$)$_2$ |
| 196 | –O–CH$_2$–O–C(=O)–C(CH$_3$)$_3$ |
| 197 | –O–CH$_2$–O–C(=O)–CH$_2$–CH(CH$_3$)$_2$ |
| 198 | –O–CH$_2$–O–C(=O)–O–phenyl |
| 199 | –O–CH$_2$–O–C(=O)–CH$_2$–phenyl |
| 200 | –O–R$^{25a}$–O–C(=O)–O–W$^{23}$ |
| 201 | –O–R$^{25a}$–O–C(=O)–O–R$^{25}$ |
| 202 | –O–R$^{25a}$–O–C(=O)–O–R$^{24}$ |
| 203 | –O–R$^{25a}$–O–C(=O)–O–R$^{21}$ |
| 204 | –O–R$^{25a}$–O–C(=O)–O–H |
| 205 | –O–R$^{25a}$–O–C(=O)–O–CH$_3$ |
| 206 | –O–R$^{25a}$–O–C(=O)–O–CH$_2$CH$_3$ |
| 207 | –O–R$^{25a}$–O–C(=O)–O–CH$_2$CH$_2$CH$_3$ |
| 208 | –O–R$^{25a}$–O–C(=O)–O–CH$_2$CH$_2$CH$_2$CH$_3$ |
| 209 | –O–R$^{25a}$–O–C(=O)–O–CH(CH$_3$)$_2$ |
| 210 | –O–R$^{25a}$–O–C(=O)–O–C(CH$_3$)$_3$ |
| 211 | –O–R$^{25a}$–O–C(=O)–O–CH$_2$–CH(CH$_3$)$_2$ |

TABLE 1-continued
W[1] and W[2] Substituents
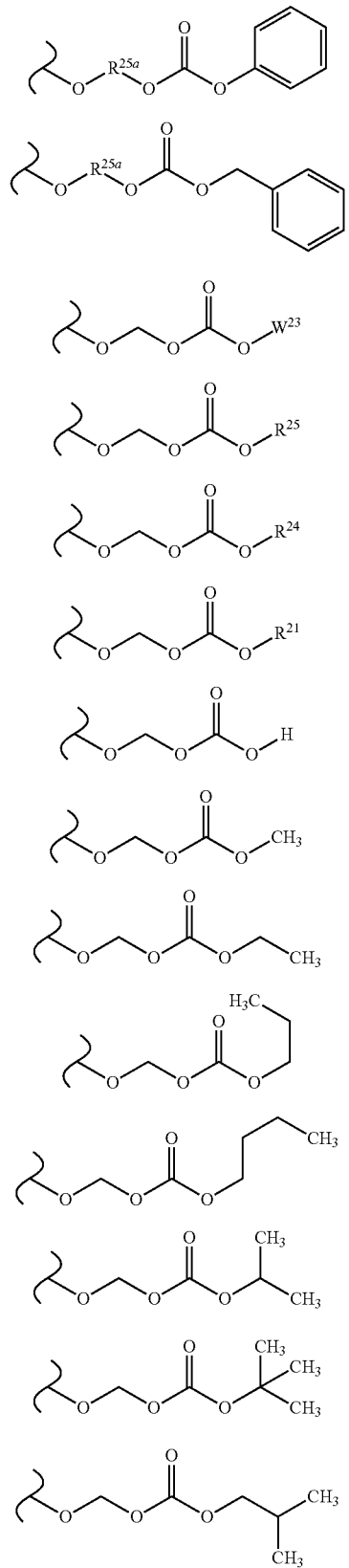
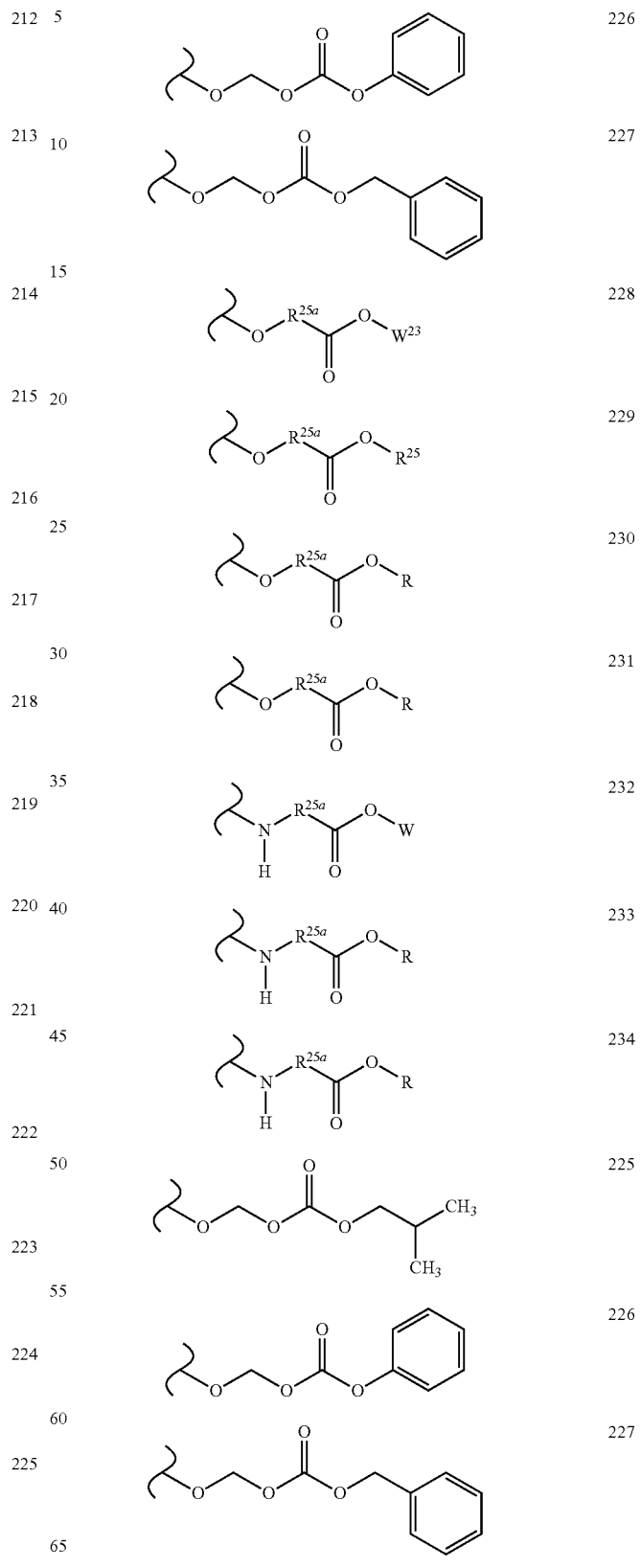

TABLE 1-continued
W¹ and W² Substituents
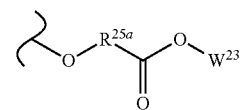 228
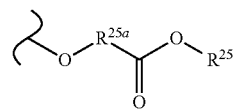 229
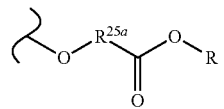 230
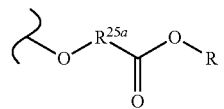 231
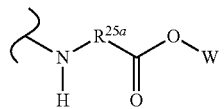 232
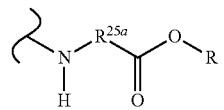 233
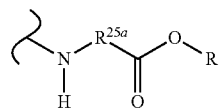 234
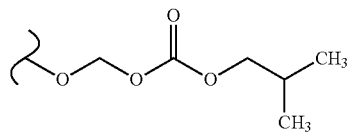 225
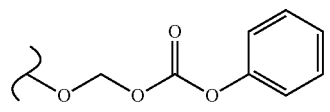 226
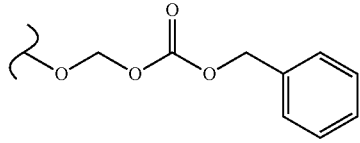 227
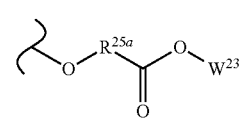 228
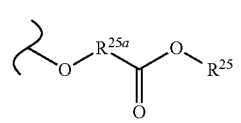 229
TABLE 1-continued
W¹ and W² Substituents
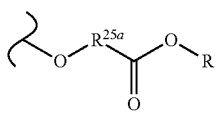 230
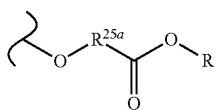 231
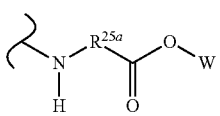 232
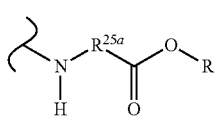 233
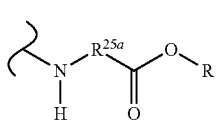 234
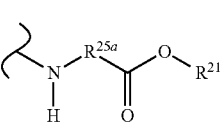 235
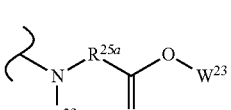 236
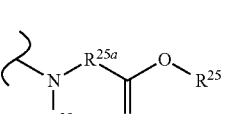 237
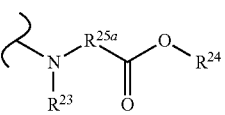 238
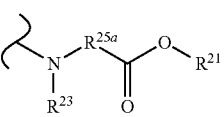 239
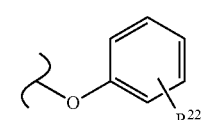 240
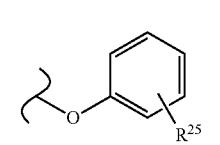 241

TABLE 1-continued
W[1] and W[2] Substituents
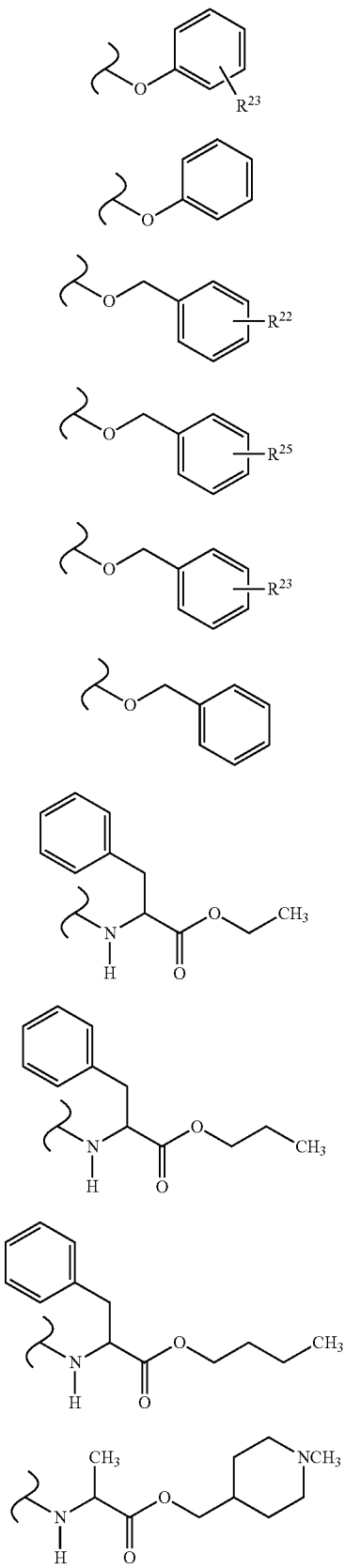
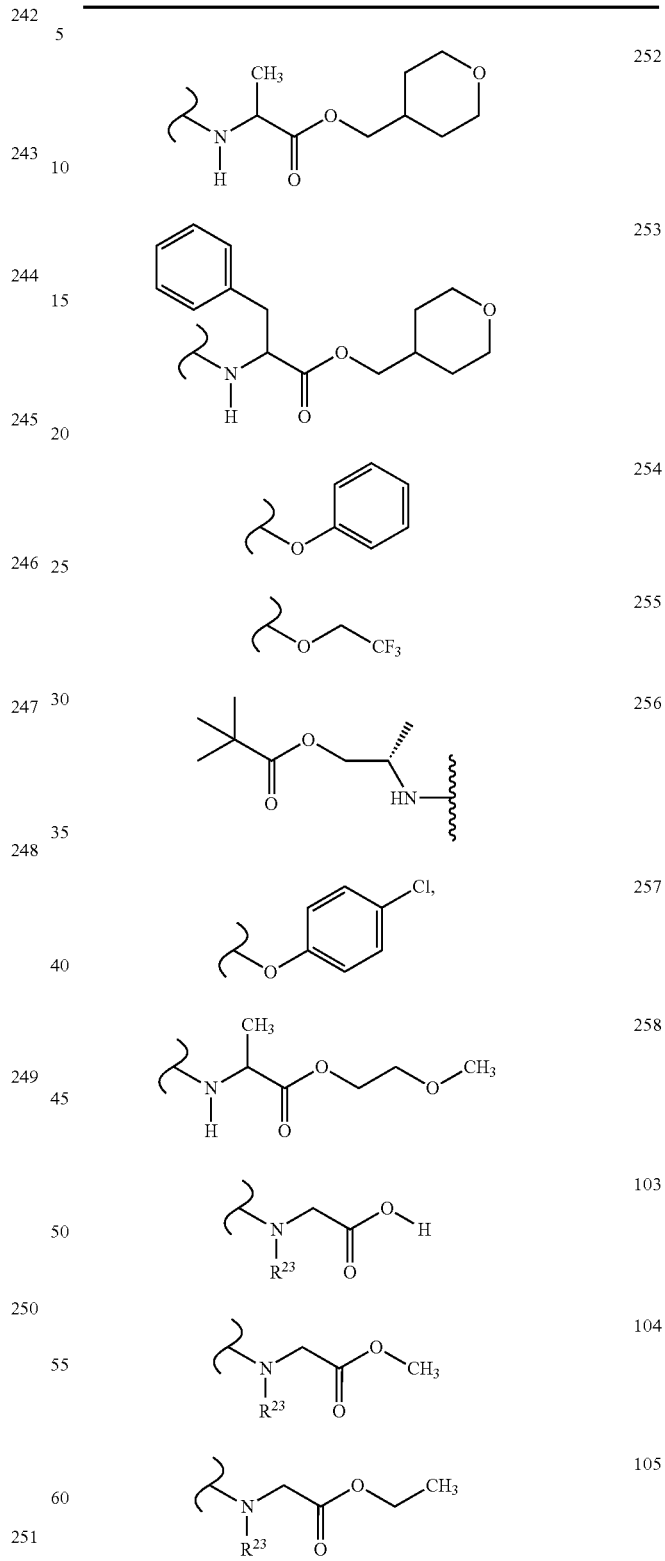
In certain embodiments, provided herein are compounds of formula III, and their stereoisomers, salts, and crystalline forms thereof.

Provided herein are methods of treating a disease or disorder associated with NAD+ biosynthesis, comprising administering a compound, or its stereoisomer, salt, hydrate, solvate, or crystalline form thereof, to a subject in need thereof; wherein the compound is represented by formula III:

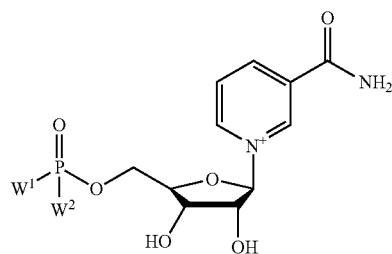

III wherein W¹ and W² are independently selected from the substituents in Table 2.

Provided herein are methods of treatment comprising administering a compound, or a stereoisomer, salt, hydrate, solvate, or crystalline form thereof, wherein the compound is

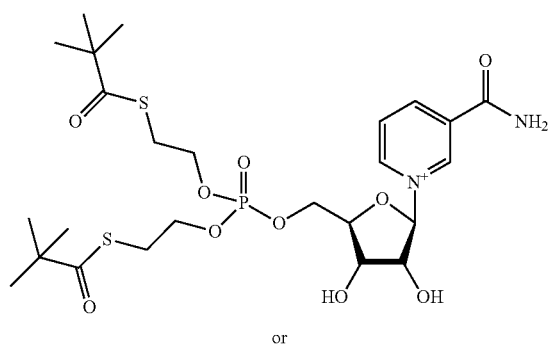

3 or

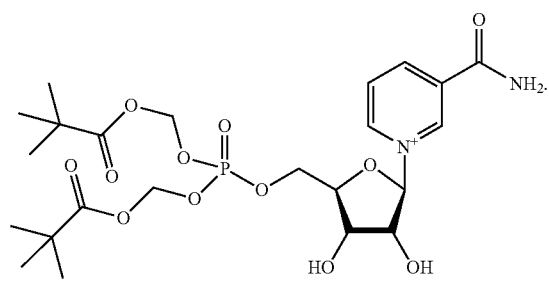

23

Provided herein are compounds, and their stereoisomers, salts, hydrates, solvates, or crystalline forms thereof, wherein the compound has a structure represented by formula I:

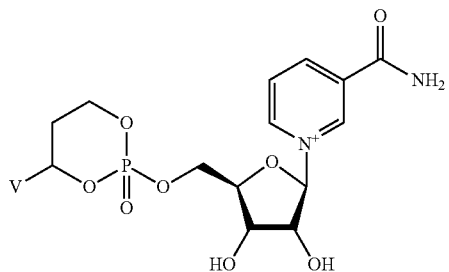

I wherein V is selected from hydrogen, phenyl and monocyclic heteroaryl, wherein (i) each said monocyclic heteroaryl contains five or six ring atoms of which 1 or 2 ring atoms are heteroatoms selected from N, S, and O, and the remainder of the ring atoms are carbon, and (ii) each said phenyl or monocyclic heteroaryl is unsubstituted or is substituted by one or two groups selected from halogen, trifluoromethyl, $C_1$-$C_6$ alkyl, $C_1$-$C_6$ alkoxy, and cyano.

In certain embodiments, provided herein are compounds of formula I, and their stereoisomers, salts, or crystalline forms thereof.

Provided herein are compounds, and their stereoisomers, salts, hydrates, solvates, or crystalline forms thereof, wherein the compound has a structure represented by formula I:

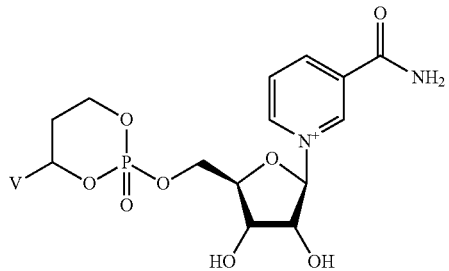

I wherein V is selected from the substituents in Table 2. Synthesis and general descriptions of representative substituents can be found, for instance, in U.S. Pat. No. 8,063,025, incorporated herein by reference in its entirety.

TABLE 2

V Substituents

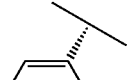

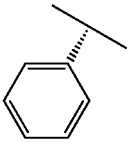

TABLE 2-continued
V Substituents
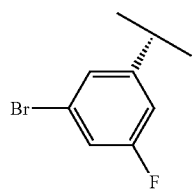
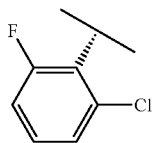
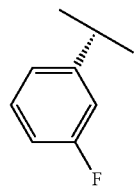
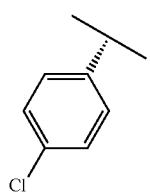
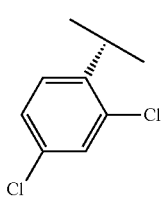
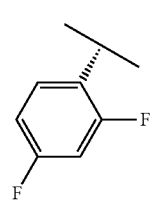
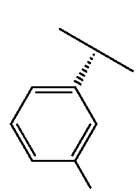
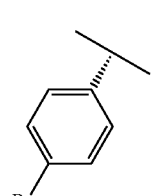
TABLE 2-continued
V Substituents
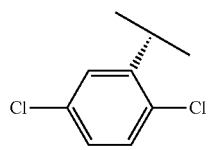
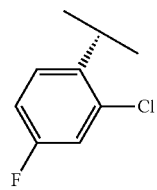
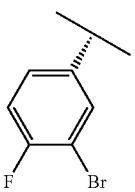
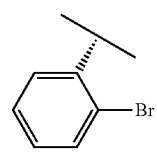
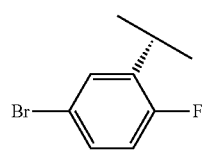
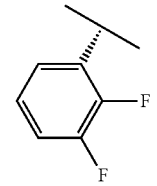
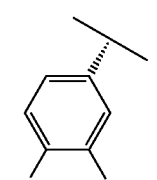
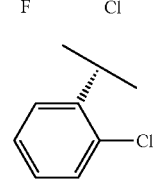
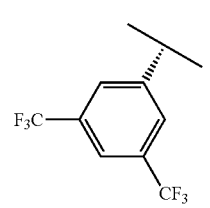

TABLE 2-continued
V Substituents
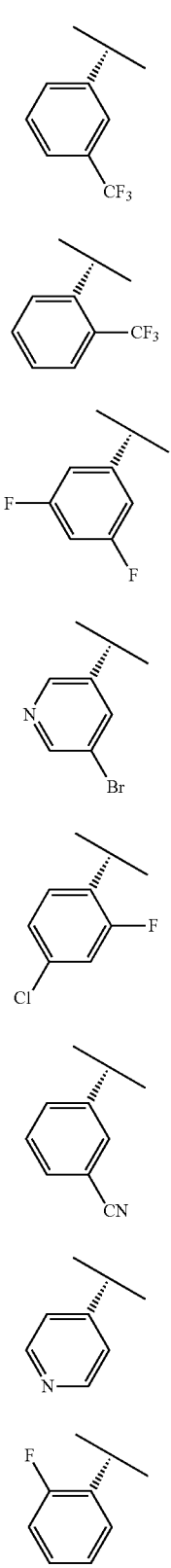
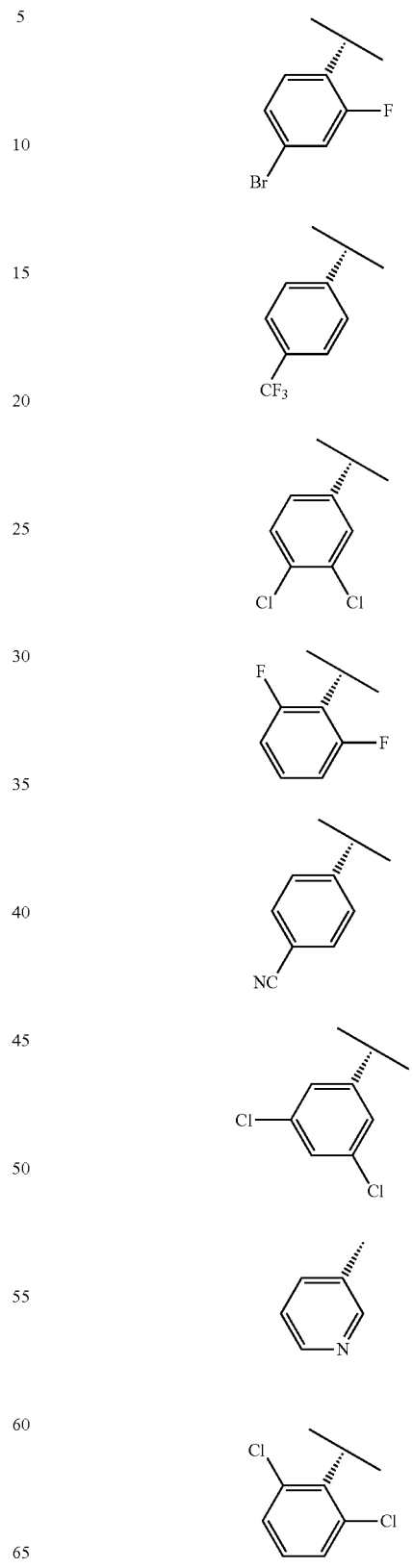

In other embodiments, the compound is selected from:

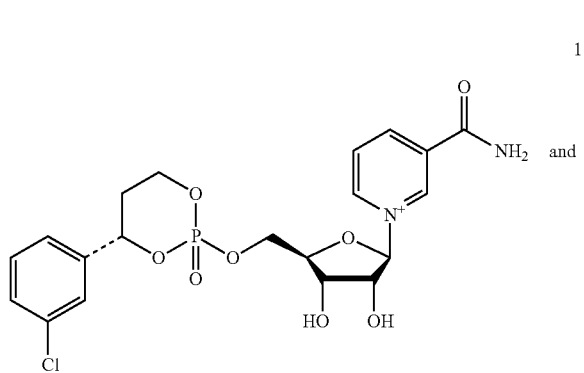

1

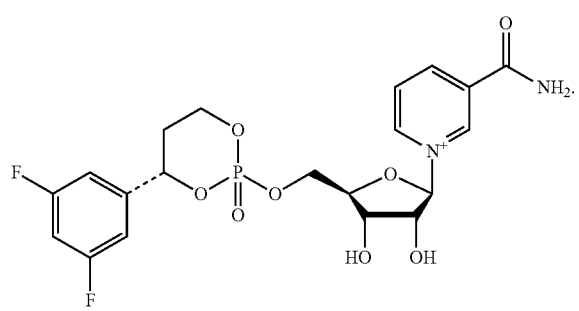

2

Provided herein are compositions for the treatment and/or prophylaxis of any of the diseases disclosed herein, said compositions comprising a pharmaceutically acceptable medium selected from an excipient, carrier, diluent, and equivalent medium and a compound, or a stereoisomer, salt, hydrate, solvate, or crystalline form thereof, wherein the compound has a structure represented by formula I:

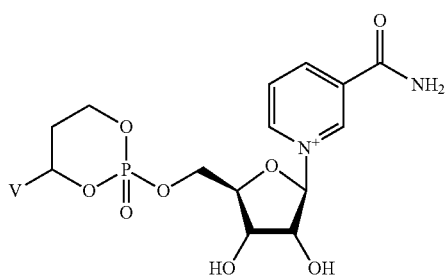

I wherein V is selected from hydrogen, phenyl and monocyclic heteroaryl, wherein (i) each said monocyclic heteroaryl contains five or six ring atoms of which 1 or 2 ring atoms are heteroatoms selected from N, S, and O, and the remainder of the ring atoms are carbon, and (ii) each said phenyl or monocyclic heteroaryl is unsubstituted or is substituted by one or two groups selected from halogen, trifluoromethyl, $C_1$-$C_6$ alkyl, $C_1$-$C_6$ alkoxy, and cyano.

Provided herein are compositions for the treatment and/or prophylaxis of any of the diseases disclosed herein, said compositions comprising a pharmaceutically acceptable medium selected from an excipient, carrier, diluent, and equivalent medium and a compound, or a stereoisomer, salt, hydrate, solvate, or crystalline form thereof, wherein the compound has a structure represented by formula I:

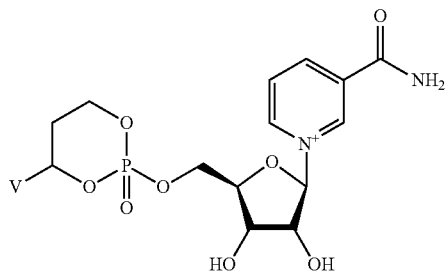

I wherein V is selected from the substituents in Table 2.

Provided herein are methods of treating a disease or disorder associated with NAD+ biosynthesis, comprising administering a compound, or a stereoisomer, salt, hydrate, solvate, or crystalline form thereof, to a subject in need thereof, wherein the compound has a structure represented by formula I:

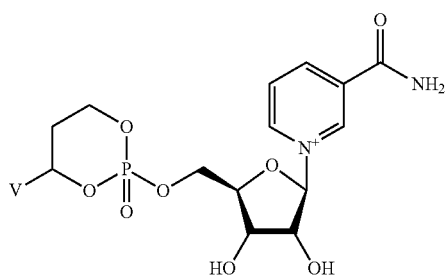

I wherein V is selected from hydrogen, phenyl and monocyclic heteroaryl, wherein (i) each said monocyclic heteroaryl contains five or six ring atoms of which 1 or 2 ring atoms are heteroatoms selected from N, S, and O, and the remainder of the ring atoms are carbon, and (ii) each said phenyl or monocyclic heteroaryl is unsubstituted or is substituted by one or two groups selected from halogen, trifluoromethyl, $C_1$-$C_6$ alkyl, $C_1$-$C_6$ alkoxy, and cyano.

Provided herein are methods of treatment in a subject in need thereof, comprising administering a therapeutically effective amount of a compound, or a stereoisomer, salt, hydrate, solvate, or crystalline form thereof, to the subject; wherein the compound has a structure represented by formula I:

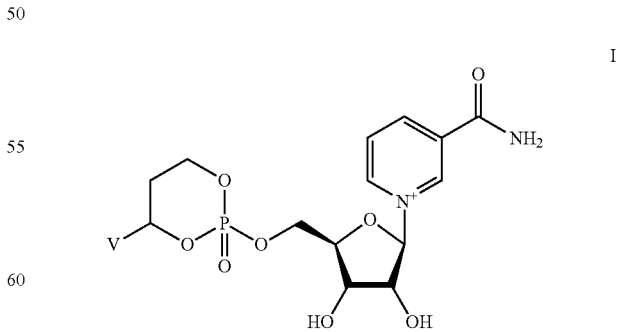

I wherein V is selected from the substituents in Table 2.

Provided herein is a compound, its stereoisomer, salt, hydrate, solvate, or crystalline form thereof, wherein the compound is selected from 1
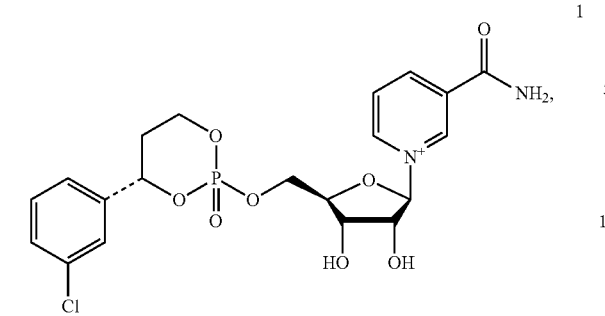
2
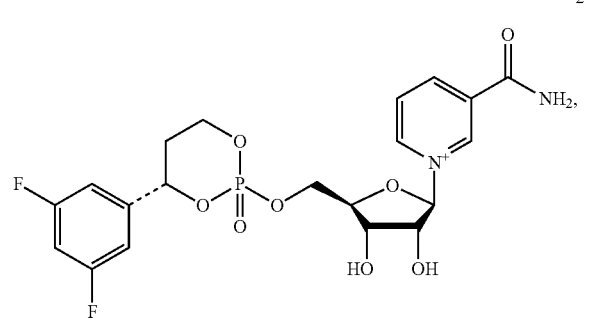
3
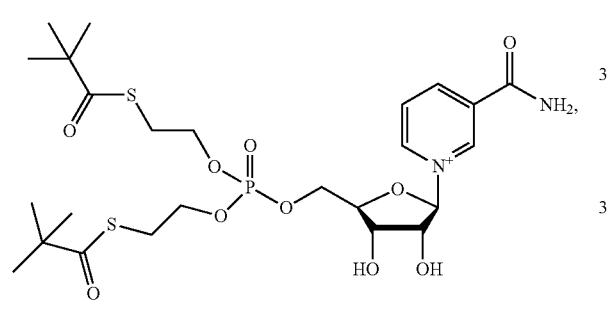
4
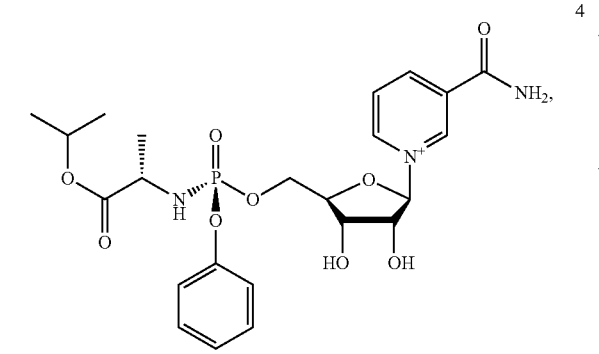
5
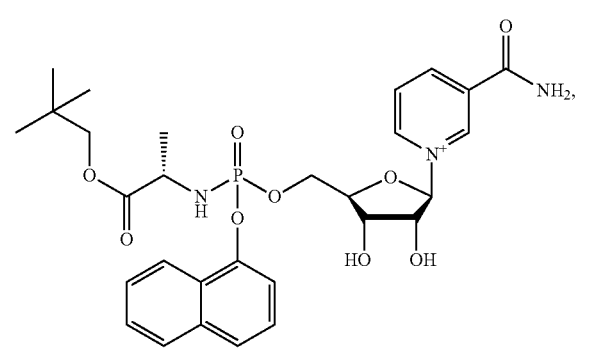
6
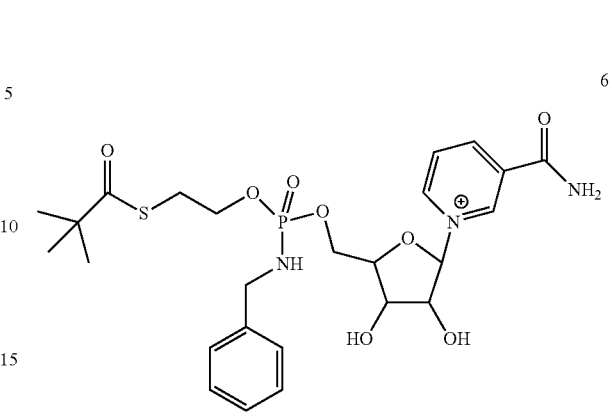
7
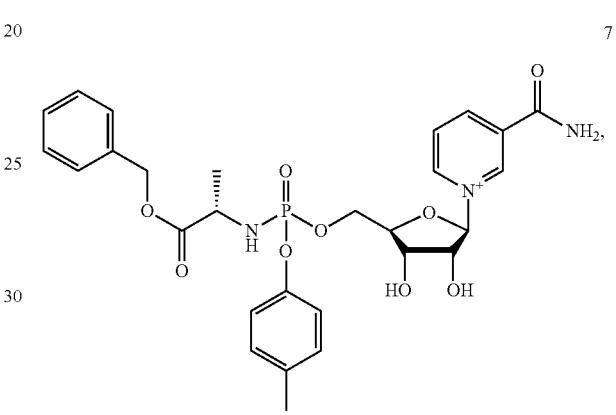
8
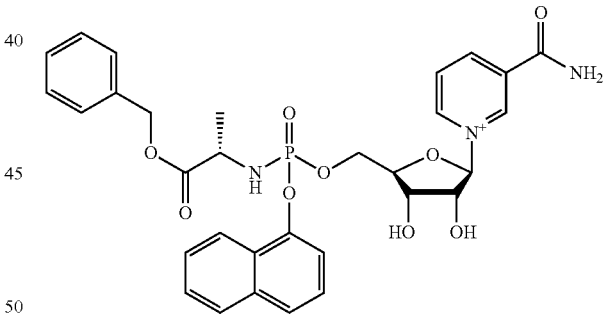
9
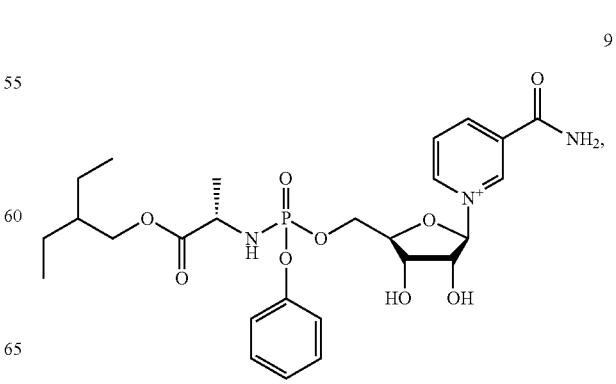

10
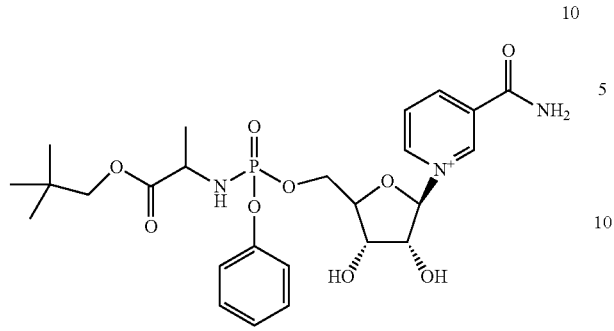
11
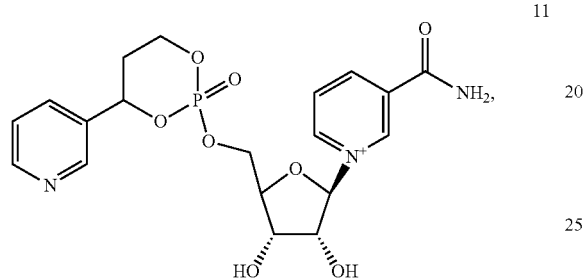
12
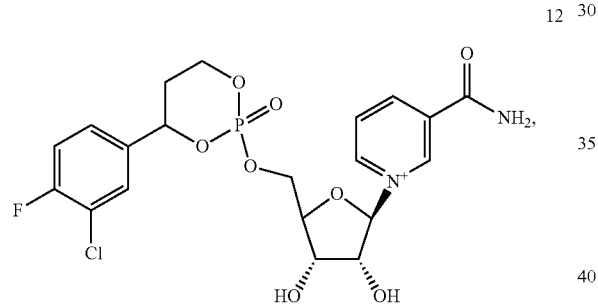
13
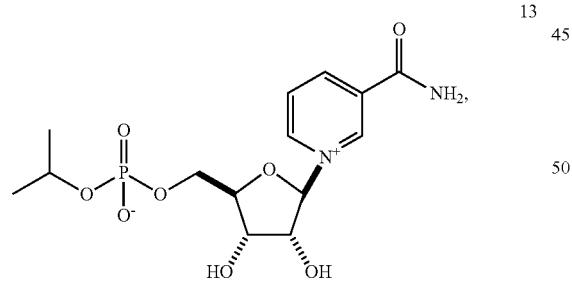
14
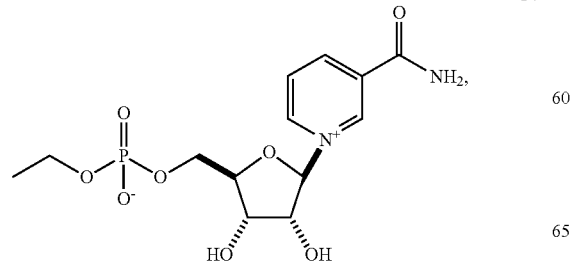
15
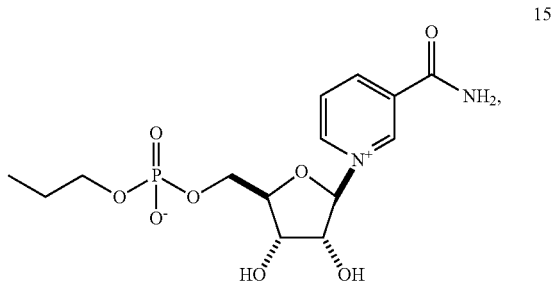
17
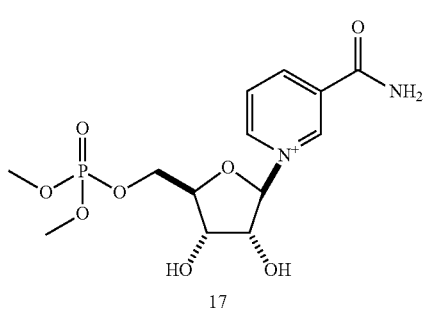
18
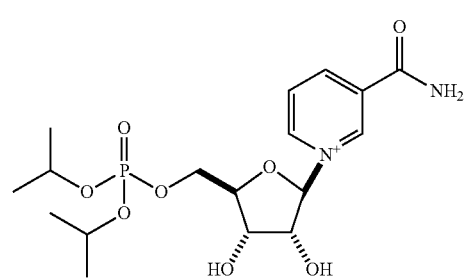
19
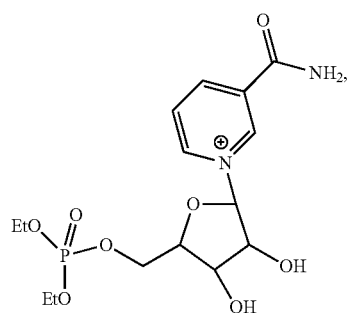
20
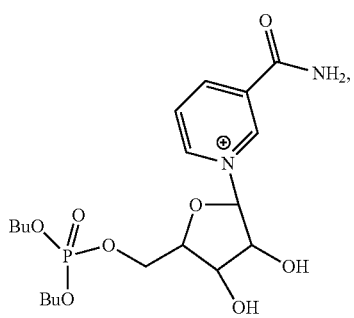

-continued

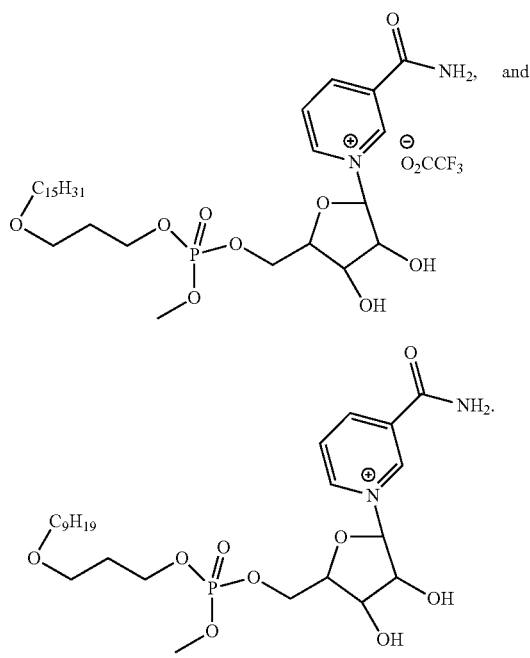

Provided herein is a compound, or a stereoisomer, salt, hydrate, solvate, or crystalline form thereof, wherein the compound is selected from Compounds 1, 2, 11, and 12. Also provided herein is a compound, or a stereoisomer, salt, hydrate, solvate, or crystalline form thereof, wherein the compound is selected from Compounds 3, 17, 18, 19, 20, 21, and 22. Also provided herein is a compound, or a stereoisomer, salt, hydrate, solvate, or crystalline form thereof, wherein the compound is selected from Compounds 4, 5, 6, 7, 8, 9, and 10. Also provided herein is a compound, or a stereoisomer, salt, hydrate, solvate, or crystalline form thereof, wherein the compound is selected from Compounds 13, 14, and 15.

In some embodiments, the disclosed compounds are in the form of a positively charged pyridium cation, which may form a salt with any suitable anion. The anion can alter as the compound is isolated or transferred into media with different anionic species. For example, a disclosed compound may be in the form a pyridium salt that is a pharmaceutically acceptable salt as described herein. In certain embodiments, the pyridium compound is isolated as a salt with an anion selected from acetate, triflate, halide, trifluoroacetate, or formate. In other embodiments, if the disclosed compound is in contact with a media, e.g., aqueous media, the anion can be selected from, for example, $OH^-$, $H_2PO_4^-$, $HPO_4^{2-}$ $HSO_4^-$, $SO_4^{2-}$, $NO_3^-$ $HCO_3^-$, and $CO_3^{2-}$.

Synthetic schemes for preparing compounds of Formula I, Formula II and Formula III can be found, for instance, in the following references incorporated herein by reference in their entirety. Nicotinamide riboside and intermediates of nicotinamide riboside with protected functionalities and well-established leaving groups that could be used in the synthesis of compounds of the present invention are described in, for example, Milburn et al. (US2006/0229265) as well as Sauve et al (U.S. Pat. No. 8,106,184). Synthetic schemes and characterization of intermediates necessary for compounds of Formula I can be found, for instance, in Heckler et al. (U.S. Pat. No. 8,063,025); Heckler et al. (U.S. application Ser. No. 12/745,419); Butler et al. (U.S. Pat. No. 8,318,682); Cho et al. (U.S. Pat. No. 8,415,308); Ross et al (U.S. application Ser. No. 13/732,725); and Ross et al (U.S. application Ser. No. 13/076,842). Protecting groups and/or leaving groups useful for synthesis of the compounds of the present invention can be found, for instance, in Ross et al. (U.S. application Ser. No. 13/076,842).

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "P*" means that the phosphorus atom is chiral and that it has a corresponding Cahn-Ingold-Prelog designation of "R" or "S" which have their accepted plain meanings.

The term "purified," as described herein, refers to the purity of a given compound. For example, a compound is "purified" when the given compound is a major component of the composition, i.e., at least about 50% w/w pure. Thus, "purified" embraces at least about 50% w/w purity, at least about 60% w/w purity, at least about 70% purity, at least about 80% purity, at least about 85% purity, at least about 90% purity, at least about 92% purity, at least about 94% purity, at least about 96% purity, at least about 97% purity, at least about 98% purity, at least about 99% purity, at least about 99.5% purity, and at least about 99.9% purity, wherein "substantially pure" embraces at least about 97% purity, at least about 98% purity, at least about 99% purity, at least about 99.5% purity, and at least about 99.9% purity.

The term "metabolite," as described herein, refers to a compound produced in vivo after administration to a subject in need thereof.

The term "substantially anhydrous" means that a substance contains at most 10% by weight of water, preferably at most 1% by weight of water, more preferably at most 0.5% by weight of water, and most preferably at most 0.1% by weight of water.

A solvent or anti-solvent (as used in reactions, crystallization, etc. or lattice and/or adsorbed solvents) includes at least one of a $C_1$ to $C_8$ alcohol, a $C_2$ to $C_8$ ether, a $C_3$ to $C_7$ ketone, a $C_3$ to $C_7$ ester, a $C_1$ to $C_2$ chlorocarbon, a $C_2$ to $C_7$ nitrile, a miscellaneous solvent, a $C_5$ to $C_{12}$ saturated hydrocarbon, and a $C_6$ to $C_{12}$ aromatic hydrocarbon.

The term $C_1$ to $C_8$ alcohol refers to a straight/branched and/or cyclic/acyclic alcohol having such number of carbons. The $C_1$ to $C_8$ alcohol includes, but is not limited to, methanol, ethanol, n-propanol, isopropanol, isobutanol, hexanol, and cyclohexanol.

The term $C_2$ to $C_8$ ether refers to a straight/branched and/or cyclic/acyclic ether having such number of carbons. The $C_2$ to $C_8$ ether includes, but is not limited to, dimethyl ether, diethyl ether, di-isopropyl ether, di-n-butyl ether, methyl-t-butyl ether (MTBE), tetrahydrofuran, and dioxane The term $C_3$ to $C_7$ ketone refers to a straight/branched and/or cyclic/acyclic ketone having such number of carbons. The $C_3$ to $C_7$ ketone includes, but is not limited to, acetone, methyl ethyl ketone, propanone, butanone, methyl isobutyl ketone, methyl butyl ketone, and cyclohexanone.

The term $C_3$ to $C_7$ ester refers to a straight/branched and/or cyclic/acyclic ester having such number of carbons. The $C_3$ to $C_7$ ester includes, but is not limited to, ethyl acetate, propyl acetate, n-butyl acetate, etc.

The term $C_1$ to $C_2$ chlorocarbon refers to a chlorocarbon having such number of carbons. The $C_1$ to $C_2$ chlorocarbon includes, but is not limited to, chloroform, methylene chloride (DCM), carbon tetrachloride, 1,2-dichloroethane, and tetrachloroethane.

A $C_2$ to $C_7$ nitrile refers to a nitrile have such number of carbons. The $C_2$ to $C_7$ nitrile includes, but is not limited to, acetonitrile, propionitrile, etc.

A miscellaneous solvent refers to a solvent commonly employed in organic chemistry, which includes, but is not limited to, diethylene glycol, diglyme (diethylene glycol dimethyl ether), 1,2-dimethoxy-ethane, dimethylformamide, dimethylsulfoxide, ethylene glycol, glycerin, hexamethylphsphoramide, hexamethylphosphorous triame, N-methyl-2-pyrrolidinone, nitromethane, pyridine, triethyl amine, and acetic acid.

The term $C_5$ to $C_{12}$ saturated hydrocarbon refers to a straight/branched and/or cyclic/acyclic hydrocarbon. The $C_5$ to $C_{12}$ saturated hydrocarbon includes, but is not limited to, n-pentane, petroleum ether (ligroine), n-hexane, n-heptane, cyclohexane, and cycloheptane.

The term $C_6$ to $C_{12}$ aromatic refers to substituted and unsubstituted hydrocarbons having a phenyl group as their backbone. Preferred hydrocarbons include benzene, xylene, toluene, chlorobenzene, o-xylene, m-xylene, p-xylene, xylenes, with toluene being more preferred.

The term "halo" or "halogen" as used herein, includes chloro, bromo, iodo and fluoro.

The term "blocking group" refers to a chemical group which exhibits the following characteristics. The "group" is derived from a "protecting compound." Groups that are selective for primary hydroxyls over secondary hydroxyls that can be put on under conditions consistent with the stability of the phosphoramidate (pH 2-8) and impart on the resulting product substantially different physical properties allowing for an easier separation of the 3'-phosphoramidate-5'-new group product from the unreacted desired compound. The group must react selectively in good yield to give a protected substrate that is stable to the projected reactions (see Protective Groups in Organic Synthesis, 3rd ed. T. W. Greene and P. G. M. Wuts, John Wiley & Sons, New York, N.Y., 1999). Examples of groups include, but are not limited to: benzoyl, acetyl, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl), thiopixyl (9-phenylthioxanthen-9-yl) or 9-(p-methoxyphenyl)xanthine-9-yl (MOX), etc.; C(O)-alkyl, C(O)Ph, C(O)aryl, $CH_2O$-alkyl, $CH_2O$-aryl, $SO_2$-alkyl, $SO_2$-aryl, tert-butyldimethylsilyl, tert-butyldiphenylsilyl. Acetals, such as MOM or THP and the like are exemplary groups. Fluorinated compounds are also contemplated in so far that they can be attached to the compound and can be selectively removed by passing through a fluorous solid phase extraction media (FluoroFlash™). A specific example includes a fluorinated trityl analog, 1-[4-(1H,1H,2H,2H-perfluorodecyl)phenyl)-1,1-diphenylmethanol. Other fluorinated analogs of trityl, BOC, FMOC, CBz, etc. are also contemplated. Sulfonyl chlorides like p-toluenesulfonyl chloride can react selectively on the 5' position. Esters can be formed selectively such as acetates and benzoates. Dicarboxylic anhydrides such as succinic anhydride and its derivatives can be used to generate an ester linkage with a free carboxylic acid, such examples include, but are not limited to, oxalyl, malonyl, succinyl, glutaryl, adipyl, pimelyl, superyl, azelayl, sebacyl, phthalyl, isophthalyl, terephthalyl, etc. The free carboxylic acid increases the polarity dramatically and can also be used as a handle to extract the reaction product into mildly basic aqueous phases such as sodium bicarbonate solutions. The phosphoramidate group is relatively stable in acidic media, so groups requiring acidic reaction conditions, such as, tetrahydropyranyl, could also be used.

The term "protecting group" which is derived from a "protecting compound," has its plain and ordinary meaning, i.e., at least one protecting or blocking group is bound to at least one functional group (e.g., —OH, —$NH_2$, etc.) that allows chemical modification of at least one other functional group. Examples of protecting groups, include, but are not limited to, benzoyl, acetyl, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl) group, thiopixyl (9-phenylthioxanthen-9-yl) or 9-(p-methoxyphenyl)xanthine-9-yl (MOX), etc.; C(O)-alkyl, C(O)Ph, C(O)aryl, C(O)O(lower alkyl), C(O)O(lower alkylene)aryl (e.g., —C(O)OCH$_2$Ph), C(O)O-aryl, $CH_2O$-alkyl, $CH_2O$-aryl, $SO_2$-alkyl, $SO_2$-aryl, and a protecting group comprising at least one silicon atom, such as, tert-butyldimethylsilyl, tert-butyldiphenylsilyl, Si(lower alkyl)$_2$OSi(lower alkyl)$_2$OH (such as —Si($^i$Pr)$_2$OSi($^i$Pr)$_2$OH).

The term "protecting compound," as used herein and unless otherwise defined, refers to a compound that contains a "protecting group" and that is capable of reacting with a compound that contains functional groups that are capable of being protected.

The term "leaving group", as used herein, has the same meaning to the skilled artisan (Advanced Organic Chemistry: reactions, mechanisms and structure—Fourth Edition by Jerry March, John Wiley and Sons Ed.; 1992 pages 351-357) and represents a group which is part of and attached to a substrate molecule; in a reaction where the substrate molecule undergoes a displacement reaction (with for example a nucleophile), the leaving group is then displaced. Examples of leaving groups include, but are not limited to: halogen (F, Cl, Br, and I), preferably Cl, Br, or I; tosylate, mesylate, triflate, acetate, camphorsulfonate, aryloxide, and aryloxide substituted with at least one electron withdrawing group (e.g., p-nitrophenoxide, 2-chlorophenoxide, 4-chlorophenoxide, 2,4-dinitrophenoxide, pentafluorophenoxide, etc.), etc. The term "electron withdrawing group" is accorded its plain meaning here. Examples of electron withdrawing groups include, but are not limited to, a halogen, —$NO_2$, —C(O)(lower alkyl), —C(O)(aryl), —C(O)O (lower alkyl), —C(O)O(aryl), etc.

The term "basic reagent", as used herein, means a compound that is capable of deprotonating a hydroxyl group. Examples of basic reagents include, but are not limited to, a (lower alk)oxide ((lower alkyl)OM) in combination with an alcoholic solvent, where (lower alk)oxides include, but are not limited to, $MeO^-$, $EtO^-$, $^nPrO^-$, $^iPrO^-$, $^tBuO^-$, $^iAmO^-$ (iso-amyloxide), etc., and where M is an alkali metal cation, such as $Li^+$, $Na^+$, $K^+$, etc. Alcoholic solvents include (lower alkyl)OH, such as, for example, MeOH, EtOH, $^n$prOH, $^i$PrOH, $^t$BuOH, $^i$AmOH, etc. Non-alkoxy bases can also be used such as sodium hydride, sodium hexamethyldisilazane, lithium hexamethyldisilazane, lithium diisopropylamide, calcium hydride, sodium carbonate, potassium carbonate, cesium carbonate, DBU, DBN, and Grignard reagents, such as (lower alkyl)Mg(halogen), which include, but are not limited to, MeMgCl, MeMgBr, $^t$BuMgCl, $^t$BuMgBr, etc.

The term "base" embraces the term "basic reagent" and is meant to be a compound that is capable of deprotonating a proton-containing compound, i.e., a Bronsted base. In addition to the examples recited above, further examples of a base include, but are not limited to, pyridine, collidine, 2,6-(loweralkyl)-pyridine, dimethyl-aniline, imidazole, N-methyl-imidazole, pyrazole, N-methyl-pyrazole, triethylamine, di-isopropylethylamine, etc.

The term "electron-withdrawing group" is accorded its plain meaning. Examples of electron withdrawing groups include, but are not limited to, a halogen (F, Cl, Br, or I), —$NO_2$, —C(O)(lower alkyl), —C(O)(aryl), —C(O)O (lower alkyl), —C(O)O(aryl), etc.

The term "salts," as described herein, refers to a compound comprising a cation and an anion, which can produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR'''_{4-g}{}^+$, in which R''' is a $C_{1-3}$ alkyl and g is a number selected from 0, 1, 2, 3, or 4. It should be understood that all references to pharmaceutically acceptable salts include solvent addition forms (solvates) or crystal forms (polymorphs) as defined herein, of the same acid addition salt.

The term "alkyl" refers to an unbranched or branched chain, saturated, monovalent hydrocarbon residue containing 1 to 30 carbon atoms. The term "$C_1$-M alkyl" refers to an alkyl comprising 1 to M carbon atoms, where M is an integer having one of the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. In certain embodiments, the alkyl is a $C_{1-30}$ alkyl, such as $C_{1-22}$ alkyl, such as $C_{1-15}$ alkyl, such as $C_{1-9}$ alkyl, and further such as $C_{1-5}$ alkyl. The term "$C_{1-4}$ alkyl" refers to an alkyl containing 1 to 4 carbon atoms. The term "lower alkyl" denotes a straight or branched chain hydrocarbon residue comprising 1 to 6 carbon atoms. "$C_{1-20}$ alkyl" as used herein refers to an alkyl comprising 1 to 20 carbon atoms. "$C_{1-10}$ alkyl" as used herein refers to an alkyl comprising 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The term "$C_{1-10}$ haloalkyl" means a linear or branched, saturated, monovalent hydrocarbon group in which the term "alkyl" is as defined above, and in which one or more of the hydrogen atoms are replaced, identically or differently, with a halogen atom. Preferably, said halogen atom is a fluorine atom. Said $C_{1-10}$ haloalkyl, particularly a $C_{1-3}$ haloalkyl group is, for example, fluoromethyl, difluoromethyl, trifluoromethyl, 2 fluoroethyl, 2,2 difluoroethyl, 2,2,2 trifluoroethyl, pentafluoroethyl, 3,3,3 trifluoropropyl or 1,3 difluoropropan 2 yl.

The term "alkenyl" refers to an unsubstituted hydrocarbon chain radical having from 2 to 10 carbon atoms having one or two olefinic double bonds, preferably one olefinic double bond. The term "$C_{2-N}$ alkenyl" refers to an alkenyl comprising 2 to N carbon atoms, where N is an integer having one of the following values: 3, 4, 5, 6, 7, 8, 9, or 10. The term "$C_{2-10}$ alkenyl" refers to an alkenyl comprising 2 to 10 carbon atoms. The term "$C_{2-4}$ alkenyl" refers to an alkenyl comprising 2 to 4 carbon atoms. Examples include, but are not limited to, vinyl, 1-propenyl, 2-propenyl (allyl) or 2-butenyl (crotyl). Further representative alkenyl groups include, for example, an ethenyl-, prop-2-enyl-, (E)-prop-1-enyl-, (Z)-prop-1-enyl-, iso-propenyl-, but-3-enyl-, (E)-but-2-enyl-, (Z)-but-2-enyl-, (E)-but-1-enyl-, (Z)-but-1-enyl-, 2-methylprop-2-enyl-, 1-methylprop-2-enyl-, 2-methylprop-1-enyl-, (E)-1-methylprop-1-enyl-, (Z)-1-methylprop-1- enyl-, buta-1,3-dienyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, (E)-3,3-dimethylprop-1-enyl-, (Z)-3,3-dimethylprop-1-enyl-, penta-1,4-dienyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, hexa-1,5-dienyl- and 1-(1,1-dimethylethyl-)ethenyl-group. Particularly, said group is ethenyl- or prop-2-enyl-.

The term "$C_2$-$C_6$-alkynyl-" means a linear or branched, monovalent hydrocarbon group which contains one or more triple bonds, and which contains 2, 3, 4, 5 or 6 carbon atoms, preferably 2, 3 or 4 carbon atoms ("$C_2$-$C_4$-alkynyl-") or 2 or 3 carbon atoms ("$C_2$-$C_3$-alkynyl-"). Representative $C_2$-$C_6$-alkynyl-groups include, for example, ethynyl-, prop-1-ynyl-, prop-2-ynyl-, but-1-ynyl-, but-2-ynyl-, but-3-ynyl-, pent-1-ynyl-, pent-2-ynyl, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methylpent-4-ynyl-, 2-methylpent-3-ynyl-, 1-methylpent-3-ynyl-, 4-methylpent-2-ynyl-, 1-methylpent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- and 3,3-dimethylbut-1-ynyl-group. Particularly, said alkynyl-group is ethynyl-, prop-1-ynyl- or prop-2-ynyl-.

The term "lower alkoxy" means a linear or branched, saturated, monovalent group of formula ($C_1$-$C_6$-alkyl)-O—, in which the term "$C_1$-$C_6$-alkyl" is as defined above, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof.

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "aryloxide," as used herein, and unless otherwise specified, refers to substituted or unsubstituted phenoxide (PhO—), p-phenyl-phenoxide (p-Ph-PhO—), or naphthoxide, preferably the term aryloxide refers to substituted or unsubstituted phenoxide. The aryloxide group can be substituted with one or more moieties selected from among hydroxyl, F, Cl, Br, I, —C(O)(lower alkyl), —C(O)O(lower alkyl), amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "$C_3$-$C_{10}$-cycloalkyl" means a saturated mono- or bicyclic hydrocarbon ring which contains 3, 4, 5, 6, 7, 8, 9 or 10 carbon atoms ("$C_3$-$C_{10}$-cycloalkyl-"). Said $C_3$-$C_{10}$-cycloalkyl-group may be, for example, a monocyclic hydrocarbon ring, e.g., a cyclopropyl-, cyclobutyl-, cyclopentyl-, cyclohexyl- or cycloheptyl-group, or a bicyclic hydrocarbon ring, such as decalinyl-. Preferably, said hydrocarbon ring is monocyclic and contains 3, 4, 5, 6 or 7 carbon atoms ("$C_3$-$C_7$-cycloalkyl-"), e.g., a cyclopropyl-, cyclobutyl-, cyclopentyl-, cyclohexyl- or cycloheptyl-group, or 3, 4, 5 or 6 carbon atoms ("$C_3$-$C_6$-cycloalkyl-"), e.g., a cyclopropyl-, cyclobutyl-, cyclopentyl- or cyclohexyl-group.

The term "heterocyclyl" or "heterocycloalkyl" means a saturated mono- or bicyclic hydrocarbon ring which contains 3, 4, 5, 6, 7, 8 or 9 carbon atoms, and which contains 1, 2, 3 or 4 heteroatoms which may be identical or different, said heteroatoms preferably selected from phosphorous, oxygen, nitrogen or sulfur, and wherein carbon atoms and heteroatoms add up to 4, 5, 6, 7, 8, 9 or 10 ring atoms in total, it being possible for said heterocycloalkyl-group to be attached to the rest of the molecule via any one of the carbon atoms or, if present, a nitrogen atom. "Heterospirocycloalkyl-", "heterobicycloalkyl-" and "bridged heterocycloalkyl-", as defined infra, are also included within the scope of this definition.

Preferably, a 4- to 10-membered heterocycloalkyl is monocyclic and contains 3, 4, 5 or 6 carbon atoms, and one or two of the above-mentioned heteroatoms, adding up to 4, 5, 6 or 7 ring atoms in total (a "4- to 7-membered monocyclic heterocycloalkyl-"), or contains 3, 4 or 5 carbon atoms, and one or two of the above-mentioned heteroatoms, adding up to 4, 5 or 6 ring atoms in total (a "4- to 6-membered monocyclic heterocycloalkyl"), or contains 3, 4 or 5 carbon atoms, and one or two of the above-mentioned heteroatoms, adding up to 5 or 6 ring atoms in total (a "5- to 6-membered monocyclic heterocycloalkyl"); it being possible for said heterocycloalkyl-group to be attached to the rest of the molecule via any one of the carbon atoms or the nitrogen atoms, if present.

Exemplarily, without being limited thereto, said "monocyclic heterocycloalkyl", can be a 4-membered ring, a "4-membered heterocycloalkyl", such as azetidinyl or oxetanyl; or a 5-membered ring, a "5-membered heterocycloalkyl", such as tetrahydrofuranyl, dioxolinyl, pyrrolidinyl, imidazolidinyl, pyrazolidinyl- or pyrrolinyl-; or a 6-membered ring, a "6-membered heterocycloalkyl", such as tetrahydropyranyl, piperidinyl, morpholinyl, dithianyl, thiomorpholinyl or piperazinyl; or a 7-membered ring, a "7-membered heterocycloalkyl", such as azepanyl, diazepanyl or oxazepanyl, for example.

The term "heteroaryl" means a monocyclic, bicyclic or tricyclic aromatic ring system having 5, 6, 7, 8, 9, 10, 11, 12, 13 or 14 ring atoms (a "5- to 14-membered heteroaryl" group), preferably 5, 6, 9 or 10 ring atoms, and which contains 1, 2, 3 or 4 heteroatoms, which may be identical or different, said heteroatoms selected from oxygen, nitrogen and sulfur. Said heteroaryl group can be a 5-membered heteroaryl group, such as, for example, thienyl-, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridyl, pyridazinyl, pyrimidyl, pyrazinyl or triazinyl; or a benzo-fused 5-membered heteroaryl group, such as, for example, benzofuranyl, benzothienyl, benzoxazolyl, benzisoxazolyl, benzimidazolyl, benzothiazolyl, benzotriazolyl, indazolyl, indolyl or isoindolyl; or a benzo-fused 6-membered heteroaryl-group, such as, for example, quinolinyl, quinazolinyl, isoquinolinyl, cinnolinyl, phthalazinyl or quinoxalinyl; or another bicyclic group, such as, for example, indolizinyl, purinyl or pteridinyl; or a tricyclic heteroaryl group, such as, for example, carbazolyl, acridinyl or phenazinyl.

Preferably, "heteroaryl-" is a monocyclic aromatic ring system having 5 or 6 ring atoms and which contains at least one heteroatom, if more than one, they may be identical or different, said heteroatom being selected from oxygen, nitrogen and sulfur ("5- to 6-membered monocyclic heteroaryl-"), such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl, tetrazolyl, pyridyl, pyridazinyl, pyrimidyl, pyrazinyl or triazinyl.

In general, and unless otherwise mentioned, said heteroaryl groups include all the possible isomeric forms thereof, e.g., the positional isomers thereof. Thus, for some illustrative non-restricting example, the term pyridyl includes pyridin-2-yl, pyridin-3-yl and pyridin-4-yl; the term thienyl includes thien-2-yl and thien-3-yl. Furthermore, said heteroaryl groups can be attached to the rest of the molecule via any one of the carbon atoms, or, if applicable, a nitrogen atom, e.g., pyrrol-1-yl, pyrazol-1-yl or imidazol-1-yl.

In general, and unless otherwise mentioned, the heteroaryl or heteroarylene groups include all possible isomeric forms thereof, e.g., tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

When groups in the compounds according to the invention are substituted, it is possible for said groups to be mono-substituted or poly-substituted with substituent(s), unless otherwise specified. Within the scope of the present invention, the meanings of all groups which occur repeatedly are independent from one another. It is possible that groups in the compounds according to the invention are substituted with one, two, three, four or five identical or different substituents, particularly with one, two or three substituents.

The compounds of the present invention furthermore optionally contain one or more asymmetric centrers, depending upon the location and nature of the various substituents desired. It is possible that one or more asymmetric carbon atoms are present in the (R) or (S) configuration, which can result in racemic mixtures in the case of a single asymmetric center, and in diastereomeric mixtures in the case of multiple asymmetric centers.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

If only one diastereomer displays the desired biological activity, and a second disastereomer is inactive, the preferred isomer is the one which produces the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions, and other suitable methods.

In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

Further, it is possible for the compounds of the present invention to exist as tautomers. For example, any compound of the present invention which contains an pyrazol moiety as a heteroaryl group for example can exist as a 1H tautomer, or a 2H tautomer, or even a mixture in any amount of the two tautomers, namely:

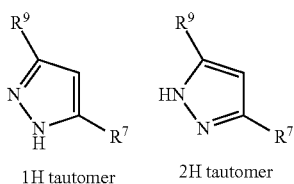

1H tautomer    2H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also includes useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention form a crystal that contains molecules of polar solvents, in particular water, methanol or ethanol, for example, as structural element of the crystal lattice of the compounds. The molecules of polar solvents, in particular water, may be present in a stoichiometric or non-stoichiometric ratio with the molecules of the compound. In the case of stoichiometric solvates, e.g., a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g., as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

Moreover, the present invention also includes prodrugs of the compounds according to the invention. The term "prodrugs" designates compounds which themselves can be biologically active or inactive, but are converted (for example metabolically or hydrolytically) into compounds according to the invention during their residence time in the body. Derivatives of the compounds disclosed herein, and the salts thereof, which are converted into a compound of formula (I), (II), or (III), or a salt thereof, in a biological system (bioprecursors or pro-drugs) are covered by the invention. Said biological system may be, for example, a mammalian organism, preferably a human subject. The bioprecursor is, for example, converted into the compound of formula (I) or a salt thereof by metabolic processes.

The term "prophylaxis" includes a use of the compound that, in a statistical sample, reduces the occurrence of the disorder or condition in the treated sample relative to an untreated control sample, or delays the onset or reduces the severity of one or more symptoms of the disorder or condition relative to the untreated control sample, when administered to prior to the onset of the disorder or condition.

The terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

"Nicotinamide", which corresponds to the following structure,

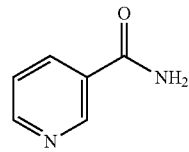

is one of the two principal forms of the B-complex vitamin niacin. The other principal form of niacin is nicotinic acid; nicotinamide, rather than nicotinic acid, however, is the major substrate for nicotinamide adenine dinucleotide (NAD) biosynthesis in mammals, as discussed in detail herein. Nicotinamide, in addition to being known as niacinamide, is also known as 3-pyridinecarboxamide, pyridine-3-carboxamide, nicotinic acid amide, vitamin B3, and vitamin PP. Nicotinamide has a molecular formula of $C_6H_6N_2O$ and its molecular weight is 122.13 Daltons. Nicotinamide is commercially available from a variety of sources.

"Nicotinamide Riboside" (NR), which corresponds to the following structure,

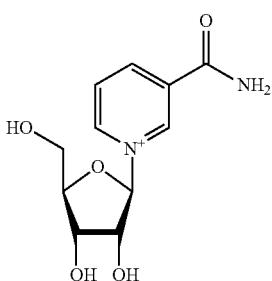

is characterized and a synthesized as described in, for instance, U.S. Pat. No. 8,106,184.

"Nicotinamide Mononucleotide" (NMN), which corresponds to the following structure,

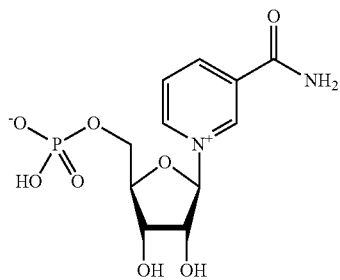

is produced from nicotinamide in the NAD biosynthesis pathway, a reaction that is catalyzed by Nampt. NMN is further converted to NAD in the NAD biosynthesis pathway, a reaction that is catalyzed by Nmnat. Nicotinamide mononucleotide (NMN) has a molecular formula of $C_{11}H_{15}N_2O_8P$ and a molecular weight of 334.22. Nicotinamide mononucleotide (NMN) is commercially available from such sources as Sigma-Aldrich (St. Louis, Mo.).

"Nicotinamide Adenine Dinucleotide" (NAD), which corresponds to the following structure,

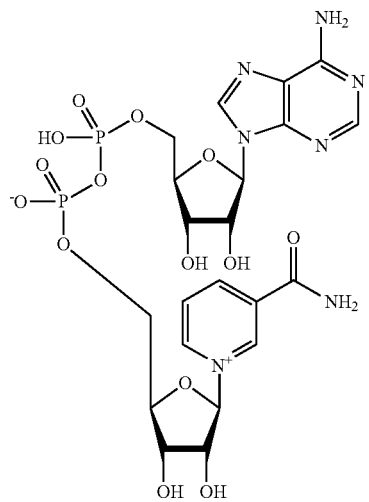

is produced from the conversion of nicotinamide to NMN, which is catalyzed by Nampt, and the subsequent conversion of NMN to NAD, which is catalyzed by Nmnat. Nicotinamide adenine dinucleotide (NAD) has a molecular formula of $C_{21}H_{27}N_7O_{14}P_2$ and a molecular weight of 663.43. Nicotinamide adenine dinucleotide (NAD) is commercially available from such sources as Sigma-Aldrich (St. Louis, Mo.).

Diseases, Disorders and Conditions

In certain embodiments, the invention relates to the use of compounds and compositions comprising one or more compounds disclosed herein that work through the nicotinamide mononucleotide adenylyltransferase (Nmnat1) pathway or other pathways of NAD+ biosynthesis which have nutritional and/or therapeutic value in improving plasma lipid profiles, prevention of stroke, and/or prolonging life and well-being. Other embodiments relate to a method for preventing or treating a disease or condition associated with the nicotinamide mononucleotide adenylyltransferase (Nmnat1) pathway or other pathways of NAD+ biosynthesis by administering a composition comprising one or more compounds disclosed herein. Diseases or conditions which typically have altered levels of NAD+ or its precursors which can be prevented or treated by supplementing a diet or therapeutic treatment regime with a composition comprising one or more compounds disclosed herein include, but are not limited to, lipid disorders, (e.g., dyslipidemia, hypercholesterolaemia or hyperlipidemia), stroke, type I and II diabetes, cardiovascular disease, and other physical problems associated with obesity.

Neurodegenerative Diseases

Axon degeneration occurs frequently in neurodegenerative diseases and peripheral neuropathies. The degeneration of transected axons is delayed in Wallerian degeneration slow (Wlds) mice with the overexpression of a fusion protein with the nicotinamide adenine dinucleotide (NAD+) synthetic enzyme, nicotinamide mononucleotide adenylyltransferase (Nmnat1). Both Wld(s) and Nmnat1 themselves are functional in preventing axon degeneration in neuronal cultures.

NAD+ levels decrease in injured, diseased, or degenerating neural cells and preventing this NAD+ decline efficiently protects neural cells from cell death. See, Araki & Milbrandt "Increased nuclear NAD+ biosynthesis and SIRT1 activation prevent axonal degeneration" Science. 2004 Aug. 13; 305(5686):1010-3 and Wang et al., "A local mechanism mediates NAD-dependent protection of axon degeneration" J Cell Biol. 170(3):349-55 (2005) hereby incorporated by reference in their entirety. As the nicotinamide mononucleotide based compounds disclosed herein are capable of increasing intracellular levels of NAD+, these compounds are useful as a therapeutic or nutritional supplement in managing injuries, diseases, and disorders affecting the central nervous system and the peripheral nervous system, including, but not limited to, trauma or injury to neural cells, diseases or conditions that harm neural cells, and neurodegenerative diseases or syndromes. The correlation of increased NAD+ synthesis with beneficial outcomes in neural injuries and diseases or conditions has been discussed in, e.g., Stein et al., "Expression of Nampt in Hippocampal and Cortical Excitatory Neurons Is Critical for Cognitive Function" The Journal of Neuroscience 2014 34(17):5800-5815; and Stein et al., "Specific ablation of Nampt in adult neural stem cells recapitulates their functional defects during aging" EMBO J. 2014 33:1321-1340.

Some neurodegenerative diseases, neurodegenerative syndromes, diseases and conditions that harm neural cells, and injury to neural cells are described below.

Essential tremor (ET) is the most common movement disorder. It is a syndrome characterized by a slowly progressive postural and/or kinetic tremor, usually affecting both upper extremities.

Parkinson's disease (PD) is a progressive neurodegenerative disorder associated with a loss of dopaminergic nigrostriatal neurons.

Alzheimer's disease (AD) is the most common form of dementia. It is a progressive degenerative disease of the brain, strongly associated with advanced age. Over time, people with the disease lose their ability to think and reason clearly, judge situations, solve problems, concentrate, remember useful information, take care of themselves, and even speak. A number of neurodegenerative diseases such as Alzheimer's disease execute their biological impact in the brain. It is preferred that nicotinamide mononucleotide based compounds disclosed herein are capable of passing the blood-brain-barrier (BBB).

Huntington's disease (HD) is an incurable, adult-onset, autosomal dominant inherited disorder associated with cell loss within a specific subset of neurons in the basal ganglia and cortex.

Ataxia is defined as an inability to maintain normal posture and smoothness of movement. Neurologic symptoms and signs such as seizures and movement disorders (e.g., dystonia, chorea) may accompany ataxia.

Catatonia is a state of apparent unresponsiveness to external stimuli in a person who is apparently awake.

Epilepsy is defined as a chronic condition characterized by spontaneous, recurrent seizures; seizure is defined as a clinical event associated with a transient, hypersynchronous neuronal discharge.

Neuroleptic malignant syndrome (NMS) refers to the combination of hyperthermia, rigidity, and autonomic dysregulation that can occur as a serious complication of the use of antipsychotic drugs.

Chorea is an involuntary abnormal movement, characterized by abrupt, brief, nonrhythmic, nonrepetitive movement of any limb, often associated with nonpatterned facial grimaces. Chorea gravidarum (CG) is the term given to chorea occurring during pregnancy.

Cortical basal ganglionic degeneration (CBGD) clinical characteristics include progressive dementia, parkinsonism, and limb apraxia. Dysfunction of the central or peripheral nervous system pathways may cause autonomic dysfunction.

Dystonia is a syndrome of sustained muscle contractions, usually producing twisting and repetitive movements or abnormal postures. Writer's cramp is a form of task-specific focal dystonia.

Mental retardation (MR) is a condition in which intellectual capacity is limited significantly. Developmental disability describes a condition that limits an individual's ability to perform activities and roles as expected in a certain social environment. Frequently, MR and developmental disabilities are present simultaneously as a consequence of brain damage.

Neuroacanthocytosis is a progressive neurologic disease characterized by movement disorders, personality changes, cognitive deterioration, axonal neuropathy, and seizures. Most patients have acanthocytosis on peripheral blood smear at some point during the course of the disease.

Pelizaeus-Merzbacher disease (PMD) and X-linked spastic paraplegia type 2 (SPG2) are at opposite ends of a clinical spectrum of X-linked diseases caused by mutations of the same gene, the proteolipid protein 1 (PLP1) gene, and resulting in defective central nervous system (CNS) myelination. Clinical signs usually include some combination of nystagmus, stridor, spastic quadriparesis, hypotonia, cognitive impairment, ataxia, tremor, and diffuse leukoencephalopathy on MRI scans.

Progressive supranuclear palsy (PSP), also known as Steele-Richardson-Olszewski syndrome, is a neurodegenerative disease that affects cognition, eye movements, and posture.

Striatonigral degeneration (SND) is a neurodegenerative disease that represents a manifestation of multiple system atrophy (MSA). The other manifestations are Shy-Drager syndrome (e.g., autonomic failure predominates) and sporadic olivopontocerebellar degeneration (sOPCA, cerebellum predominates).

Ischemic stroke occurs due to a loss of blood supply to part of the brain, initiating the ischemic cascade. Brain tissue ceases to function if deprived of oxygen for more than 60 to 90 seconds and after a few hours will suffer irreversible injury possibly leading to death of the tissue, i.e., infarction. Atherosclerosis may disrupt the blood supply by narrowing the lumen of blood vessels leading to a reduction of blood flow, by causing the formation of blood clots within the vessel, or by releasing showers of small emboli through the disintegration of atherosclerotic plaques. Embolic infarction occurs when emboli formed elsewhere in the circulatory system, typically in the heart as a consequence of atria fibriliation, or in the carotid arteries. These break off, enter the cerebral circulation, then lodge in and occlude brain blood vessels.

Due to collateral circulation within the region of brain tissue affected by ischemia, there is a spectrum of severity. Thus, part of the tissue may immediately die while other parts may only be injured and could potentially recover. The ischemia area where tissue might recover is referred to as the ischemic penumbra.

As oxygen or glucose becomes depleted in ischemic brain tissue, the production of high energy phosphate compounds such as adenine triphosphate (ATP) fails, leading to failure of energy dependent processes necessary for tissue cell survival. This sets off a series of interrelated events that result in cellular injury and death. These include the failure of mitochondria, which can lead further toward energy depletion and may trigger cell death due to apoptosis. Other processes include the loss of membrane ion pump function leading to electrolyte imbalances in brain cells. There is also the release of excitatory neurotransmitters, which have toxic effects in excessive concentrations.

Spinal cord injury, or myelopathy, is a disturbance of the spinal cord that results in loss of sensation and mobility. The two common types of spinal cord injury are: trauma: automobile accidents, falls, gunshots, diving accidents, etc. and disease: polio, spina *bifida*, tumors, Friedreich's ataxia, etc. It is important to note that the spinal cord does not have to be completely severed for there to be a loss of function. In fact, the spinal cord remains intact in most cases of spinal cord injury.

Traumatic brain injury (TBI), also called intracranial injury, or simply head injury, occurs when a sudden trauma causes brain damage. TBI can result from a closed head injury or a penetrating head injury and is one of two subsets of acquired brain injury (ABI). The other subset is non-traumatic brain injury (e.g., stroke, meningitis, anoxia). Parts of the brain that can be damaged include the cerebral hemispheres, cerebellum, and brain stem. Symptoms of a TBI can be mild, moderate, or severe, depending on the extent of the damage to the brain. Outcome can be anything from complete recovery to permanent disability or death. A coma can also affect a child's brain. The damage from TBI can be focal, confined to one area of the brain, or diffuse, involving more than one area of the brain. Diffuse trauma to the brain is frequently associated with concussion (a shaking of the brain in response to sudden motion of the head), diffuse axonal injury, or coma. Localized injuries may be associated with neurobehavioral manifestations, hemiparesis or other focal neurologic deficits.

Another insult to the brain that can cause injury is anoxia. Anoxia is a condition in which there is an absence of oxygen supply to an organ's tissues, even if there is adequate blood flow to the tissue. Hypoxia refers to a decrease in oxygen supply rather than a complete absence of oxygen, and ischemia is inadequate blood supply, as is seen in cases in which the brain swells. In any of these cases, without adequate oxygen, a biochemical cascade called the ischemic cascade is unleashed, and the cells of the brain can die within several minutes. This type of injury is often seen in near-drowning victims, in heart attack patients (particularly those who have suffered a cardiac arrest), or in people who suffer significant blood loss from other injuries that then causes a decrease in blood flow to the brain due to circulatory (hypovolemic) shock.

Regulating Blood Glucose Concentration

Provided herein is a process for regulating the concentration of blood glucose in a mammal. As utilized herein, regulating the concentration of blood glucose refers to any increase, decrease, and/or maintenance in or of the concentration of blood glucose as compared to a previously determined level.

Compounds of the present invention may be administered to a mammal in need of such treatment. For example, the mammal may require an increase in blood glucose concentration. Alternatively, the mammal may require a decrease in blood glucose concentration. Or, the mammal may require maintenance of blood glucose concentration above, at, or below a particular level or within a particular range (e.g., through a series of increases and/or decreases, or through no increases or decreases). The blood glucose concentration-regulating compounds may also be administered to a mammal as a prophylactic measure; that is, the mammal is in need of treatment to prevent or delay the occurrence or onset of a medical condition such as, for example, type 1 or type 2 diabetes.

The ability to regulate the concentration of blood glucose in a mammal according to the processes described herein (e.g., by administering to a mammal a blood glucose regulating amount of a compound of the present invention may be advantageous in the treatment and/or prevention of a variety of complications, diseases, and/or illnesses. The role of increased NAD+ levels on metabolic diseases and conditions has been described in, for example, Yoshino et al., "Nicotinamide mononucleotide, a key NAD+ intermediate, treats the pathophysiology of diet- and age-induced diabetes" Cell Metab. 2011 14:528-536; and Garten, et al., "Nampt: Linking NAD biology, metabolism, and cancer" Trends Endocrinol Metab. 2009 20(3):130-138. In general, the present invention may be utilized to treat a variety of acute, intermediate stage, and chronic conditions that may be affected by systemic NAD biosynthesis either directly or indirectly.

For example, the regulation of blood glucose concentration may be effective in the treatment and/or prophylaxis of such medical conditions as brain ischemia-induced hypoglycemia, hypoglycemic brain injury caused by, e.g., congenital hyperinsulinism in children, and/or other conditions that severely reduce blood glucose levels. Alternatively, the regulation of blood glucose concentration may be effective in counteracting the effects of the injection of an excessive amount of insulin, or an insufficient dietary or vitamin intake (e.g., deficiencies in vitamin B3 (niacin, which is derived from nicotinic acid and nicotinamide) can result in pellagra, the classic niacin deficiency disease, characterized by bilateral dermatitis, diarrhea, and dementia).

Further, regulation of blood glucose concentration may be effective in the treatment and/or prophylaxis of hypoglycemia, hyperglycemia, impaired glucose tolerance, impaired fasting glucose, and type 1 and type 2 diabetes.

The regulation of blood glucose concentration according to the methods described herein may also be advantageous in counteracting the effects of blood glucose concentration-decreasing drugs such as acetaminophen, alcohol, anabolic steroids, clofibrate, disopyramide, gemfibrozil, monoamine oxidase inhibitors (MAOIs), pentamidine, or sulfonylurea medications (such as glipizide, glyburide, and glimepiride).

Other conditions having a plausible connection to NAD biosynthesis, such as dementia, may also be beneficially treated and/or prevented by blood glucose regulation. See, e.g., Guest, et al., "Changes in Oxidative Damage, Inflammation and [NAD(H)] with Age in Cerebrospinal Fluid" PLOS One. January 2014 9(1): e85335.

The increase, decrease, and/or maintenance of blood glucose concentration can be quantified, for example, by percentage above, below, or in between one or more previously determined levels, or can be quantified by a particular blood glucose concentration or a range thereof.

For example, the blood glucose concentration may be increased to at least about 5% above a previously determined level; to at least about 10% above a previously determined level; to at least about 25% above a previously determined level; to at least about 50% above a previously determined level; to at least about 75% above a previously determined level; to at least about 100% above a previously determined level; to at least about 150% above a previously determined level; or to at least about 200% above a previously determined level. By way of another example, the blood glucose concentration may be decreased to at least about 5% below a previously determined level; to at least about 10% below a previously determined level; to at least about 25% below a previously determined level; to at least about 50% below a previously determined level; to at least about 75% below a previously determined level; to at least about 100% below a previously determined level; to at least about 150% below a previously determined level; or to at least about 200% below a previously determined level. By way of yet another example, the blood glucose concentration may be maintained (e.g., by a series of increases and/or decreases, or by no increases and/or decreases) at a concentration that is no more than about 50% greater or about 50% less than a previously determined level; e.g., no more than about 40% greater or about 40% less; no more than about 30% greater or about 30% less; no more than about 20% greater or about 20% less; no more than about 10% greater or about 10% less; or no more than about 5% greater or about 5% less.

Alternatively, the blood glucose concentration may be maintained (e.g., by a series of increases and/or decreases, or by no increases and/or decreases) at, above, or below a particular blood glucose concentration or within a desired range of blood glucose concentrations. For example, the blood glucose concentration may be maintained at a concentration of greater than about 60 mg/dL; greater than about 70 mg/dL; greater than about 100 mg/dL; greater than about 110 mg/dL; or greater than about 125 mg/dL. Alternatively, the blood glucose concentration may be maintained at a concentration of less than about 200 mg/dL; less than about 175 mg/dL; less than about 150 mg/dL; less than about 125 mg/dL; less than about 110 mg/dL; or less than about 100 mg/dL. By way of another example, the blood glucose concentration may be maintained at a concentration of from about 60 mg/dL to about 140 mg/dL; from about 90 mg/dL to about 130 mg/dL; from about 100 mg/dL to about 125 mg/dL; or from about 110 mg/dL to about 125 mg/dL.

Drug Toxicity

In some embodiments, the invention relates to the use of a nicotinamide mononucleotide based derivative to prevent adverse effects and protect cells from toxicity.

Toxicity may be an adverse effect of radiation or external chemicals on the cells of the body. Examples of toxins are pharmaceuticals, drugs of abuse, and radiation, such as UV or X-ray light. Both radiative and chemical toxins have the potential to damage biological molecules such as DNA. This damage typically occurs by chemical reaction of the exogenous agent or its metabolites with biological molecules, or indirectly through stimulated production of reactive oxygen species (e.g., superoxide, peroxides, hydroxyl radicals). Repair systems in the cell excise and repair damage caused by toxins.

Enzymes that use NAD+ play a part in the DNA repair process. Specifically, the poly(ADP-ribose) polymerases (PARPs), particularly PARP-1, are activated by DNA strand breaks and affect DNA repair. The PARPs consume NAD+ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular NAD+, leading to cellular necrosis. The apparent sensitivity of NAD+ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. See, e.g., Fang, et al., Defective Mitophagy in XPA via PARP-1 Hyperactivation and NAD+/SIRT1 Reduction. Cell 2014 157:882-896. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of NAD+ metabolism in genotoxicity can be partially effective in improving cell survival but that other proteins that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that NAD+ metabolism is an important aspect of cell stress response pathways. For example, upregulation of NAD+ metabolism, via nicotinamide/nicotinic acid mononucleotide (NMNAT) overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated NAD+ biosynthesis, which increases the available NAD+ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

Aging/Stress

In certain embodiments, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a nicotinamide mononucleotide based derivative compound. Recent studies have demonstrated the role NAD+ plays in the aging process and in age-related diseases and conditions. See, e.g., Imai, et al., "NAD+ and sirtuins in aging and disease" Trends in Cell Biol. 2014 24(8): 464-471; and Gomes, et al. "Declining NAD+ Induces a Pseudohypoxic State Disrupting Nuclear-Mitochondrial Communication during Aging" Cell 2013 155:1624-1638.

The methods described herein may be used to increase the amount of time that cells, particularly primary cells (e.g., cells obtained from an organism, e.g., a human), may be kept alive in an ex vivo cell culture. Embryonic stem (ES) cells and pluripotent cells, and cells differentiated therefrom, may also be treated with a nicotinamide mononucleotide based or derivative compound to keep the cells, or progeny thereof, in culture for longer periods of time. Such cells can also be used for transplantation into a subject, e.g., after ex vivo modification.

In certain embodiments, cells that are intended to be preserved for long periods of time may be treated with a nicotinamide mononucleotide based derivative compound. The cells may be in suspension (e.g., blood cells, serum, biological growth media, etc.) or in tissues or organs in a subject. For example, blood collected from an individual for purposes of transfusion may be treated with a nicotinamide mononucleotide based derivative compound to preserve the blood cells for longer periods of time. Additionally, blood to be used for forensic purposes may also be preserved using a nicotinamide mononucleotide based derivative compound. Other cells that may be treated to extend their lifespan or protect against apoptosis include cells for consumption, e.g., cells from non-human mammals (such as meat) or plant cells (such as vegetables).

Nicotinamide mononucleotide based derivative compounds may also be applied during developmental and growth phases in mammals, plants, insects or microorganisms, in order to, e.g., alter, retard or accelerate the developmental and/or growth process.

In certain embodiments, nicotinamide mononucleotide based derivative compounds may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the nicotinamide mononucleotide based derivative compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a nicotinamide mononucleotide based derivative compound or may have a subset of cells/tissue treated locally with a nicotinamide mononucleotide based derivative compound.

In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In certain embodiments, cells may be treated with a nicotinamide mononucleotide based derivative compound that increases the level of NAD+ in vivo, e.g., to increase their lifespan or prevent apoptosis. For example, skin can be protected from aging (e.g., developing wrinkles, loss of elasticity, etc.) by treating skin or epithelial cells with a nicotinamide mononucleotide based derivative compound that increases the level of intracellular NAD+. In exemplary embodiments, skin is contacted with a pharmaceutical or cosmetic composition comprising a nicotinamide mononucleotide based derivative compound that increases the level of intracellular NAD+. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In other embodiments, a nicotinamide mononucleotide based derivative compound that increases the level of intracellular NAD+ may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more nicotinamide mononucleotide based derivative compounds that increase the level of intracellular NAD+ may also be used as preventive, e.g., chemopreventive, compositions. When used in a chemopreventive method, susceptible skin is treated prior to any visible condition in a particular individual.

In certain embodiments, a nicotinamide mononucleotide based derivative compound that increases the level of intracellular NAD+ may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In certain embodiments, a nicotinamide mononucleotide based derivative compound that increases the level of intracellular NAD+ may be administered to a subject in order to generally increase the lifespan of its cells and to protect its cells against stress and/or against apoptosis. Treating a subject with a compound described herein may be similar to subjecting the subject to hormesis, i.e., mild stress that is beneficial to organisms and may extend their lifespan.

A nicotinamide mononucleotide based derivative compound that increases the level of intracellular NAD+ can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

A nicotinamide mononucleotide based derivative compound that increases the level of intracellular NAD+ can also be administered to a subject suffering from an acute disease, e.g., damage to an organ or tissue, e.g., a subject suffering from stroke or myocardial infarction or a subject suffering from a spinal cord injury. A nicotinamide mononucleotide based derivative compound that increases the level of intracellular NAD+ may also be used to repair an alcoholic's liver.

Cardiovascular Disease

In certain embodiments, the invention provides methods for treating and/or preventing a cardiovascular disease by administering to a subject in need thereof a nicotinamide mononucleotide based derivative compound that increases the level of intracellular NAD+. The benefits of NAD+ in treating cardivasular diseases has been described in several studies, such as Borradaile, et al., "NAD+, Sirtuins, and Cardiovascular Disease" Current Pharmaceutical Design 2016 15(1):110-117.

Cardiovascular diseases that can be treated or prevented by a nicotinamide mononucleotide based derivative compound that increases the level of intracellular NAD+ include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems.

Yet other disorders that may be treated with a nicotinamide mononucleotide based derivative compound that increases the level of intracellular NAD+ include restenosis, e.g., following coronary intervention, and disorders relating to an abnormal level of high density and low density cholesterol.

Circadian Rhythm

The circadian clock is encoded by a transcription-translation feedback loop that synchronizes behavior and metabolism with the light-dark cycle. It has been unexpectedly discovered that both the rate-limiting enzyme in mammalian NAD+ biosynthesis, nicotinamide phosphoribosyltransferase (NAMPT), and levels of NAD+, display circadian oscillations which are regulated by the core clock machinery in mice. Inhibition of NAMPT promotes oscillation of the clock gene Per2 by releasing CLOCK:BMAL1 from suppression by SIRT1. In turn, the circadian transcription factor CLOCK binds to and up-regulates Nampt, thus completing a feedback loop involving NAMPT/NAD$^+$ and SIRT1/CLOCK:BMAL1. See, e.g., Ramsey et al., "Circadian clock feedback cycle through NAMPT-mediated NAD+ biosynthesis" Science 2009 324:651-654.

Thus, the periodic variation in NAMPT-mediated NAD+ biosynthesis suggests that it impacts physiologic cycles and possibly the sleep-wake and fasting-feeding cycle. Without being bound by a single theory, it is believed that NAD+ serves as a critical "metabolic oscillator" for the rhythmic regulation of response to environmental cues through control of SIRT1 activity. Compounds disclosed herein may be used to affect a circadian feedback loop through NAMPT-mediated NAD+ biosynthesis and/or a pathway underlying the temporal coupling of metabolic, physiologic, and circadian cycles in mammals.

The recognition of a regulatory pathway involving NAMPT/NAD+-SIRT1/CLOCK:BMAL1 has broad implications for understanding how physiologic and behavioral cycles are coordinated with the environmental light-dark cycle. For instance, during sleep, when animals are normally quiescent and fasting, the levels of NAMPT steadily increase, peaking at the beginning of the wakefulness period and coinciding with feeding. As a result of the increase in NAMPT, NAD+ rises to stimulate SIRT1, which orchestrates an appropriate metabolic response in liver involving a switch from catabolic to anabolic pathways.

In certain embodiments, the present invention provides methods for regulation of the core clock machinery (sometimes also referred to as the circadian clock) of a mammal, thereby affecting behaviors, activities, and/or biological functions that occur in or are affected by a diurnal or circadian cycle and that are regulated, at least in part, by the circadian clock. Generally, the methods involve the administration of a therapeutic or prophylactic amount of a circadian clock-regulating compound to a patient or mammal in need of regulation of the circadian clock.

The methods of treatment disclosed herein are generally directed to methods of regulating the circadian clock, thereby regulating or affecting biological functions that are regulated by (sometimes also said to be affected by, affiliated with, or mediated by) the activity of the circadian clock. Typically, these biological functions display a pattern of activity and inactivity that is generally repeated approximately every 24 hours, oscillating between "active" and "inactive" states during the 24 hour period.

Thus, the present invention provides methods of regulating the activity of the circadian clock by administering to a mammal in need thereof a circadian-clock regulating compound. Generally, the regulation of the activity of the circadian clock is the result of the regulation of CLOCK:BMAL1, which is achieved according to the present methods by regulating the activity of SIRT1. The activity of SIRT1 is generally regulated according to the present methods by administration of a circadian clock-regulating compound, and in certain embodiments, by administration of a compound that affects the NAD+ pathway. The regulation of the circadian clock thereby permits regulation of activities mediated by the circadian clock.

According to the present invention, the activity of the circadian clock may be increased, decreased, or maintained by the administration of a circadian clock-regulating compound. Accordingly, biological functions (sometimes also referred to as biological activities) that are regulated by the activity of the circadian clock may also be increased, decreased, or maintained. In addition, these biological functions may also be time shifted; that is to say, an activity that typically occurs during a particular period, such as for example, during daytime or daylight hours (sometimes also referred to as the light cycle) or during the night or nighttime hours (sometimes also referred to as the dark cycle) may be shifted such that the activity occurs during the dark or light cycle, respectively, instead.

Any of a number of biological functions that are typically affected by the activity of the circadian clock may be regulated by the methods of the present invention. Thus, the present methods may be used to treat disorders or disease states that are the result of, for example, the irregular, inadequate, or pathological function of the circadian clock. Similarly, the present methods may be used to treat disorders or symptomatology caused by exogenous factors that affect the proper function or activity of the circadian clock or that require a "resetting" of the clock. For example, administration of circadian clock-regulating compound to a patient experiencing a metabolic disorder provides therapeutic benefit not only when the patient's serum NMN or NAD level is increased, but also when an improvement is observed in the patient with respect to other disorders that accompany the metabolic disorder, like weight loss or gain. In some treatment regimens, the circadian clock-regulating compound of the invention may be administered to a patient at risk of developing a disorder as described herein or to a patient reporting one or more of the physiological symptoms of such a disorder, even though a diagnosis of a metabolic disorder may not have been made.

Examples of disorders, disease states, or symptomatology that may be treated according to the methods of the present invention include, but are not limited to, travel to or across one or more time zones, a change in work shifts, night shift work, or a change in the physical status of a mammal caused by, for example, pregnancy or administration of medications of any kind. Accordingly, the methods of the present invention may be used to treat or prevent disorders, symptoms of disorders, or symptoms caused by exogenous factors. Such disorders and symptoms may include, for example, metabolic disorders, such as improper cycling or timing of feeding and fasting cycles, hyperglycemia, hypoglycemia, or diabetes; sleep disorders, such as insomnia, advanced sleep phase syndrome, delayed sleep phase syndrome, inconsistent sleep/wake cycles, or narcolepsy or to improve wakefulness in individuals suffering from excessive sleepiness; and symptoms caused by exogenous factors, such as, travel to or across one or more time zones (jet lag), shifting into or out of daylight savings time, a change in work shifts or night shift work, pregnancy, or medications being taken for unrelated diseases or disorders.

Accordingly, in certain embodiments, the present invention is directed to a method of regulating a biological function in a mammal, the function being affected by the circadian clock. The method comprises administering a therapeutic or prophylactic (sometimes also referred to as a circadian clock-regulating) amount of a circadian clock-regulating compound to the mammal. The biological function can be, for example, any one of the biological functions described herein. In certain embodiments, the invention comprises a method of treating a metabolic disorder in a mammal and comprises administering a therapeutic or prophylactic amount of a circadian clock-regulating compound to the mammal. In other embodiments, the invention comprises a method of treating a disorder in a mammal mediated by the function of the circadian clock and comprises administering a therapeutic or prophylactic amount of a circadian clock-regulating compound to the mammal. According to any one of these embodiments, the circadian clock-regulating compound may be, for example, nicotinamide, nicotinamide mononucleotide (NMN), nicotinamide adenine dinucleotide (NAD); salts and prodrugs thereof; nicotinamide phosphoribosyltransferase (NAMPT); and combinations thereof, as described in greater detail below. In other embodiments, the circadian clock-regulating compound may be an antagonist of any one of the compounds listed above, thereby exacting an effect opposite that of nicotinamide, nicotinamide mononucleotide (NMN), nicotinamide adenine dinucleotide (NAD); salts and prodrugs thereof; nicotinamide phosphoribosyltransferase (NAMPT); and combinations thereof.

In certain embodiments, the present invention is directed to a method of regulating metabolic activity of a mammal comprising administering to the mammal a therapeutic amount of a circadian clock-regulating compound. In certain embodiments, the metabolic activity of the mammal is increased. In other embodiments, the metabolic activity is decreased. In yet other embodiments, the metabolic activity of the mammal is maintained at a desired level, thereby preventing fluctuations in activity/inactivity. In still other embodiments, the metabolic activity is caused to occur in the light cycle (as opposed to its typical occurrence in the dark cycle). In other embodiments, the metabolic activity is caused to occur in the dark cycle (as opposed to its typical occurrence in the light cycle). In certain embodiments, the circadian clock-regulating compound is administered to the mammal in order to increase the anabolic activity of the liver (e.g., increase the activity of the metabolic pathways of the liver or shift or switch liver activity from catabolism to anabolism). In other embodiments, the circadian clock-regulating compound is administered to the mammal in order to increase the catabolic activity of the liver (e.g., decrease the activity of the metabolic process).

Mitochondrial Diseases and Metabolic Effects

In addition to regulating circadian rhythms and protect neural cells from cell death, sirtuins such as SIRT3, SIRT4, and SIRT5 are found in mitochondria. SIRT3 is expressed at high levels in metabolically active tissue. Modulation of SIRT3 has a variety of physiological applications for muscle cells including mimicking calorie restriction or exercise, increasing mitochodrial biogenesis or metabolism, sensitizing a cell to glucose uptake, increasing fatty acid oxidation, and decreasing reactive oxygen species. In addition, SIRT3 is demonstrated herein to be involved in promoting cell survival during genotoxic stress. Thus modulation of SIRT3 levels also has applications in mediating cell survival.

Increasing the protein or activity level of SIRT3 in a muscle cell can mimic the benefits of calorie restriction or exercise. In some embodiments, the invention relates to methods for increasing mitochondrial biogenesis or metabolism or for boosting mitochondrial activity/endurance in a muscle cell by contacting a muscle cell with an agent IS that increases the protein or activity level of SIRT3 in the cell. In some embodiments, the invention relates to methods for sensitizing a muscle cell to glucose uptake by contacting a muscle cell with an agent that increases the protein or activity level of SIRT3 in the cell. Further embodiments of the invention relate to methods for increasing fatty acid oxidation in a muscle cell by contacting a muscle cell with an agent that increases the protein or activity level of SIRT3 in the cell. Some embodiments of the invention relate to methods for decreasing reactive oxygen species (ROS) in a muscle cell by contacting the muscle cell with an agent that increases the protein or activity level of SIRT3 in the cell.

Increasing levels of SIRT3 benefits many diseases and disorders affected by metabolism within mitochondria. Increasing SIRT3 may be useful in any subjects in need of metabolic activation of one or more of their muscles, e.g., smooth muscles or cardiac muscles or muscle cells thereof. A subject may be a subject having cachexia or muscle wasting.

Increasing SIRT3 may also be used to increase or maintain body temperature, e.g., in hypothermic subjects. Alternatively, inhibiting SIRT3 may be used to reduce body temperature, e.g., in subjects having fever or hyperthermia.

Generally, activation of SIRT3 may be used to stimulate the metabolism of any type of muscle, e.g., muscles of the gut or digestive system, or the urinary tract, and thereby may be used to control gut motility, e.g., constipation, and incontinence.

Other embodiments in which it would be useful to increase SIRT3 include repair of muscle, such as after a surgery or an accident, increase of muscle mass; and increase of athletic performance.

Thus the invention provides methods in which beneficial effects are produced by contacting one or more muscle cells with an agent that increases the protein or activity level of SIRT3 in the cell. These methods effectively facilitate, increase or stimulate one or more of the following: mimic the benefits of calorie restriction or exercise in the muscle cell, increase mitochondrial biogenesis or metabolism, increase mitochondrial activity and/or endurance in the muscle cell, sensitize the muscle cell to glucose uptake, increase fatty acid oxidation in the muscle cell, decrease reactive oxygen species (ROS) in the muscle cell, increase PGC-la and/or ucp3 and/or GLUT4 expression in the muscle cell, and activate AMP activated protein kinase (AMPK) in the muscle cell.

Various types of muscle cells can be contacted in accordance with the invention. In some embodiments, the muscle cell is a skeletal muscle cell. In certain embodiments, the muscle cell is a cell of a slow-twitch muscle, such as a soleus muscle cell. The methods of the invention include, in some embodiments, administering, to a subject in need of such treatment, an agent that increases the protein or activity level of SIRT3 in cells of the subject.

The cell that is contacted or the subject that is treated in the aforementioned methods preferably is a cell in need of SIRT3 increase in protein or activity level. In certain embodiments, the cell is a diseased cell of a subject.

Also provided are methods for regulating skeletal muscle metabolism or skeletal muscle energy homeostasis in a subject. In such methods, an agent that modulates the protein or activity level of SIRT3 in the subject, i.e., the SIRT3 modulators described herein, is administered to a subject in need thereof.

Also provided are methods for increasing the protein level of SIRT3 in a muscle cell or in muscles of a subject. Such methods include subjecting a cell or a subject to caloric restriction or fasting, or administering to a subject in need thereof an agent that increases the protein or activity level of SIRT3 in a muscle cell. Diseases, disorders and conditions in which such methods are useful include mitochondrial diseases, metabolic disorders, neurologic disorders, muscular disorders, cardiovascular diseases, and excessive weight or obesity. Specific metabolic disorders, diseases or conditions include insulin resistance, diabetes, diabetes related conditions or disorders, endothelial dysfunction, non-alcoholoic fatty liver disease (NAFLD)/non-alcoholic hepatic steatosis (NASH), or metabolic syndrome. Other metabolic disorders will be known to the skilled person.

Mitochondrial diseases that can be treated include diseases that show a variety of symptoms caused by dysfunction of mitochondria in cells. The mitochondrial diseases may be classified in various ways by biochemical abnormalities, clinical symptoms or types of DNA abnormalities. Types named as KSS (chronic progressive external ophthalmoplegia), MERRF (myoclonus epilepsy associated with ragged-red fibers; Fukuhara syndrome), MELAS, Leber's disease, Leigh encephalopathia and Pearson's disease are widely known. Among them, MELAS is a type mainly showing stroke-like episodes, occupies 30% or more of the whole and is believed to be the most frequent type in the mitochondrial disease.

Retinal Diseases and Disorders

Photoreceptor neuronal cell death and vision can be rescued by NMN administration. In certain embodiments, nicotinamide phosphoribosyl transferase (NAMPT)-mediated NAD biosynthesis can play a role in for rod and/or cone PR neuron survival. In certain embodiments, decreased NAD levels can cause impaired mitochondrial function in PR neurons, alterations in TCA cycle metabolites, and can lead to cell death and blindness.

Deleting NAMPT can lead to photoreceptor death, loss of normal retinal structure and function, and vision loss. In some cases, damage to photoreceptor neurons and their function can be reversed with supplementation of NMN, an NAMPT enzymatic reaction product. Disclosed herein are methods of administering NMN to restore NAD levels in the retina. In some embodiments, NMN supplementation can be an effective therapeutic intervention for many retinal degenerative diseases.

Provided herein are methods of treating, preventing, and reducing risk of diseases associated with photoreceptor dysfunction, including, without limitation, age-related macular degeneration (AMD), inherited and acquired retinal diseases such as, without limitation, retinitis pigmentosa (RP), rod and cone dystrophism, and Leber's congenital amaurosis (LCA) by administration of NMN to a subject. In certain embodiments, NMN administration can be an effective intervention for the prevention and/or treatment of orphan retinal degenerative diseases including but not limited to rod dystrophy, cone dystrophy, retinitis pigmentosa, other inherited retinal degenerations, Leber's congenital amaurosis (LCA) and acquired retinal degenerations such as, but not limited to, age-related macular degeneration, photoreceptor degeneration following retinal detachment.

In some embodiments, these methods can comprise administering to a subject a pharmaceutically effective amount of nicotinamide mononucleotide (NMN). In some embodiments, a pharmaceutically effective amount of nicotinamide mononucleotide (NMN) can be an amount effective for increasing retinal NAD levels.

Disclosed herein are methods of treating macular degeneration in a subject. In some embodiments, the methods include treating aberrant retinal NAD levels in a subject, including aberrantly low retinal NAD levels. These methods comprise administering NMN to a subject. In some embodiments, the methods include treating retinal degeneration in a subject. In some embodiments, the methods include treating photoreceptor damage in a subject. In some embodiments, the methods include treating photoreceptor degeneration in a subject.

In some embodiments, the methods include treating vision loss associated with retinal degeneration in a subject. In some embodiments, the methods include treating aberrant retinal structure in a subject. In some embodiments, the methods include increasing retinal NAD levels in a subject.

In some embodiments, the methods include reducing the risk of developing macular degeneration in a subject. In some embodiments, the methods include reducing risk of developing aberrant retinal NAD levels in a subject. In some embodiments, the methods include reducing the risk of developing retinal degeneration in a subject. In some embodiments, the methods include reducing the risk of developing photoreceptor damage/degeneration in a subject. In some embodiments, the methods include reducing the risk of developing vision loss associated with retinal degeneration in a subject. In some embodiments, the methods include reducing the risk of developing aberrant retinal structure in a subject.

In some embodiments, the methods include treating a retina disease in a subject. In some embodiments, a retinal disease that can be treated by administration of NMN can be retinitis pigmentosa (RP), Leber's congenital amaurosis (LCA), rod dystrophy, cone dystrophy, rod-cone dystrophy, cone-rod dystrophy, age-related macular degeneration, photoreceptor degeneration following retinal detachments, or a combination thereof.

Pharmaceutical Formulations

The compounds of this invention are formulated with conventional carriers and excipients, which can be selected in accord with ordinary practice. Tablets can contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations can range from about 3 to about 11, but is ordinarily about 7 to about 10.

While it is possible for the active ingredients to be administered alone, it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets, each containing a predetermined amount of the active ingredient as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues, e.g., mouth and skin, the formulations are preferably applied as a topical ointment or cream containing the active ingredient(s) in an amount of, for example, about 0.075 to about 20% w/w (including active ingredient(s) in a range between about 0.1% and about 20% in increments of about 0.1% w/w such as about 0.6% w/w, about 0.7% w/w, etc.), preferably about 0.2 to about 15% w/w and most preferably about 0.5 to about 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When intended for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques, including microencapsulation, to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active material(s) in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia; and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally-occurring phosphatides, such as soybean lecithin; esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed, including synthetic mono- or diglycerides. In addition, fatty acids such as oleic acid may likewise be used in the preparation of injectables.

The amount of active ingredient that may be combined with the carrier material to produce a single dosage form will vary depending upon the subject treated and the particular mode of administration. For example, a time-release formulation intended for oral administration to humans may contain approximately 1 to approximately 1000 mg of active material compounded with an appropriate and convenient amount of carrier material which may vary from about 5% to about 95% of the total compositions (weight:weight). The pharmaceutical composition can be prepared to provide easily measurable amounts for administration. For example, an aqueous solution intended for intravenous infusion may contain from about 3 to about 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to about 20%, advantageously about 0.5 to about 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of about 0.1 to about 500 microns, such as about 0.5, about 1, about 30, or about 35 microns etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequent dosing or to improve the pharmacokinetic or toxicity profile of a given active ingredient.

An effective dose of an active ingredient depends at least on the nature of the condition being treated, toxicity, whether the compound is being used prophylactically (lower doses) or against an active disease or disorder, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from about 1 mg to about 1000 mg, preferably between about 5 mg and about 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with, for example, the condition of the recipient. An advantage of the compounds of this invention is that they are orally bioavailable and can be dosed orally.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

INCORPORATION BY REFERENCE

All U.S. patents and U.S. and PCT published patent applications and non-patent literature mentioned in this specification are herein incorporated by reference to the same extent as if each independent patent and publication was specifically and individually indicated to be incorporated by reference.

EXAMPLES

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the compounds and methods of the invention, and are not intended to limit the scope of what the inventor(s) regard(s) as the invention.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Unless noted otherwise, the starting materials for the synthesis described herein were obtained from commercial sources or known synthetic procedures and were used without further purification.

Analytical Methods

LC/MS data were obtained on an Agilent 1260 Infinity System, equipped with a Model 1260 ELSD and DAD and a Model 6120 Quadrupole Mass Detector. The HPLC analyses were run using either a Waters Atlantis $C_{18}$ (100×4.6 mm, 3μ 100 Å) using a gradient of 10 mM $NH_4OAc$ and methanol, or an Agilent Poroshell EC-$C_{18}$ (4.6×50 mm, 2.7μ) using a gradient of 0.1% formic acid in water and acetonitrile. NMR Spectra were obtained on a Bruker BioSpin 500 MHz Avance III Digital NMR spectrometer. Proton spectra are reported in ppm and are relative to TMS and $^{31}P$ spectra (122 MHz) are relative to 85% orthophosphoric acid as an external reference. Materials were obtained from commercial sources and were used without purification. All solvents were either HPLC-grade or anhydrous, as indicated below.

89

Example 1: 1-((2R,3R,4S)-5-(((4-(3-Chlorophenyl)-2-oxido-1,3,2-dioxaphosphinan-2-yl)oxy)methyl)-3,4-dihydroxytetrahydrofuran-2-yl)-1λ⁴-pyridine-3-carboxamide Trifluoroacetate salt (Compound 1)

Example 1A: (3-carbamoyl-1-(6-(hydroxymethyl)-2,2-dimethyltetrahydrofuro[3,4-d][1,3]dioxol-4-yl)pyridin-1-ium triflate salt)

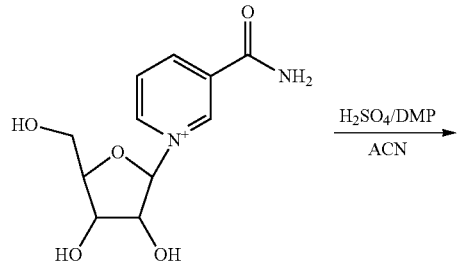

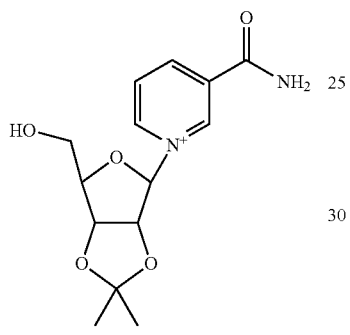

A 500 mL 3-necked flask, under nitrogen, was charged with 110 mL ACN. The solvent was cooled on ice to 0-5° C. and treated with 1.2 mL sulfuric acid. After 5 minutes, the solution was treated with 28 gm (269 mmol) 2,2-dimethoxypropane. Next, the solution was treated with 13.65 gm (33.7 mmol) nicotinamide riboside triflate salt (Sauve et al., WO 2007/061798) and the reaction was allowed to warm to room temperature and monitored by LC. After 20 minutes, the dark solution was cooled on an ice-water bath and treated with 2.73 gm (25.7 mmol) sodium carbonate and 5 mL water. After stirring for 20 minutes, the mixture was filtered to remove any remaining solid carbonate, and the filtrate evaporated to afford 19 gm as a dark red foam. The bulk sample was dissolved in 200 mL MeOH and treated, while stirred, with 50 mL water. At this concentration, the completely dissolved material became a bit turbid. The mixture was treated with 45 gm charcoal and allowed to stand at room temperature for 2 hours. The mixture was filtered through Celite, which was washed with MeOH and the filtrate evaporated to produce a turbid liquid. The liquid was diluted with ~30 mL ACN until a clear solution was obtained, which was frozen and lyophilized to afford 11.4 gm 3-carbamoyl-1-(6-(hydroxymethyl)-2,2-dimethyltetrahydrofuro[3,4-d][1,3]dioxol-4-yl)pyridin-1-ium triflate salt, as a pale yellow solid (76%).

¹H NMR (CDCl₃): δ 9.2 (s, 1H); 8.9 (d, 1H); 8.7 (d, 1H); 8.0 (q, 1H); 6.0 (d, 1H); 4.9 (dd, 1H); 4.7 (d, 1H); 4.6 (bd s, 1H); 3.8 (dd, 1H); 3.6 (dd, 1H); 1.4 (s, 3H); 1.2 (s, 3H).

90

Example 1B: 1-((3aR,4R,6aR)-6-(hydroxymethyl)-2,2-dimethyltetrahydrofuro[3,4-d][1,3]dioxol-4-yl)-1,4-dihydropyridine-3-carboxamide

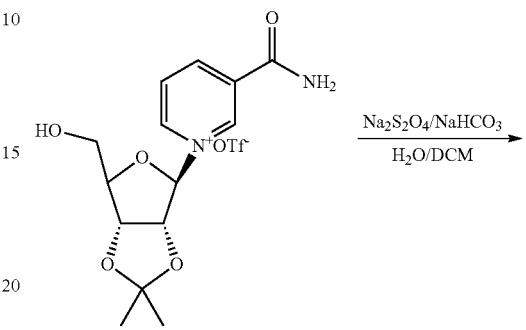

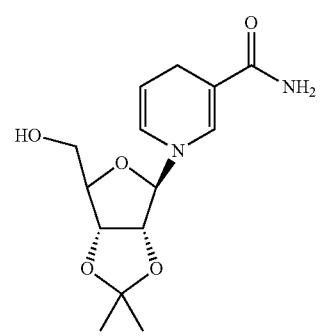

A 3 L flask was charged with a solution of 55 gm (124 mmol) 3-carbamoyl-1-(6-(hydroxymethyl)-2,2-dimethyltetrahydrofuro[3,4-d][1,3]dioxol-4-yl)pyridin-1-ium in 1 L DCM. The solution was treated with treated with 1.5 L H₂O and was degassed by bubbling argon though it for 20 minutes. The vigorously stirred mixture was cooled on an ice bath and treated with 52 gm (618 mmol) NaHCO₃, followed by 108 gm (618 mmol) sodium dithionite added in portions to control the foaming.

After the addition was complete, the mixture was allowed to warm to room temperature. After three hours, an additional 20 gm sodium dithionite was added and the reaction was stirred overnight. The two layers were separated and the aqueous layer was extracted with 250 mL DCM (2×). The combined DCM layer was dried over sodium sulfate, filtered and stripped to provide 27.3 gm of crude product. The crude material was purified via flash chromatography with a gradient of 0-6% MeOH in DCM. The pooled product fractions were evaporated to yield 9.1 gm 1-((3aR,4R,6aR)-6-(hydroxymethyl)-2,2-dimethyltetrahydrofuro[3,4-d][1,3]dioxol-4-yl)-1,4-dihydropyridine-3-carboxamide as a pale solid.

¹H NMR (CDCl₃): δ 7.2 (d, 1H); 6.0 (dd, 1H); 5.6 (bd s, 2H); 4.9 (dd, 1H); 4.8 (m, 2H); 4.6 (dd, 1H); 1.6 (s, 3H); 1.4 (s, 3H).

Example 1C: 1-((3aR,4R,6aR)-6-(((4-(3-chlorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide

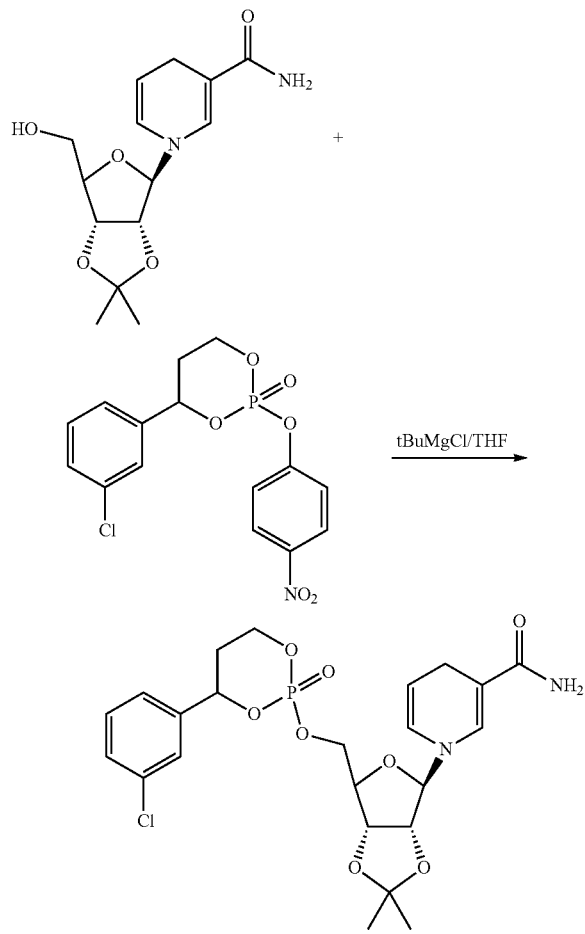

A 250 mL round bottom flask was placed under an inert atmosphere with argon and charged with 2 gm (6.75 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide. Under argon, the acetonide was dissolved in 75 mL dry DMF and treated with 10.1 mL tert-butylmagnesium chloride (10.1 mmol; 1M in THF) and stirred for 30 minutes. The reaction was treated with a solution of 2.74 gm (7.42 mmol) (±)-4-(3-chlorophenyl)-2-(4-nitrophenoxy)-1,3,2-dioxaphosphinane 2-oxide (Erion, et al., JACS, 126, 5154 (2004)) in 15 mL anhydrous DMF and the reaction warmed to 45 C and stirred. The reaction was monitored by LC and was complete within 3.5 hours. The dark solution was cooled to room temperature, stripped, co-evaporated with 2×ACN and dried on high vacuum to give 7.3 gm as a dark semi-solid. This product was purified via flash chromatography on silica with a gradient of 0-10% MeOH in DCM. Pooled fractions were evaporated to dryness on high vacuum to give 1.51 gm 1-((3aR,4R,6aR)-6-(((4-(3-chlorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide as a pale yellow solid (42%).

$^1$HNMR (CDCl$_3$): δ 7.3 (m, 4H); 7.1 (s, 1H); 5.8 (t, 1H); 4.8 (t, 1H); 4.4 (m, 3H); 4.1 (m, 1H); 3.1 (d, 1H); 2.1 (m, 2H); 1.5 (s, 3H); 1.3 (s, 3H).

$^{31}$P (CDCl$_3$): −4.1 and −4.4 ppm.

MS (ES-API$^+$) m/z M=526 (M+)

Example 1D: 1-((3aR,4R,6aR)-6-(((4-(3-chlorophenyl)-2-oxido-1,3,2-dioxaphosphinan-2-yl)oxy)methyl)-2,2-dimethyltetrahydrofuro[3,4-d][1,3]dioxol-4-yl)-1λ$^4$-pyridine-3-carboxamide

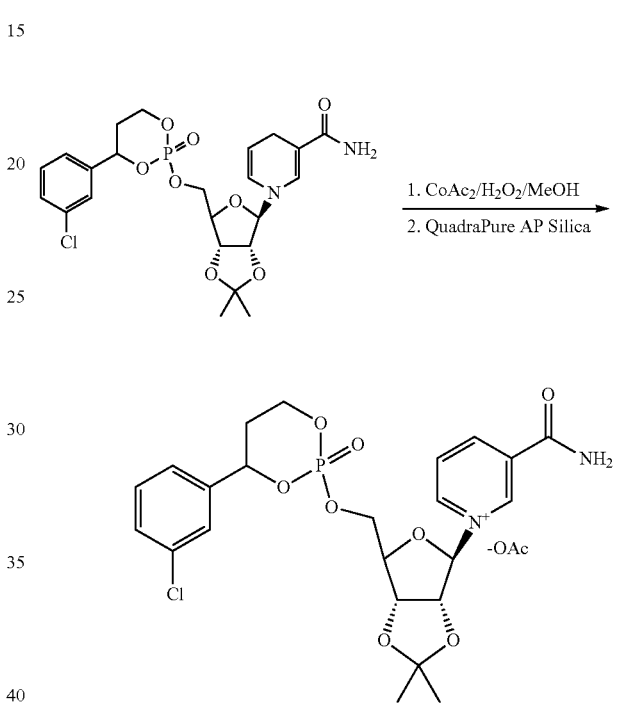

A 250 mL flask was charged with 1.5 gm (2.8 mmol) 1-((3aR,4R,6aR)-6-(((4-(3-chlorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide and dissolved in 60 mL MeOH. The solution was treated with 709 mg (2.8 mmol) CoAc$_2$·4H$_2$O and stirred to dissolve. The resulting solution was treated with 1.0 mL 30% aqueous H$_2$O$_2$ and the mixture was stirred at room temperature. The reaction was monitored by HPLC and was virtually complete after 90 minutes. The mixture was treated with an additional 50 μL hydrogen peroxide and the reaction was complete after 3.5 hours. The solution was treated with 7.5 gm QuadraSil AP resin and 5 mL water and stirred at room temperature for 45 minutes. The resin was filtered and washed with 75 mL 2:1 MeOH—H$_2$O. The filtrate was stripped to remove most of the MeOH, frozen and lyophilized to give 1.44 gm 1-((3aR,4R,6aR)-6-(((4-(3-chlorophenyl)-2-oxido-1,3,2-dioxaphosphinan-2-yl)oxy)methyl)-2,2-dimethyltetrahydrofuro[3,4-d][1,3]dioxol-4-yl)-1λ$^4$-pyridine-3-carboxamide as a dark semi-solid. The crude material is used directly in the next reaction. MS (ES-API$^+$) m/z=526 (M+)

Example 1E: 1-((2R,3R,4S)-5-(((4-(3-chlorophenyl)-2-oxido-1,3,2-dioxaphosphinan-2-yl)oxy)methyl)-3,4-dihydroxytetrahydrofuran-2-yl)-1λ⁴-pyridine-3-carboxamide Trifluoroacetate salt (Compound 1)

Example 2: 1-((2R,3R,4S)-5-(((4-(3,5-Difluorophenyl)-2-oxido-1,3,2-dioxaphosphinan-2-yl)oxy)methyl)-3,4-dihydroxytetrahydrofuran-2-yl)-1λ⁴-pyridine-3-carboxamide Trifluoroacetate salt (Compound 2)

Example 2A: 1-((3aR,4R,6aR)-6-(((4-(3,5-difluorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide

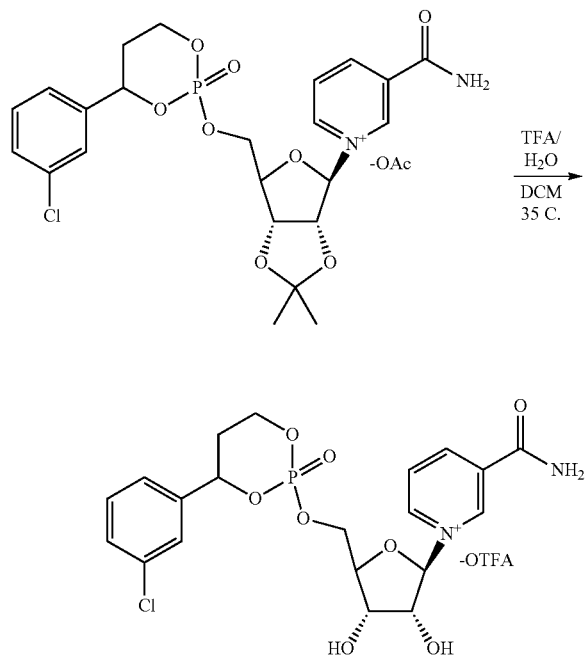

A 100 mL flask was charged with a solution of 1.44 gm 1-((3aR,4R,6aR)-6-(((4-(3-chlorophenyl)-2-oxido-1,3,2-dioxaphosphinan-2-yl)oxy)methyl)-2,2-dimethyltetrahydrofuro[3,4-d][1,3]dioxol-4-yl)-1λ⁴-pyridine-3-carboxamide acetate (2.45 mmol, 1×) in 15 mL DCM. This solution was treated with 15 mL 90% TFA/H₂O and the resulting solution stirred at 35° C. The reaction was complete after 3 hrs. The solvent was stripped and the residue is co-evaporated from 2×10 mL acetonitrile and then dried on high vacuum, to afford 1.83 gm, as a dark oil. This oil was purified on silica using 10% MeOH in DCM, containing 1% formic acid and 2% water.

The pooled product fractions were stripped and co-evaporated from 2×5 mL water to remove any residual formic acid. The residue was frozen and lyophilized to give 769 mg 1-((2R,3R,4S)-5-(((4-(3-chlorophenyl)-2-oxido-1,3,2-dioxaphosphinan-2-yl)oxy)methyl)-3,4-dihydroxytetrahydrofuran-2-yl)-1λ⁴-pyridine-3-carboxamide as the trifluoroacetic acid salt, 769 mg as a tan solid (45% 2-step yield). LC shows two peaks corresponding to the diastereomers.

¹H NMR (ACN-d₃ and D₂O): δ 9.3 (m, 1H); 9.1 (m, 1H); 8.9 (m, 1H); 7.3 (m, 4H); 6.1 (m, 1H); 5.6 (m, 1H); 4.6-4.4 (m, 5H); 2.2-1.9 (m, 2H).

³¹P (ACN-d₃ and D₂O): −3.6 and −5.3 ppm.

MS (ES-API⁺) m/z=485 (M+).

A 250 mL round bottom mask was charged with 1.1 gm (3.71 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and flushed with nitrogen. The acetonide was dissolved in 40 mL dry DMF and treated with 5.57 mL (5.57 mmol) tert-butylmagnesium chloride (1M in MeTHF) and stirred for 30 minutes, then treated with a solution of 1.59 gm (4.08 mmol) (±)-4-(3,5-difluorophenyl)-2-(4-nitrophenoxy)-1,3,2-dioxaphosphinane 2-oxide (Erion, et al., JACS, 126, 5154 (2004)) in 10 mL dry DMF. The solution was warmed to 45° C. and stirred for two hours and then at room temperature overnight. The solvent was stripped to afford an oil that is taken up in ACN and co-evaporated (3×25 mL). The residue is placed on high vacuum to give 3.73 gm 1-((3aR,4R,6aR)-6-(((4-(3,5-difluorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide as an orange solid.

¹H NMR (ACN-d₃): δ 7.0-6.9 (m, 3H); 6.9 (m, 1H); 6.0 (m, 1H); 5.6 (m, 1H); 4.9 (m, 1H); 4.75 (m, 1H); 4.70 (m, 1H); 4.3 (m, 2H); 4.07 (m, 1H); 3.0 (m, 2H); 2.3-2.2 (m, 2H); 1.5 (s, 3H); 1.3 (s, 3H).

³¹P NMR (ACN-d₃): 4.3 and −4.5 ppm

MS (ES-API⁺) m/z=529 (M+H⁺).

Example 2B: 1-((3aR,4R,6aR)-6-(((4-(3,5-Difluoro-phenyl)-2-oxido-1,3,2-dioxaphosphinan-2-yl)oxy)methyl)-2,2-dimethyltetrahydrofuro[3,4-d][1,3]dioxol-4-yl)-1λ$^4$-pyridine-3-carboxamide acetate salt

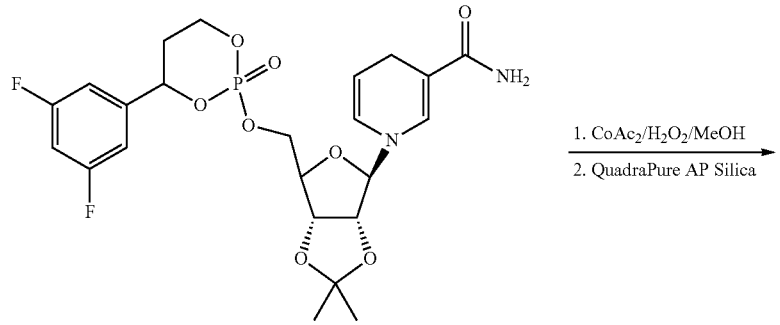

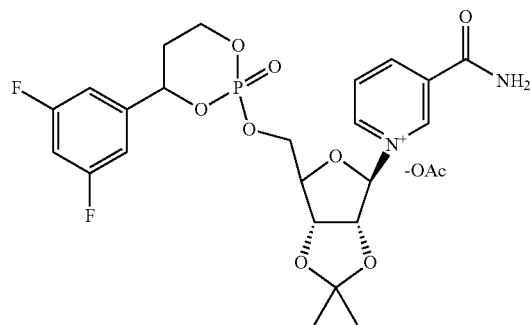

A 250 mL flask was charged 1.25 gm (2.36 mmol) 1-((3aR,4R,6aR)-6-(((4-(3,5-difluorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide and was dissolved in a solution of 589 mg (2.36 mmol) CoAc$_2$-4H$_2$O in 55 mL MeOH and cooled on an ice bath. The resulting solution is treated with 300 µL 30% aqueous H$_2$O$_2$ and the mixture stirred at 0° C. and then allowed to warm to room temperature and the reaction monitored by HPLC. After progressing ~30% in 2 hours, the dark solution was treated with an additional 300 µL peroxide, followed by another 325 µL over the next hour. The reaction is treated with 5 gm Quadrapure AP silica capture resin that is suspended in 10 mL MeOH, and 10 mL water and stirred for 45 minutes. The resin is removed by filtration and rinsed with MeOH and water, and the filtrate was frozen and lyophilized to give 1.36 gm 1-((3aR,4R,6aR)-6-(((4-(3,5-difluorophenyl)-2-oxido-1,3,2-dioxaphosphinan-2-yl)oxy)methyl)-2,2-dimethyltetrahydrofuro[3,4-d][1,3]dioxol-4-yl)-1λ$^4$-pyridine-3-carboxamide acetate salt as a dark solid. The crude product was used directly in the next reaction.

Example 2C: 1-((2R,3R,4S)-5-(((4-(3,5-Difluoro-phenyl)-2-oxido-1,3,2-dioxaphosphinan-2-yl)oxy)methyl)-3,4-dihydroxytetrahydrofuran-2-yl)-1λ$^4$-pyridine-3-carboxamide Trifluoroacetate salt (Compound 2)

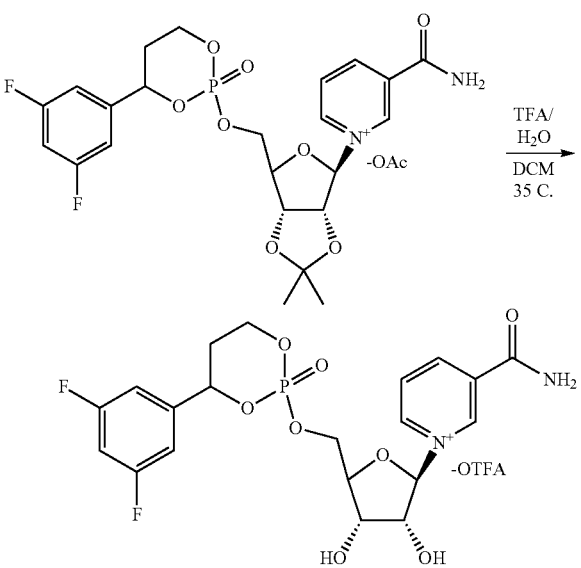

A 100 mL flask was charged with 1.38 gm (2.3 mmol) 1-((3aR,4R,6aR)-6-(((4-(3,5-difluorophenyl)-2-oxido-1,3,2-dioxaphosphinan-2-yl)oxy)methyl)-2,2-dimethyltetrahydrofuro[3,4-d][1,3]dioxol-4-yl)-1λ$^4$-pyridine-3-carboxamide acetate salt and dissolved 20 mL DCM. The solution was treated with 20 mL 90% TFA/10% H$_2$O and stirred at 35° C. for 90 minutes. The solvent is removed in vacuo and the residue co-evaporated from ACN (2×), then dried under high vacuum to give 1.78 gm as a dark solid. The solid was purified via flash chromatography using 15% MeOH in DCM, containing 2% water and 1% formic acid. The pooled product fractions were stripped to an oil and co-evaporated from water (2×) to remove residual formic acid. The product was frozen and lyophilized to give 811 mg 1-((2R,3R,4S)-5-(((4-(3,5-difluorophenyl)-2-oxido-1,3,2-dioxaphosphinan-2-yl)oxy)methyl)-3,4-dihydroxytetrahydrofuran-2-yl)-1-pyridine-3-carboxamide trifluoroacetate salt as an off-white solid (58%).

$^1$H NMR (D$_2$O): δ 9.4 (d, 1H); 9.2 (t, 1H); 8.9 (dd, 1H); 8.2 (m, 1H); 7.0 (m, 3H); 6.25 (m, 1H); 5.7 (dd, 1H); 4.7 (m, 3H); 4.5 (m, 2H); 4.4 (m, 1H); 2.4 (m, 2H).

$^{31}$P NMR (D$_2$O): −3.8 and −4.1 ppm.

MS (ES-API$^+$) m/z=487 (M+)

Example 3: S-(1-(((((5-(3-carbamoylpyridin-1(4H)-yl)-3,4-dihydroxytetrahydrofuran-2-yl)methoxy)(2-(pivaloylthio)ethoxy)phosphoryl)oxy)ethan-2-yl) 2,2-dimethylpropanethioate Trifluoroacetate salt (Compound 3)

Example 3A: S-(2-Hydroxethyl) thiopivaloate

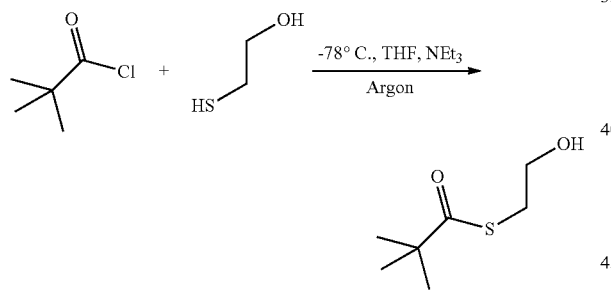

This compound was prepared in 86% yield according to the procedure of Lefebvre et al. *J. Med. Chem.* 1995, 38, 3941-3950.

Example 3B: Bis(S-pivaloyl-2-thioethyl) N,N-diisopropylphosphoramidite

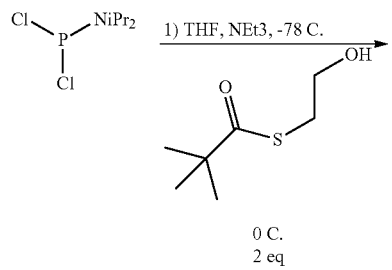

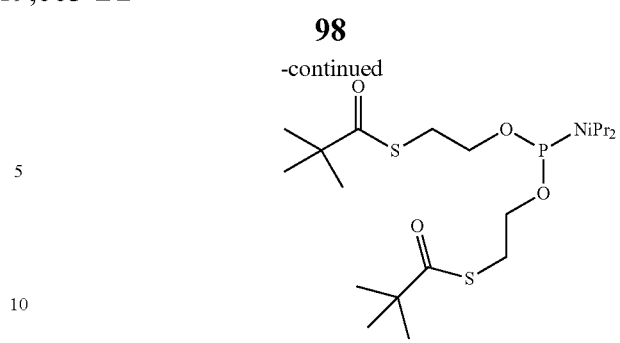

This compound was prepared according to the procedure of Lefebvre et al, *J. Med. Chem.* 1995, 38, 3941-3950. (89.6%)

Example 3C: Bis SATE (P3)NMNH Acetonide: S,S-((((((6-(3-carbamoylpyridin-1(4H)-yl)-2,2-dimethyltetrahydrofuro[3,4-d][1,3]dioxol-4-yl)methoxy)phosphanediyl)bis(oxy))bis(ethane-2,1-diyl)) bis(2,2-dimethylpropanethioate)

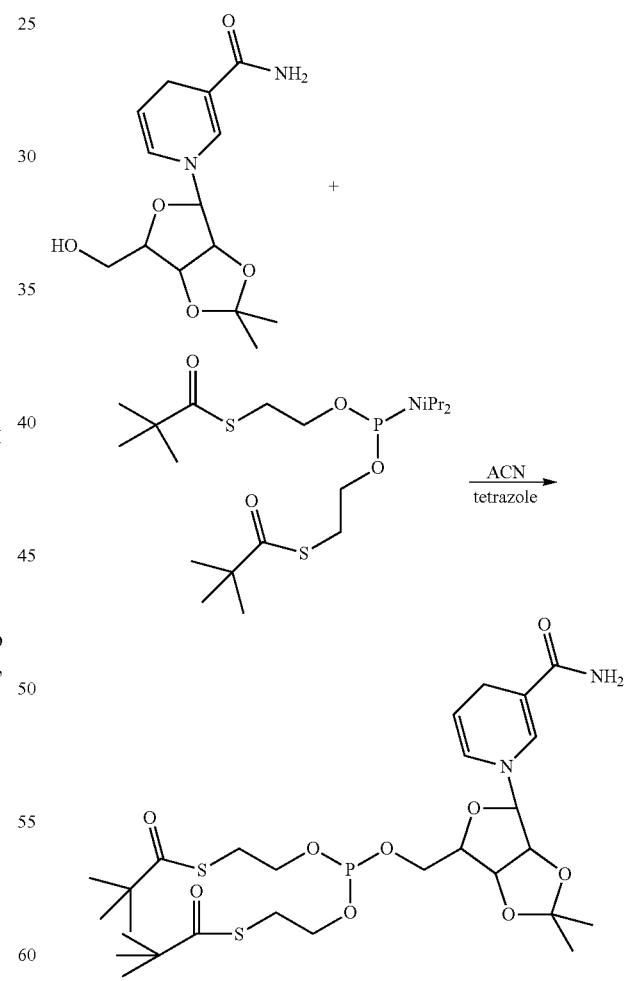

1-((3aR,4R,6aR)-6-(hydroxymethyl)-2,2-dimethyltetrahydrofuro[3,4-d][1,3]dioxol-4-yl)-1,4-dihydropyridine-3-carboxamide, prepared according to Example 1B, (0.541 g, 1.82 mmoles) in a dry 25 ml one necked round bottomed flask. Dry ACN (1 ml) was added, the solution was stirred briefly and then evaporated to provide a yellow foam. Dry ACN (5 ml) was added, stirred, then the bis(S-pivaloyl-2-thioethyl) N,N-diisopropylphosphoramidite (850 mg, 1.88 mmoles) was added. This solution was cooled to −20° C. for 5 min, then tetrazole in ACN (0.45 molar, 2.71 ml, 1.22 mmoles) was added dropwise. The cold bath was removed and the reaction allowed to warm to RT, and allowed to react overnight. Another 0.7 ml of the tetrazole solution was added and the reaction given another 1.5 hr at RT. The solvent was removed in vacuo. Saturated degassed aqueous $NaHCO_3$ (5 ml) and dichloromethane (5 ml) solutions were added. The solution was stirred vigorously, then allowed to separate. The DCM phase was dried ($Na_2SO_4$), filtered and concentrated in vacuo to give 0.610 g of a yellow glass. 52% yield.

$^1$H NMR (CDCl$_3$) ppm 7.13 (1H, m), 6.01 (1H, m), 5.30 (bs, 2H), 4.88 (m, 2H), 4.71 (m, 1H), 4.65 (m, 1H), 4.14 (m, 1H), 4.05-3.9 (m, 6H), 3.15-3.0 (m, 4H), 1.58 (s, 3H), 1.37 (s, 3H)

$^{31}$P (CD$_3$OD) 140.02 ppm.
MS(ESI+) m/z=649 (M+H)

Example 3D: Bis SATE ester (P5) NMNH Acetonide: S,S-(((((6-(3-carbamoylpyridin-1(4H)-yl)-2,2-dimethyltetrahydrofuro[3,4-d][1,3]dioxol-4-yl)methoxy)phosphordiyl)bis(oxy))bis(ethane-2,1-diyl)) bis(2,2-dimethylpropanethioate)

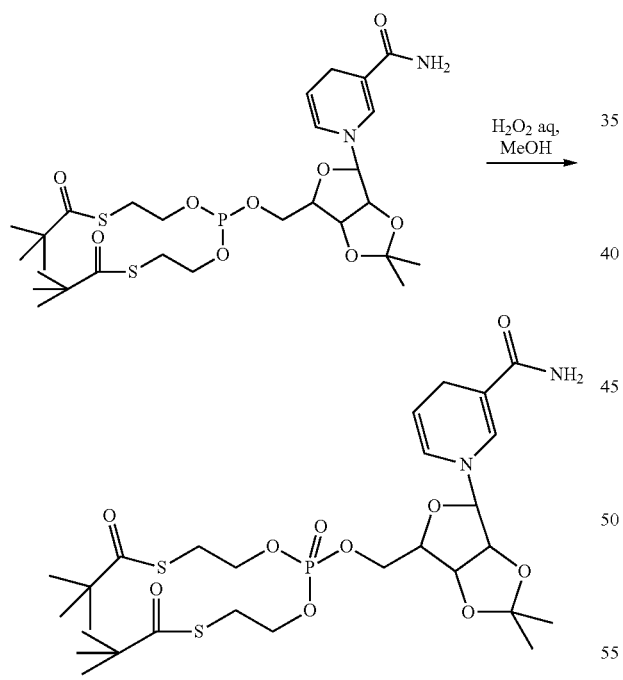

The Bis SATE (P3) NMNH Acetonide (2.19 gm, 3.38 mmoles) was dissolved in dry MeOH (7 ml) in a 50 ml 14/20 one necked round bottomed flask with a magnetic stir bar. The flask was placed into an ice/water bath and allowed to cool for 5 minutes. Hydrogen peroxide (30% solution in water) (325 μl, 358 mg, 3.18 mmoles, 0.94 eq) was added and the reaction monitored by TLC (5% MeOH/DCM). The reaction was concentrated in vacuo, dissolved in DCM, dried over $Na_2SO_4$, filtered and concentrated to give 2.71 g of a glass. This was dissolved in DCM and purified on 15 gms of silica gel (Baker), eluting with DCM (100 ml), 1% MeOH/DCM (200 ml) and 3% MeOH/DCM (200 ml). The appropriate fractions were collected to give 1.42 g (63%) of product.

$^1$H NMR (CDCl$_3$) 7.08 (bs, 1H), 5.90 (m, 1H), 5.33 (bs, 2H), 4.89-4.71 (m, 2H), 4.71-4.68 (m, 1H), 4.68-4.62 (m, 1H), 4.30-4.10 (325, 7H), 3.20-3.10 (mg, 6H), 1.56 (bs, 3H), 1.36 (bs, 3H), 1.25 (bs, 18H). $^{31}$P(CD$_3$OD) −1.01 ppm.

MS(ESI+) m/z=665 (M+H$^+$)

Example 3E: Bis SATE ester NMN Acetonide Acetate Salt: 1-(6-(((bis(2-(pivaloylthio)ethoxy) phosphoryl)oxy)methyl)-2,2-dimethyltetrahydrofuro [3,4-d][1,3]dioxol-4-yl)-3-carbamoylpyridin-1-ium acetate salt

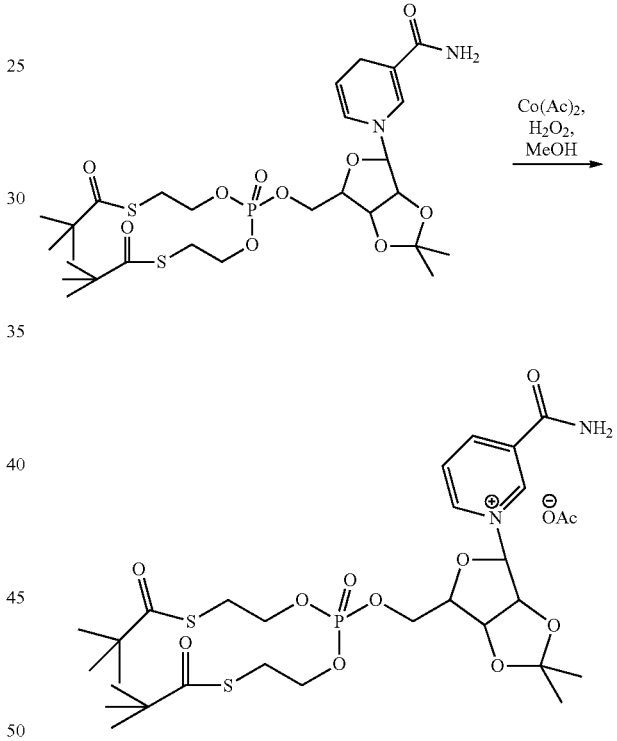

The Bis SATE ester (P5) NRH Acetonide (1.40 g, 2.10 mmoles) was placed into a 100 ml 1 necked round bottomed flask with a magnetic stir bar and placed under $N_2$. Dry MeOH (6 ml) was added via syringe to give a yellow solution. Cobalt acetate tetrahydrate (0.525 g, 2.10 mmoles) was added and the reaction was stirred to give burgundy solution. The solution was cooled in an ice/water bath, then hydrogen peroxide (30% solution, 895 mg, 8.69 mmoles, 4.14 eq) was added gradually until TLC (5% MeOH/DCM) showed complete reaction. Upon addition of the $H_2O_2$, the reaction became olive green in color. The reaction was concentrated in vacuo and dissolved in DCM. This solution was washed with water (a little sat'd NaCl solution was used to help the layers form). The DCM phase was dried over $Na_2SO_4$, filtered and concentrated to a green foam (1.41 g).

HPLC confirmed conversion of the starting material to a new entity, MS confirmed the identity.

MS(ESI+) m/z=663(M+)

This material was used directly in the Example 3F reaction.

Example 3F: Bis SATE ester NMN Trifluoroacetate Salt: 1-(5-(((bis(2-(pivaloylthio)ethoxy)phosphoryl)oxy)methyl)-3,4-dihydroxytetrahydrofuran-2-yl)-3-carbamoylpyridin-1-ium Trifluoroacetate salt (Compound 3)

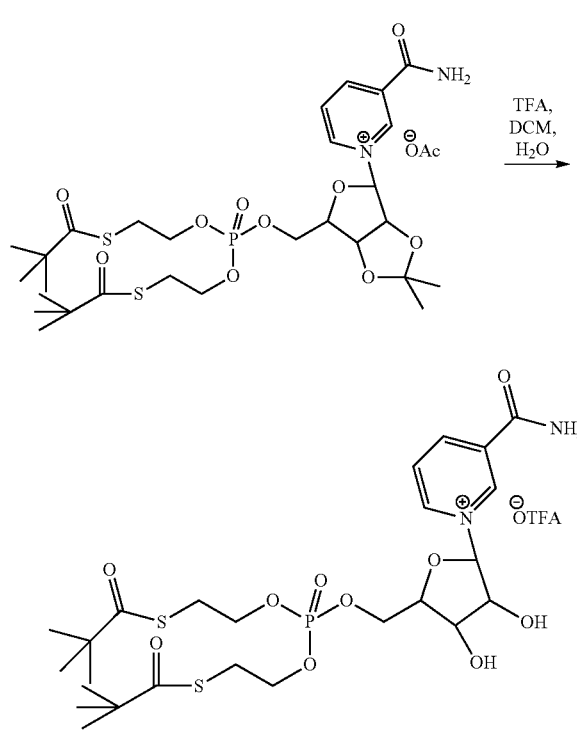

The Bis SATE ester NMN Acetonide Acetate Salt (1.41 g, 1.95 mmoles) was dissolved in 15.6 ml of trifluoroacetic acid, 17 ml of dichloromethane and 1.4 ml of water and stirred at 35° C. for 1.5 hrs. The mixture was concentrated in vacuo and co-evaporated with acetonitrile (3×). The resulting glass was dissolved in DCM and placed onto a 10 g silica gel column and eluted with DCM (100 ml), 1% MeOH/DCM (150 ml), 3% MeOH/DCM (100 ml), 10% MeOH/DCM (150 ml) then 30% MeOH/DCM (200 ml). This gave 810 mg of a colored glass which was dissolved in MeOH (+a little water) and treated with Quadra-Sil resin (5 gm) and stirred for 15 min. Filtration and washing of the resin with MeOH gave a filtrate that was concentrated in vacuo to give 758 mg of a tea colored glass.

$^1$H NMR (D$_2$O): ppm 9.38 (bs, 1H), 9.14 (bd, 1H), 8.95 (bs, 1H), 8.25 (bt, 1H), 6.21 (bd, 1H), 4.54 (m, 1H), 4.42-4.29 (m, 2H), 4.28-4.25 (m, 1H), 4.13-4.04 (bq, 4H), 1.08 (bs, 18H).

$^{31}$P (D$_2$O): 0.76 (s) ppm.

MS(ESI+) m/z=623.7 (M$^+$).

Example 4: Isopropyl ((((3S,4R,5R)-5-(3-carbamoyl-1λ$^4$-pyridin-1-yl)-3,4-dihydroxytetrahydrofuran-2-yl)methoxy)(phenoxy)phosphoryl)-L-alaninate Trifluoroacetate salt (Compound 4)

Example 4A: Isopropyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)-L-alaninate

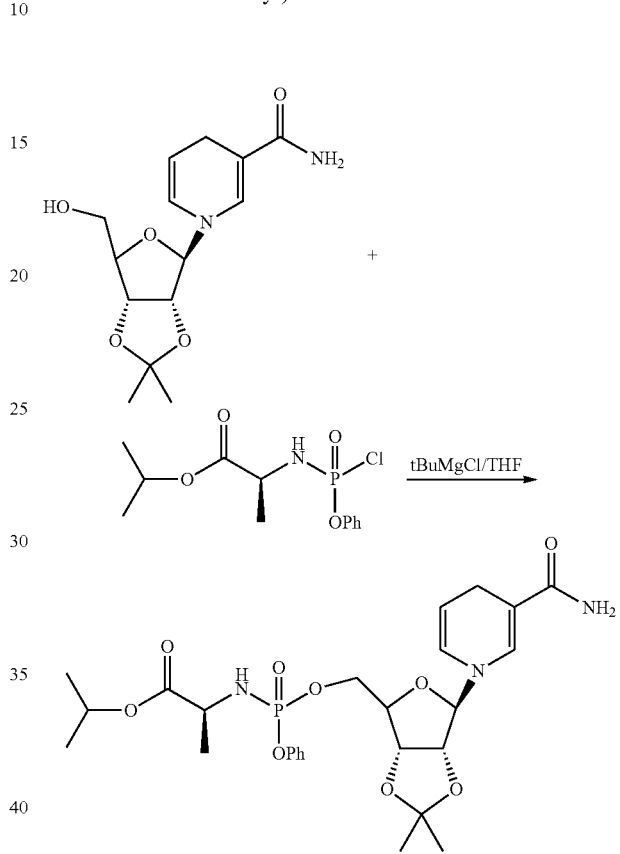

A 100 mL round bottom flask vial was charged with 1.1 gm (3.71 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and flushed with nitrogen. The compound was dissolved in 35 mL dry THF and treated with 4.45 mL (4.45 mmol) tert-butylmagnesium chloride (SAF; 1M in THF)) and the solution stirred for 30 minutes. The solution was treated via syringe with a solution of 1.36 gm isopropyl (chloro(phenoxy)phosphoryl)-L-alaninate (McGuigan, et al., J. Med. Chem., 48, 3504 (2005)) in 20 mL dry THF over a few minutes and the reaction stirred at room temperature. The reaction was allowed to stir overnight at ambient temperature. The reaction mixture was treated with ~15 mL saturated NH$_4$Cl and stripped to an oil, and the residue taken up in DCM, washed with brine and the brine back-extracted with DCM (2×). The combined organics were dried over sodium sulfate, filtered and evaporated to dryness to give 1.92 gm as a yellow foam. The foam was purified via flash chromatography with 2% MeOH in DCM. The pooled product fractions were evaporated to give 1.16 gm isopropyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)-L-alaninate as a bright yellow foam (53%).

¹H NMR (CDCl₃): δ 7.3 (m, 6H); 5.8 (m, 1H); 5.6 (s, 1H); 5.0 (m, 1H); 4.8 (d, 1H); 4.7 (m, 2H); 4.6 (m, 2H); 4.0 (m, 1H); 3.1 (m, 2H); 1.5, s, 3H); 1.4 (d, 3H); 1.3 (s, 3H); 1.2 (d, 6H).

³¹P (CDCl₃): 3.6 ppm.

MS (ES-API⁺) m/z=566 (M+H⁺)

Example 4B: Isopropyl ((((3aR,6R,6aR)-6-(3-carbamoyl-1λ4-pyridin-1-yl)-2,2-dimethyltetrahydrofuro[3,4-d][1,3]dioxol-4-yl)methoxy)(phenoxy)phosphoryl)-L-alaninate acetate salt

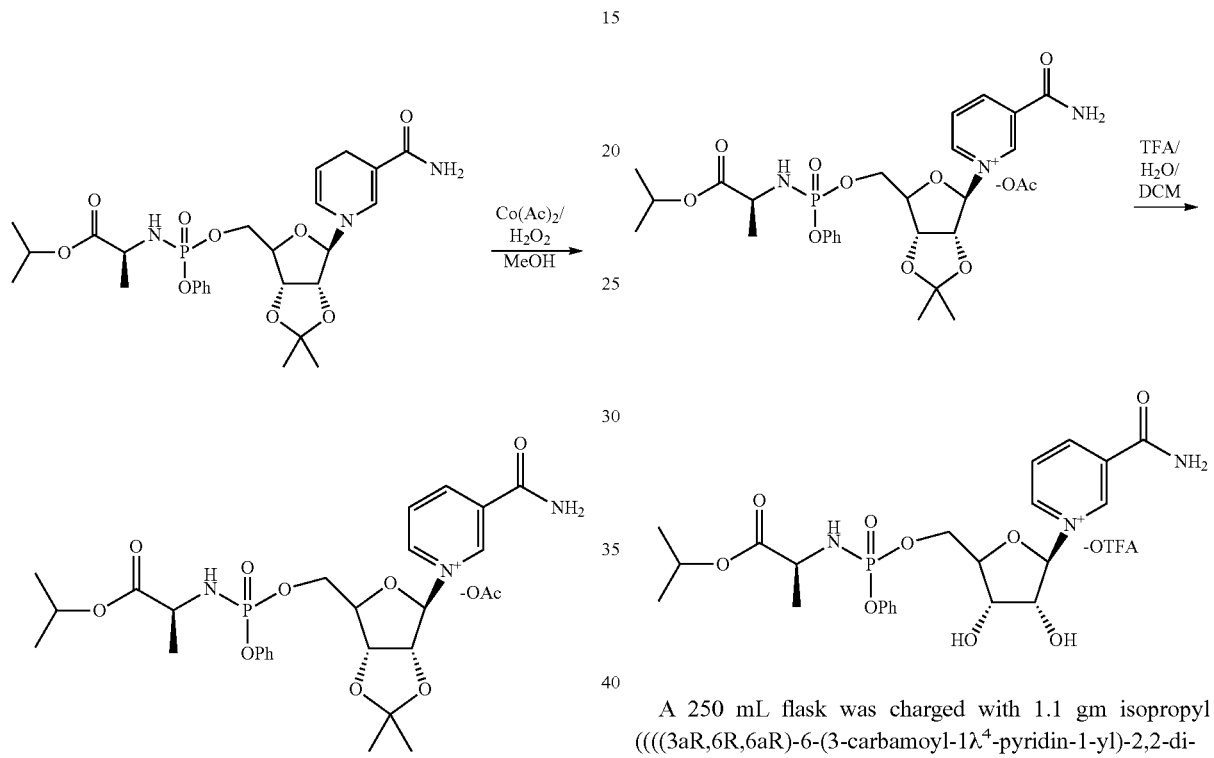

This synthesis follows the procedure described in *Monatsh für Chemie*, 134:107 (2003). A 100 mL round bottomed flask was charged with 484 mg (1.94 mmol) Co(Ac)₂—(H₂O)₄ which was dissolved in 50 mL MeOH. The red solution was cooled to 0° C. and treated with 1.1 gm (1.94 mmol) isopropyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)-L-alaninate. The resulting solution is treated with 500 µL 30% aqueous H₂O₂ and the mixture stirred at room temperature. After 2 hours, an additional 20 µL peroxide was added. The reaction was complete after a total of 4 hours. The reaction was treated with 5 gm QuadraSil AP resin suspended in 10 mL MeOH and 10 mL water and stirred at room temperature for 20 minutes, whereupon the solid was filtered and washed with MeOH and water. The filtrate was stripped to remove the MeOH and the resulting solution was frozen and lyophilized to give 1.12 gm isopropyl ((((3aR,6R,6aR)-6-(3-carbamoyl-1λ⁴-pyridin-1-yl)-2,2-dimethyltetrahydrofuro[3,4-d][1,3]dioxol-4-yl)methoxy)(phenoxy)phosphoryl)-L-alaninate acetate salt as a dark solid. The crude product is used directly in the Example 4C reaction.

MS (ES-API⁺) m/z=564 (M⁺).

Example 4C: Isopropyl ((((3S,4R,5R)-5-(3-carbamoyl-1λ4-pyridin-1-yl)-3,4-dihydroxytetrahydrofuran-2-yl)methoxy)(phenoxy)phosphoryl)-L-alaninate Trifluoroacetate salt (Compound 4)

A 250 mL flask was charged with 1.1 gm isopropyl ((((3aR,6R,6aR)-6-(3-carbamoyl-1λ⁴-pyridin-1-yl)-2,2-dimethyltetrahydrofuro[3,4-d][1,3]dioxol-4-yl)methoxy)(phenoxy) phosphoryl)-L-alaninate as the acetate salt (1.8 mmol). This material was dissolved 20 mL DCM, treated with 20 mL 90% TFA/H₂O and the resulting solution stirred at 35° C. for 90 minutes. The reaction was stripped to an oil and the residue co-evaporated with ACN (3×) to give 2 gm of red-brown oil. Purified via flash chromatography with 15% MeOH/DCM containing 1% formic acid and 2% water. Product fractions were pooled, stripped to an oil and then co-evaporated with water (2×). The remaining water was frozen and lyophilized to give 619 mg isopropyl ((((3S,4R,5R)-5-(3-carbamoyl-1λ⁴-pyridin-1-yl)-3,4-dihydroxytetrahydrofuran-2-yl)methoxy)(phenoxy)phosphoryl)-L-alaninatetrifluoroacetate as an orange solid (54%).

¹H NMR (D₂O): δ 9.3 (s, 1H); 9.1 (s, 1H); 8.7 (s, 1H); 8.2 (s, 1H); 7.3-7.0 (m, 5H); 6.2 (d, 1H); 4.9 (m, 1H); 4.7 (m, 1H); 4.6 (m, 1H); 4.4 (m, 1H); 4.2 (m, 1H); 3.9 (m, 1H); 1.6 (d, 3H); 1.2 (d, 6H).

³¹P NMR (D₂O): δ 5.4 and 5.3 ppm, in a ratio of ~2:1.

MS (ES-API⁺) m/z=526.3. (M+H⁺)

Example 5: Neopentyl ((((3S,4R,5R)-5-(3-carbamoyl-1λ4-pyridin-1-yl)-3,4-dihydroxytetrahydrofuran-2-yl)methoxy)(naphthalen-1-yloxy)phosphoryl)alaninate Trifluoroacetate salt (Compound 5)

Example 5A: Neopentyl ((((3aR,6R,6aR)-6-(3-carbamoylpyridin-1(4H)-yl)-2,2-dimethyltetrahydrofuro[3,4-d][1,3]dioxol-4-yl)methoxy)(naphthalen-1-yloxy)phosphoryl)alaninate

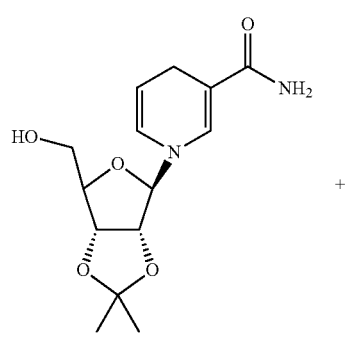

+

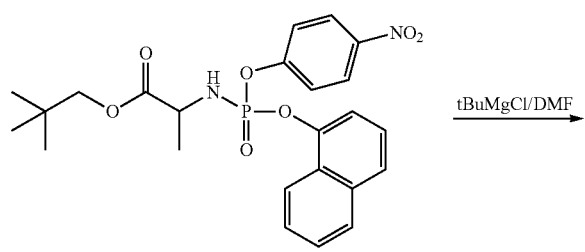

tBuMgCl/DMF →

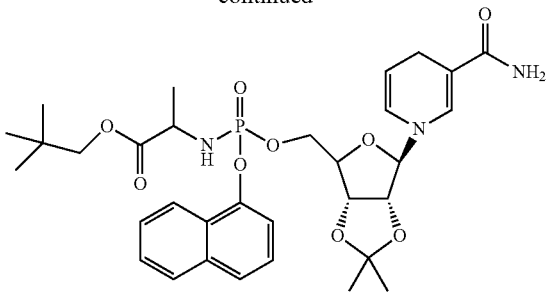

A 250 mL flask was charged with 1.73 gm (5.82 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and the flask flushed with nitrogen. This material was dissolved in 50 dry DMF and treated with 6.99 mL (6.99 mmol) tert-butylmagnesium chloride (1M in THF)). The solution was stirred for 30 minutes at room temperature, at which time it was treated with a solution of 3.4 gm (6.99 mmol) neopentyl ((naphthalen-1-yloxy)(4-nitrophenoxy)phosphoryl)alaninate (Eneroth, et al., US Patent Pub. No. 2013/0143835) in 25 mL dry DMF and the reaction was stirred at room temperature. The solvent was removed in vacuo and the residue co-evaporated from ACN (2×). The product was purified via flash chromatography with a gradient of 0-15% MeOH in DCM. The product fractions were pooled and evaporated on high vacuum to give 2.62 gm neopentyl ((((3aR,6R,6aR)-6-(3-carbamoylpyridin-1(4H)-yl)-2,2-dimethyltetrahydrofuro[3,4-d][1,3]dioxol-4-yl)methoxy)(naphthalen-1-yloxy)phosphoryl)alaninate.

$^1$HNMR (CDCl$_3$): δ 8.2-7.2 (8H); 5.7 (m, 1H); 4.9 (m, 1H); 4.5-4.1 (5H); 3.7-3.5 (4H); 3.0 (dd, 2H); 1.4-0.9 (18H).
$^{31}$P (CDCl$_3$): 4.9 and 4.2 ppm.
MS (ES-API$^+$) m/z=644 (M+).

Example 5B: Neopentyl ((((3aR,6R,6aR)-6-(3-carbamoyl-1λ4-pyridin-1-yl)-2,2-dimethyltetrahydrofuro[3,4-d][1,3]dioxol-4-yl)methoxy)(naphthalen-1-yloxy)phosphoryl)alaninate acetate salt

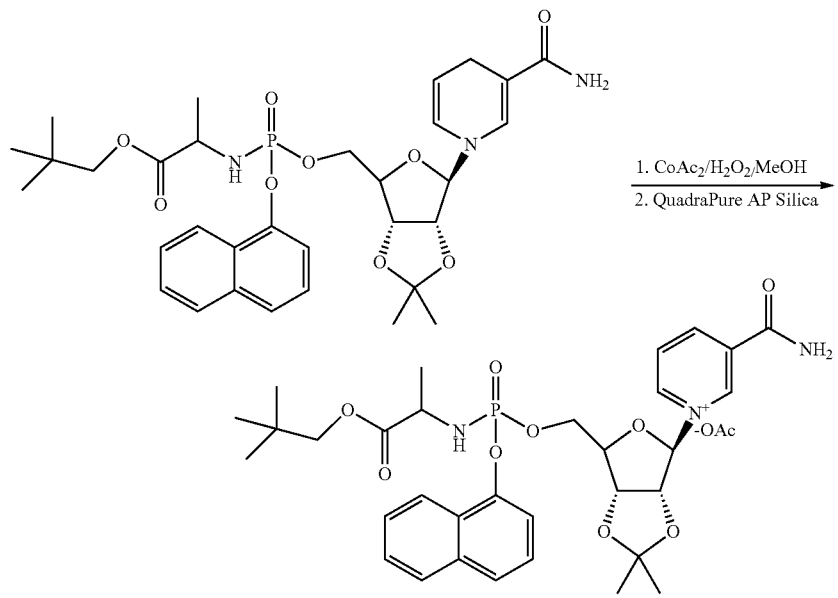

1. CoAc$_2$/H$_2$O$_2$/MeOH
2. QuadraPure AP Silica

A 250 mL flask was charged with 2.6 gm (4 mmol) neopentyl ((((3aR,6R,6aR)-6-(3-carbamoylpyridin-1(4H)-yl)-2,2-dimethyltetrahydrofuro[3,4-d][1,3]dioxol-4-yl)methoxy)(naphthalen-1-yloxy)phosphoryl)alaninate and the compound was dissolved in 100 mL MeOH. The solution was treated with 1.0 gm (4.0 mmol) CoAc$_2$·4H$_2$O in 20 mL MeOH, followed by 2 mL 30% H$_2$O$_2$ and the dark the mixture was allowed to stir at room temperature. The reaction was monitored by LC and was ~80% complete after two hours. The mixture was treated with an additional 500 μL peroxide and was complete within 30 minutes. The solution was treated with 13 gm QuadraSil AP resin and ~10 mL water and stirred for 1 hour. The resin was removed by filtration and washed with MeOH. The filtrate was concentrated on high vacuum to afford neopentyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(naphthalen-1-yloxy)phosphoryl)alaninate acetate salt as a dark solid. The crude material was used directly in the Example 5C reaction.

MS (ES-API$^+$) m/z=642 (M+).

Example 5C: Neopentyl ((((3S,4R,5R)-5-(3-carbamoyl-1λ4-pyridin-1-yl)-3,4-dihydroxytetrahydrofuran-2-yl)methoxy)(naphthalen-1-yloxy)phosphoryl)alaninate Trifluoroacetate salt (Compound 5)

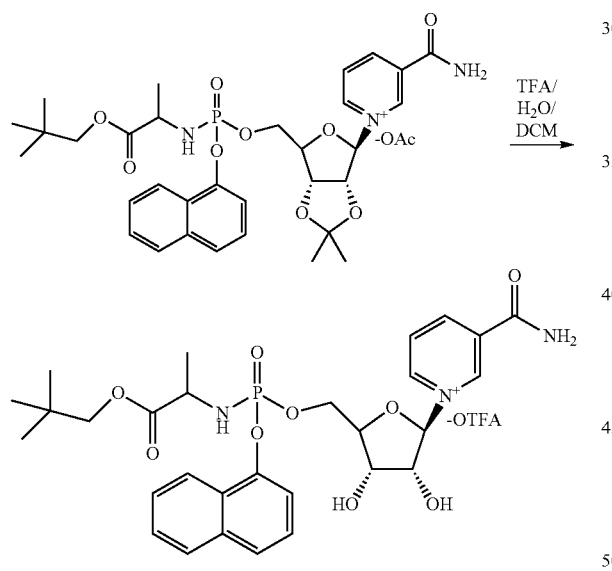

A 250 mL flask was charged with crude neopentyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(naphthalen-1-yloxy)phosphoryl)alaninate acetate salt from the Example 5B reaction and it was dissolved in 25 mL DCM. The resulting solution is treated with 25 mL 90% TFA/H$_2$O and stirred at 37° C. for 45 minutes. The solvent was stripped on high vacuum and the residue was co-evaporated with ACN (2×), diluted with water, frozen and lyophilized to give 3.5 gm of a dark oil. The oil was purified via flash chromatography with a gradient of 5-15% MeOH in DCM, containing 1% HCO$_2$H-2% H$_2$O. The pooled product fractions were stripped and then co-evaporated with water (3×) to remove the residual formic acid. The material was placed on high vacuum and evaporated to give, 1.42 gm neopentyl ((((3S,4R,5R)-5-(3-carbamoyl-1λ$^4$-pyridin-1-yl)-3,4-dihydroxytetrahydrofuran-2-yl)methoxy)(naphthalen-1-yloxy)phosphoryl)alaninate trifluoroacetate salt as a tan solid (49% 2-step yield).

$^1$H NMR (ACN-d$_3$) (For some of the proton signals, the diastereomers were clearly differentiated, as noted): δ 9.7 and 9.5 (bs s, 1H); 9.1-7.3 (12H); 6.1 and 6.0 (m, 1H); 4.9 (m, 1H); 4.5 (m, 2H); 4.3 and 4.2 (m, 2H); 3.9 (m, 1H); 3.7 (m, 2H); 1.4 and 1.3 (d, 3H); 0.9 and 0.8 (s, 9H).

$^{31}$P NMR (ACN-d$_3$) (Two diastereomers): 5.8 and 5.6 ppm.

MS (ES-API$^+$) m/z=602 (M+).

Example 6: 1-(5-((((Benzylamino)(2-(pivaloylthio)ethoxy)phosphoryl)oxy)methyl)-3,4-dihydroxytetrahydrofuran-2-yl)-3-carbamoylpyridin-1-ium Trifluoroacetate salt (Compound 6)

Example 6A: S-(2-(((Benzylamino)(4-nitrophenoxy)phosphoryl)oxy)ethyl) 2,2-dimethylpropanethioate

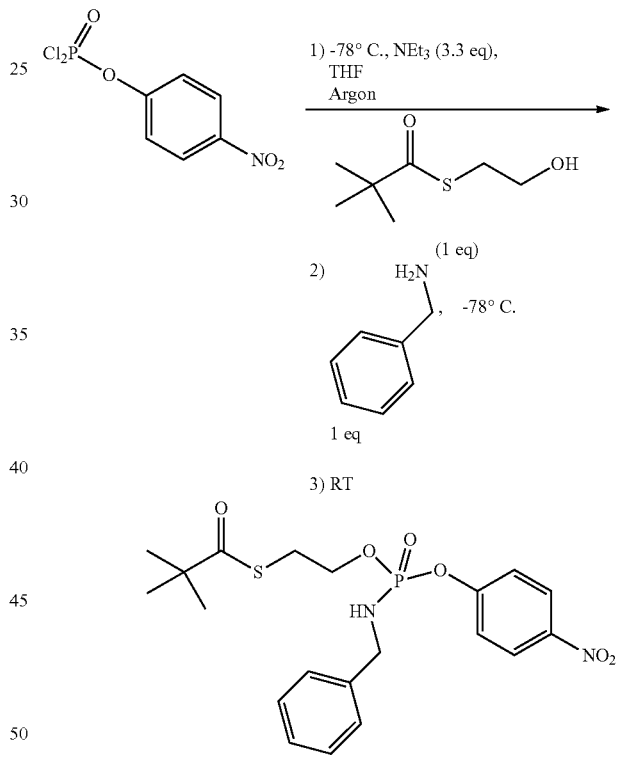

4-Nitrophenylphosphoro dichloride (2.52 g, 9.86 mmoles) was placed into a dried 100 ml single necked round bottomed flask and placed under argon. Anhydrous THF (15 ml) was added and the solution degassed and stirred, and placed under argon. The solution was placed into a dry ice/acetone bath and cooled to −78° C. Triethylamine (4.12 ml, 2.99 g, 29.6 mmols) was added dropwise to the cold solution. S-(2-hydroxyethyl) 2,2-dimethylpropanethioate (1.60 g, 9.86 mmoles) was then added dropwise to the cold reaction mixture. It was removed from the cold bath and allowed to warm to room temperature. After 30 minutes at room temperature, the reaction was again cooled to −78° C. and benzyl amine (1.07 ml, 1.06 g, 9.86 mmoles) was added dropwise. The cold bath was removed and the reaction allowed to warm to room temperature. After 1 hour at room temperature, the solvent was removed in vacuo and ethyl acetate (15 ml) was added. The resulting solution was filtered, the solid was washed with ethyl acetate (10 ml) and the filtrate was washed with water (20 ml). The layers were separated and the organic phase washed with saturated NaCl solution (10 ml) then dried over $Na_2SO_4$. The organic phase was filtered and concentrated in vacuo. The resulting oil was dissolved in dichloromethane (10 ml) and silica gel (2 g) was added to the solution. It was then filtered and the silica gel washed with more dichloromethane (20 ml). The combined solution was concentrated in vacuo to give 3.81 g (86%) of product, which was used in the next reaction.

$^1$HNMR (CDCl$_3$) ppm 8.22 (d, 2H), 7.40-7.30 (bm, 7H), 5.33 (bs, 1H), 4.28-4.16 (m, 4H), 3.85-3.65 (m, 1H), 3.25-3.14 (bt, 2H), 1.26 (bs, 3H).

$^{31}$P (CDCl$_3$) 4.52 ppm(s).

Example 6B: S-(2-(((Benzylamino)((6-(3-carbamoylpyridin-1(4H)-yl)-2,2-dimethyltetrahydrofuro[3,4-d][1,3]dioxol-4-yl)methoxy)phosphoryl)oxy)ethyl) 2,2-dimethylpropanethioate ice/water cold bath for 15 min. A 1M solution of t-butyl magnesium chloride in THF (10 ml, 10 mmols 1.2 eq) was added dropwise to the cooled solution over a 35 min period. During the addition a solid formed in the reaction. A 1 ml portion of dry DMF was added to the reaction mixture to form a homogeneous solution. This solution was stirred cold for 1.5 hrs, and gave a yellow, heterogeneous solution. S,S-((((4-nitrophenoxy)phosphordiyl) bis(oxy))bis(ethane-2,1-diyl)) bis(2,2-dimethylpropanethioate) (3.50 g, 7.74 mmoles, 0.93 eq) was dissolved in dry DMF (3 ml) and added dropwise to the cold anion solution over 10 min. The reaction became orange and homogeneous. It was removed from the cold bath and allowed to warm to room temperature, and after 30 min, the reaction was cloudy and had a green tint. The reaction was allowed to stir at room temperature for 2 hours, then concentrated in vacuo. The resulting glass was dissolved in dichloromethane and loaded onto 60 Silica gel prepared in dichloromethane. The elution solvent was as follows: DCM (150 ml), 5% MeOH/DCM

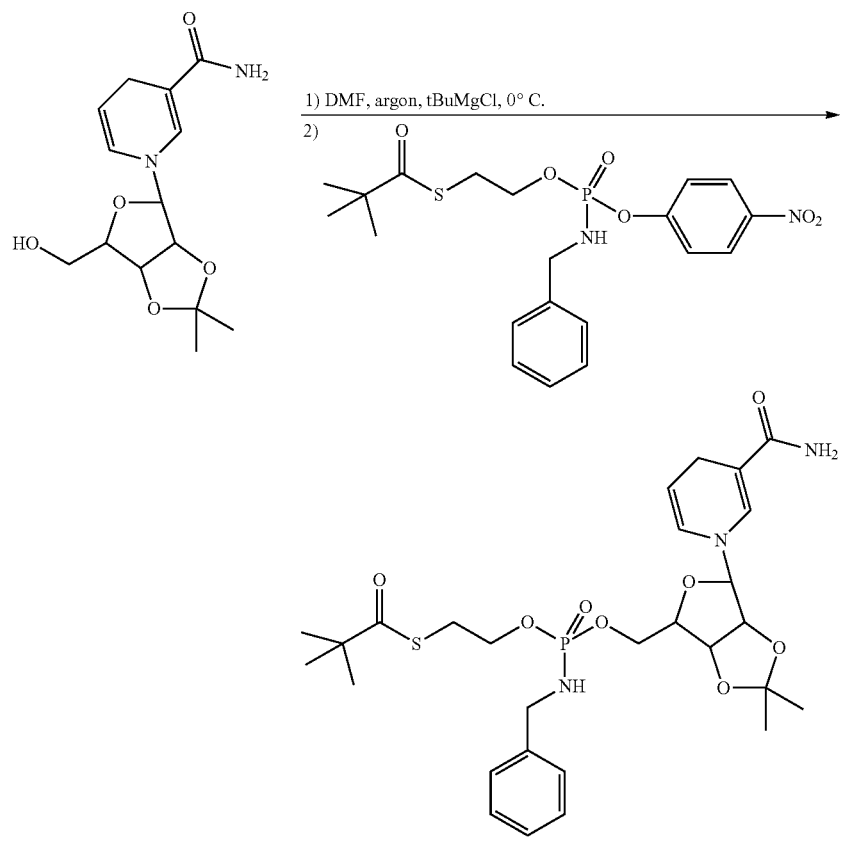

1-(6-(hydroxymethyl)-2,2-dimethyltetrahydrofuro[3,4-d][1,3]dioxol-4-yl)-1,4-dihydropyridine-3-carboxamide (2.48 g, 8.36 mmoles) was placed in a dry 100 ml single necked round bottomed flask and put under $N_2$. Anhydrous DMF (4 ml) was added via syringe and this gave a yellow solution. This solution was evacuated for 15 min to remove volatiles and traces of water, then another portion of dry DMF (11 ml) was added via syringe. This solution was placed into an (200 ml) then 10% MeOH/DCM (300 ml). This gave 3.00 g of product in 63.6% yield.

$^1$H NMR (CDCl$_3$) 7.36-7.24 (m, 6H), 7.18-7.14 (m, 1H), 5.87-5.80 (d of d, 1H), 5.51 (m, 2H), 4.84-4.67 (m, 3H), 4.55-4.47 (d of m, 1H), 4.26-3.94 (m, 8H), 3.11-3.04 (m, 4H), 1.52 (d, 3H), 1.30 (d, 3H), 1.21 (s, 9H).

$^{31}$P(CDCl$_3$) ppm, 10.74, 9.97.

MS(ESI+) m/z=610 (M+H$^+$)

Example 6C: 1-(6-((((Benzylamino)(2-(pivaloylthio)ethoxy)phosphoryl)oxy)methyl)-2,2-dimethyltetrahydrofuro[3,4-d][1,3]dioxol-4-yl)-3-carbamoylpyridin-1-ium acetate salt Example 6D: 1-(5-((((Benzylamino)(2-(pivaloylthio)ethoxy)phosphoryl)oxy)methyl)-3,4-dihydroxytetrahydrofuran-2-yl)-3-carbamoylpyridin-1-ium Trifluoroacetate salt (Compound 6)

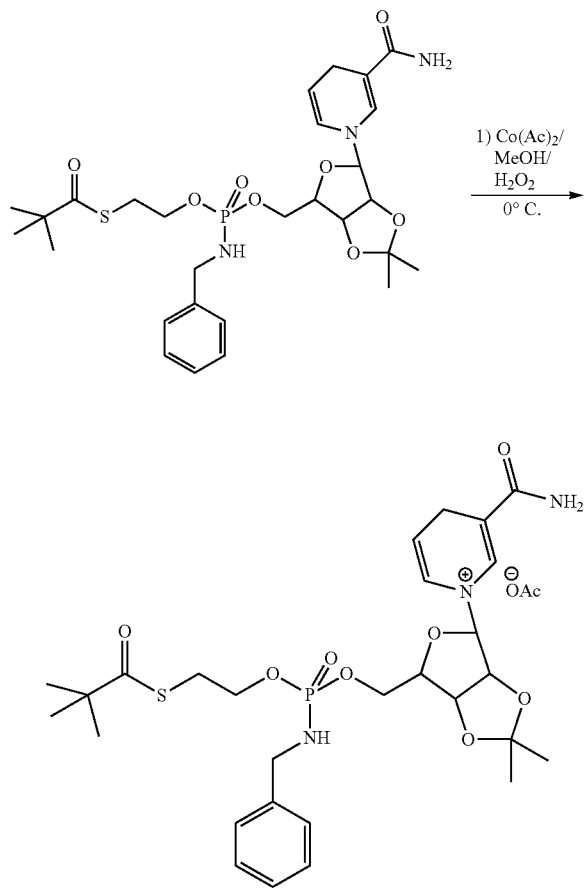 [SMILES: CC1(C)OC2C(COP(=O)(NCc3ccccc3)OCCSC(=O)C(C)(C)C)OC(N3C=CCC(C(N)=O)=C3)C2O1 ; CC1(C)OC2C(COP(=O)(NCc3ccccc3)OCCSC(=O)C(C)(C)C)OC([NH+]3C=CCC(C(N)=O)=C3)C2O1 ; "OAc"]

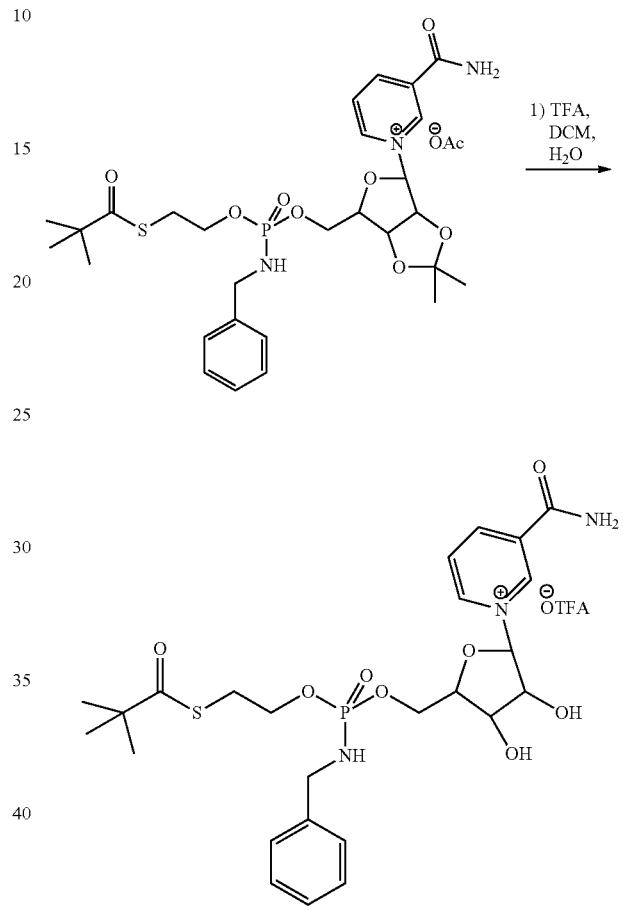

The crude S-(2-(((benzylamino)((6-(3-carbamoylpyridin-1(4H)-yl)-2,2-dimethyltetrahydrofuro[3,4-d][1,3]dioxol-4-yl)methoxy)phosphoryl)oxy)ethyl)2,2-dimethylpropanethioate (6.4 g, 10.5 mmols) was dissolved in methanol (65 ml) in a 250 ml single necked round bottomed flask with a magnetic stir bar. Cobalt acetate tetrahydrate (2.62 g, 10.5 mmoles) was added to the orange solution, giving a dark solution. The resulting homogeneous solution was cooled in an ice water bath for 10 minutes. Hydrogen peroxide (30% aqueous solution) was added dropwise to the solution giving a dark green color. The cold bath was removed. After 1 hour, HPLC showed the reaction to be finished. The reaction was concentrated in vacuo, dissolved in methanol (60 ml) and again concentrated in vacuo. Addition of another portion of methanol, followed by 33 g of QuadraSil aminopropyl resin and stirring for 1 hour gave a dark green color to the resin. The resin was filtered and washed with methanol (300 ml). The filtrate was concentrated in vacuo to give 6.2 g of a brown foam. This material was carried on without further purification. HPLC showed a single main product which was confirmed by MS analysis.

MS (ESI+) m/z=608(M+)

1-(6-((((Benzylamino)(2-(pivaloylthio)ethoxy)phosphoryl)oxy)methyl)-2,2-dimethyltetrahydrofuro[3,4-d][1,3]dioxol-4-yl)-3-carbamoylpyridin-1-ium acetate salt (6.2 g, 9.3 mmols) was dissolved in a reagent system consisting of 43 ml trifluoroacetic acid, 39 ml dichloromethane and 4 ml of water. This mixture was stirred at 35° C. for 45 minutes, when HPLC indicated that the reaction was finished. The solvents were removed in vacuo to give a glass, which was coevaporated with acetonitrile (3×50 ml). The resulting glass was dissolved in a minimum amount of dichloromethane and purified using 75 g of silica gel eluting with dichloromethane (300 ml), 1% MeOH/DCM (200 ml), 4% MeOH/DCM (400 ml), 10% MeOH/DCM (400 ml), 20% MeOH/DCM (400 ml). The appropriate fractions were collected to give 3.83 g of a rose colored foam.

1H NMR (D$_2$O) ppm: 9.30 (d, 1H), 9.03 (m, 1H), 8.89 (m, 1H), 7.42-7.17 (m, 5H), 6.13 (m, 1H), 4.53 (m, 1H), 4.34 (m, 1H), 4.20-4.11 (m, 3H), 4.04-3.96 (m, 4H), 3.04 (m, 2H).
$^{31}$P(D$_2$O) 9.68 (bs) ppm.
MS(ES-API) m/z=568(M+)

Example 7: Benzyl ((((3aR,6R,6aR)-6-(3-carbamoyl-1λ4-pyridin-1-yl)-2,2-dimethyltetrahydrofuro[3,4-d][1,3]dioxol-4-yl)methoxy)(p-tolyloxy)phosphoryl)alaninate Trifluoroacetate salt (Compound 7)

Example 7A: Benzyl ((((3aR,6R,6aR)-6-(3-carbamoylpyridin-1(4H)-yl)-2,2-dimethyltetrahydrofuro[3,4-d][1,3]dioxol-4-yl)methoxy)(p-tolyloxy)phosphoryl)alaninate

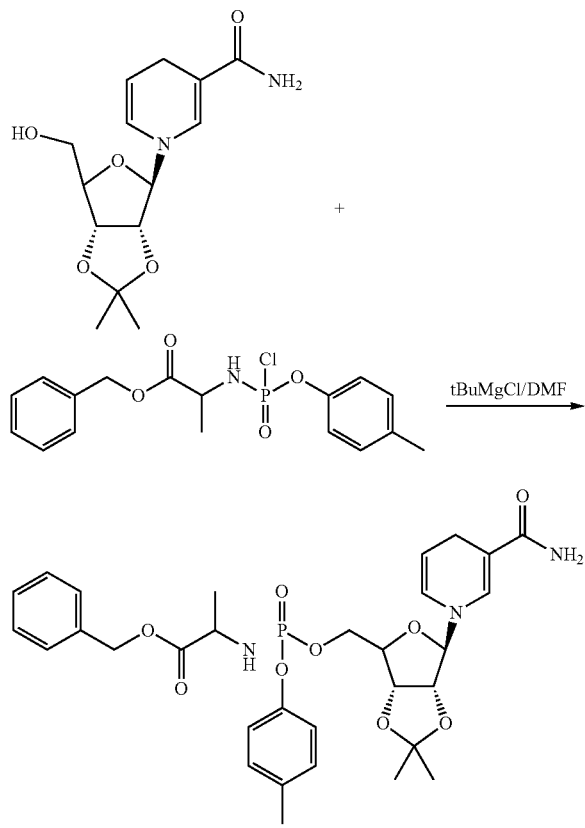

A 100 mL flask was charged with 1.75 gm (5.95 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and flushed with nitrogen. The compound was dissolved in 20 mL dry DMF and treated with 11.8 mL (11.8 mmol) tert-butylmagnesium chloride (1M in THF)) and stirred for 30 minutes. The resulting solution was treated with a solution 4.34 gm (11.8 mmol) benzyl (chloro(p-tolyloxy)phosphoryl) alaninate (McGuigan, et al., *J. Med. Chem.*, 48, 3504 (2005)) in 10 mL dry DMF and the reaction wasstirred at RT. After 90 minutes the reaction was complete, with LC/MS showing a large product peak with M+1=628. The solvent was stripped and the residue was co-evaporated with 2×ACN, then dried in vacuo to give 9.5 gm as an amber foam. The foam was pooled with a second reaction containing 3.37 mmol phosphoryl chloride starting material for purification via flash chromatography using 5% MeOH in DCM. The pooled fractions were stripped and evaporated in vacuo to give 4 gm benzyl ((((3aR,6R,6aR)-6-(3-carbamoylpyridin-1(4H)-yl)-2,2-dimethyltetrahydrofuro[3,4-d][1,3]dioxol-4-yl)methoxy)(p-tolyloxy)phosphoryl)alaninate, as a yellow oil (68%).

$^1$H NMR (ACN-d$_3$): δ 7.9 (bd s, 1H); 7.4 (m, 4H); 7.1 (m, 5H); 5.9 (m, 2H); 5.13 (s, 1H); 5.10 (d, 1H); 4.8 (dd, 1H); 4.75 (m, 1H); 4.5 (m, 1H); 4.15 (m, 1H); 4.0 (m, 1H); 3.0 (m, 2H); 2.3 (3, 3H); 1.5 (d, 3H); 1.3 (s, 3H); 1.2 (s, 3H).

$^{31}$P NMR (ACN-d$_3$): 5.1 and 5.0 ppm.

MS (ES-API$^+$) m/z=628 (M+H$^+$)

Example 7B: ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(p-tolyloxy)phosphoryl)alaninate acetate salt

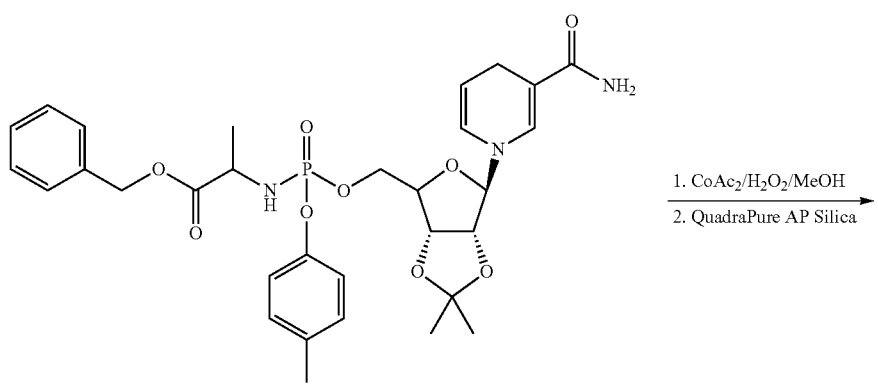

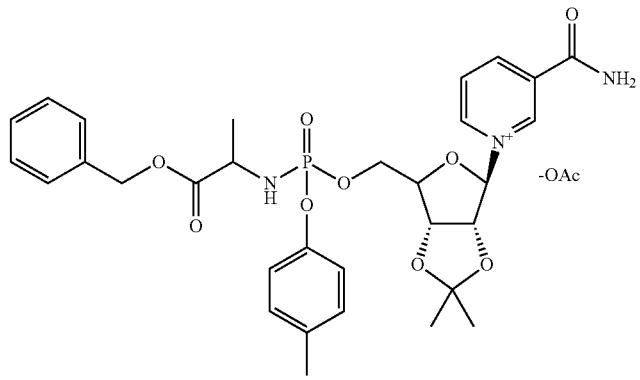

This synthesis follows the procedure described in *Monatsh für Chemie*, 134:107 (2003). A 250 mL flask was charged with 4 gm (6.4 mmol) benzyl ((((3aR,6R,6aR)-6-(3-carbamoylpyridin-1(4H)-yl)-2,2-dimethyltetrahydrofuro[3,4-d][1,3]dioxol-4-yl)methoxy)(p-tolyloxy)phosphoryl)alaninate and dissolved in 100 mL MeOH. This solution was treated with a solution of 1.89 gm (7.6 mmol) CoAc$_2$-4H$_2$O in 50 mL MeOH and then with 2.75 mL 30% H$_2$O$_2$ and the dark mixture was allowed to stir at RT. After 40 minutes, it was ~95% complete by LC. The reaction was treated with an additional 200 uL peroxide and went to completion within 30 minutes. The reaction was treated with 14 gm Quadrapure AP silica capture resin and ~5 mL water and stirred at room temperature for ~15 minutes, after which the resin was removed by filtration and washed with MeOH and water. The filtrate was evaporated to give 4 gm benzyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(p-tolyloxy)phosphoryl)alaninate acetate salt as a dark oil. LC/MS showed two peaks corresponding to the diastereomers, with MS (ES-API$^+$) m/z=626. This product was used directly in the next reaction.

Example 7C: Benzyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(p-tolyloxy)phosphoryl)alaninate Trifluoroacetate salt (Compound 7)

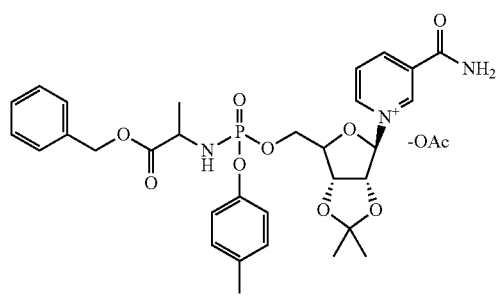

TFA/ H$_2$O
───────→
DCM/ 37

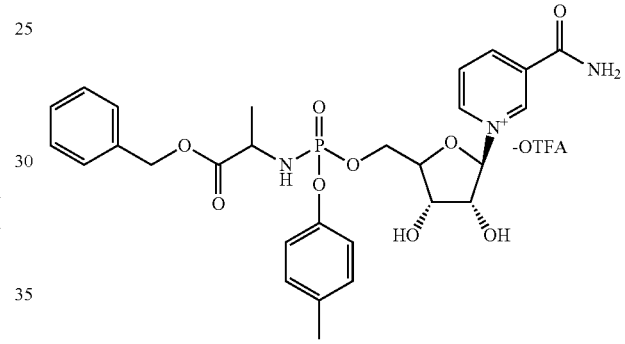

A 500 mL flask was charged with 4.0 gm benzyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(p-tolyloxy)phosphoryl)alaninate acetate salt and was dissolved in 60 mL DCM. This mixture was treated with 60 mL of 90% TFA/H$_2$O and the resulting solution was stirred at 37° C. for 45 minutes. The solvent was stripped and the residue dried on high vacuum to give 4.32 gm as a dark oil. The oil was purified via flash chromatography with 10%-15% MeOH in DCM, containing 1% HCO$_2$H and 2% H$_2$O. The pooled product fractions were stripped and co-evaporated with water (3×) to remove formic acid. The product was mixed in 9:1 water/ACN, frozen and lyophilized to give 2.1 gm benzyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(p-tolyloxy)phosphoryl)alaninate trifluoroacetate salt, as a tan solid (51%).

$^1$H NMR (ACN-d$_3$) (For many of the proton signals, the diastereomers were clearly differentiated, as noted): δ 9.6 and 9.5 (s, 1H); 9.0 (m, 1H); 8.8 (m, 1H); 8.4 (m, 1H); 8.0 (m, 1H); 7.3 (m, 5H); 7.0 (m, 4H); 6.1 and 6.0 (d, 1H); 5.1 (s, 2H); 4.7 (q, 1H); 4.3-4.0 (m, 5H); 2.3 and 2.2 (s, 3H); 1.4 and 1.3 (d, 3H).

$^{31}$P NMR (ACN-d$_3$): 5.3 and 5.2 ppm.

MS (ES-API$^+$) m/z=586 (M$^+$).

Example 8: 1-((2R,3R,4S)-5-(((((1-(Benzyloxy)-1-oxopropan-2-yl)amino)(naphthalen-1-yloxy)phosphoryl)oxy)methyl)-3,4-dihydroxytetrahydrofuran-2-yl)-3-carbamoylpyridin-1-ium Trifluoroacetate salt (Compound 8)

Example 8A: Benzyl ((((3aR,6R,6aR)-6-(3-carbamoylpyridin-1(4H)-yl)-2,2-dimethyltetrahydrofuro[3,4-d][1,3]dioxol-4-yl)methoxy)(naphthalen-1-yloxy)phosphoryl)-L-alaninate

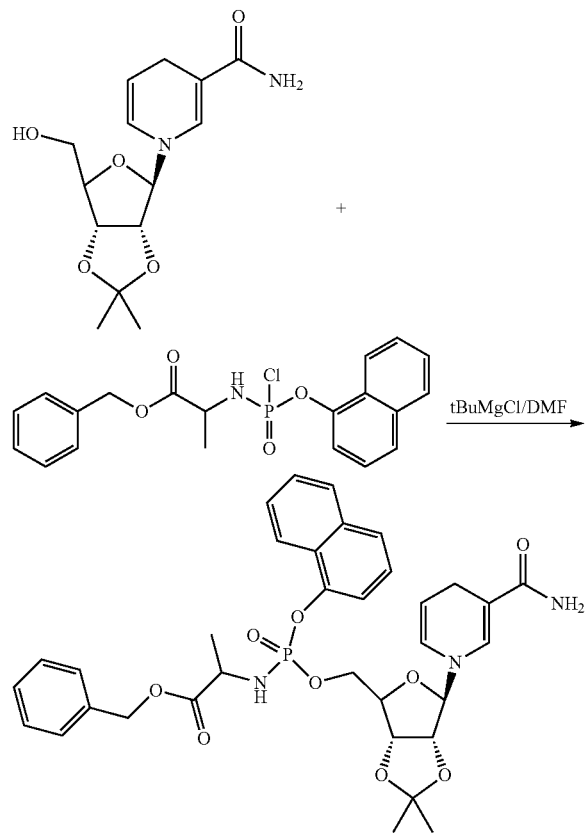

A 100 mL flask was charged with 1.4 gm (4.7 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and flushed with nitrogen. The acetonide was dissolved in 20 mL dry DMF and treated with 9.2 mL (9.2 mmol) tert-butylmagnesium chloride (1M in THF) and stirred for 30 minutes. The dark solution was treated with a solution of 3.7 gm (9.2 mmol) benzyl (chloro(naphthalen-1-yloxy)phosphoryl)-L-alaninate (Maneghesso, et al., *Antiviral Res.*, 94, 35 (2012)) in 5 mL dry DMF, and the reaction was stirred at room temperature and monitored by HPLC. After 1 hour, the reaction was complete. The solvent was stripped and the residue co-evaporated with ACN (2×) and dried in vacuo to give 8.8 gm as an amber solid. The solid was purified via flash chromatography using 0-5% MeOH in DCM as the eluent, and the pooled product fractions stripped and dried on high vacuum to give 2.32 gm benzyl ((((3aR,6R,6aR)-6-(3-carbamoylpyridin-1(4H)-yl)-2,2-dimethyltetrahydrofuro[3,4-d][1,3]dioxol-4-yl)methoxy)(naphthalen-1-yloxy)phosphoryl)-L-alaninate as a clear oil (74%).

$^1$HNMR (ACN-d$_3$): δ 8.2 (m, 1H); 7.9 (m, 2H); 7.7 (t, 1H); 7.6-7.2 (m, 10H); 7.07 (d, 1H); 5.7 (m, 1H); 5.1 (d, 2H); 4.7 (dd, 2H); 4.4 (m, 0.5H); 4.2 (m, 4H); 4.1 (d, 1H); 3.9 (m, 0.5H); 3.1 (m, 2H); 1.5 (s, 3H); 1.4 (d, 3H); 1.3 (s, 3H).

$^{31}$P NMR (ACN-d$_3$): −5.8 and −5.3 ppm.

MS (ES-API$^+$) m/z=664 (M+).

Example 8B: Benzyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(naphthalen-1-yloxy)phosphoryl)alaninate acetate salt

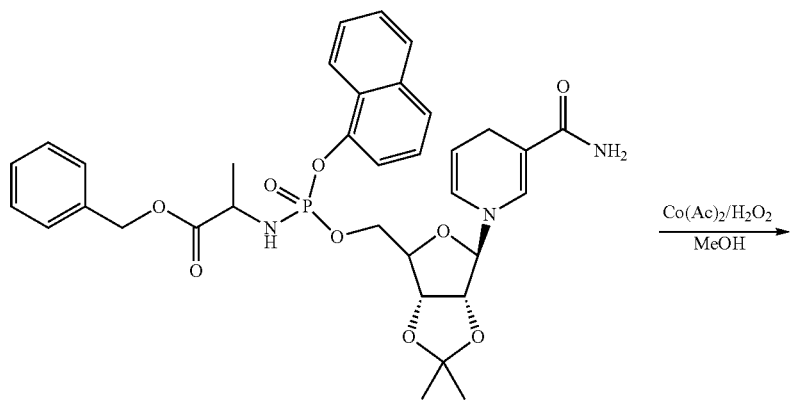

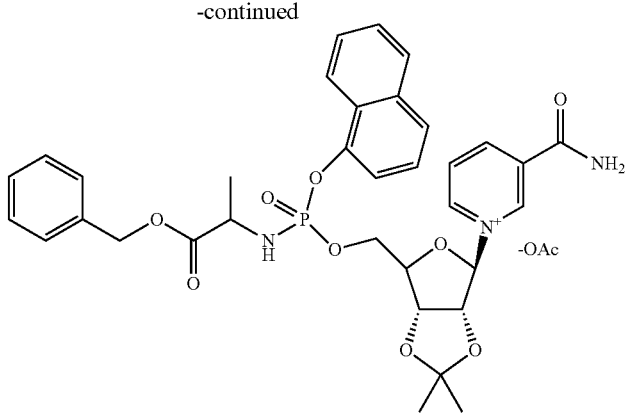

A 250 mL round-bottom flask was charged with 2.3 gm (3.5 mmol) benzyl ((((3aR,6R,6aR)-6-(3-carbamoylpyridin-1(4H)-yl)-2,2-dimethyltetrahydrofuro[3,4-d][1,3]dioxol-4-yl)methoxy)(naphthalen-1-yloxy)phosphoryl)-L-alaninate and it was dissolved in 75 mL MeOH. The solution was treated with 863 mg (3.5 mmol) CoAc$_2$·4H$_2$O and stirred to dissolve. The resulting solution was treated with 1.15 mL 30% aqueous H$_2$O$_2$ and the mixture was stirred at RT. The reaction was monitored by HPLC. After 1 hour, the reaction had progressed to ~90%. It was treated with an additional 150 μL peroxide to bring it to completion. The solution was treated with 7 gm QuadraSil AP resin and 5 mL water. The mixture was stirred for 30 minutes, filtered and washed with MeOH and water. The filtrate was stripped to remove the MeOH, then frozen and lyophilized to give 2.17 gm benzyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy) (naphthalen-1-yloxy)phosphoryl)alaninate acetate salt. LC/MS showed the material to be >96% purity with This product was used directly in the next reaction.

MS (ES-API$^+$) m/z=662 (M+).

Example 8C: 1-((2R,3R,4S)-5-(((((1-(Benzyloxy)-1-oxopropan-2-yl)amino)(naphthalen-1-yloxy)phosphoryl)oxy)methyl)-3,4-dihydroxytetrahydrofuran-2-yl)-3-carbamoylpyridin-1-ium Trifluoroacetate salt (Compound 8)

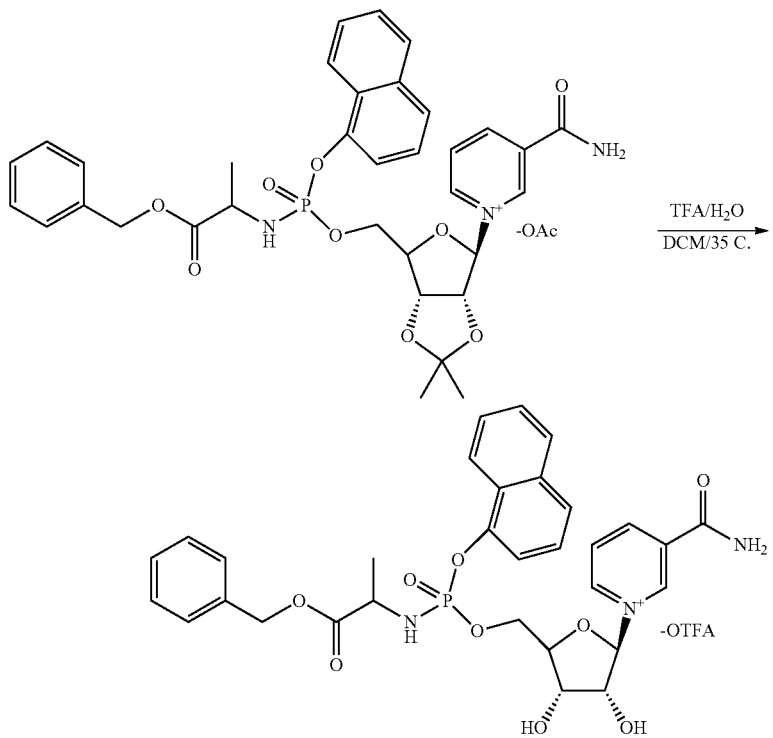

A 250 mL flask was charged with 2.17 gm (2.8 mmol) benzyl ((((3aR,6R,6aR)-6-(3-carbamoyl-1λ$^4$-pyridin-1-yl)-2,2-dimethyltetrahydrofuro[3,4-d][1,3]dioxol-4-yl) methoxy)(naphthalen-1-yloxy)phosphoryl)alaninate. This was dissolved in 25 mL DCM and treated with 25 mL 90% TFA-10% H$_2$O and the solution stirred at 35° C. After 3.5 hours, the solvent was stripped and the residue co-evaporated with ACN (2×). The residue was taken up in water and methanol, frozen and lyophilized to give 2.6 gm as a dark yellow foam. The foam was purified via flash chromatography using a gradient of 10-20% MeOH in DCM containing 2% H$_2$O and 1% HCO$_2$H. The pooled product fractions were stripped, co-evaporated with water (2×), frozen and lyophilized to give 1.23 gm 1-((2R,3R,4S)-5-(((((1-(benzyloxy)-1-oxopropan-2-yl)amino)(naphthalen-1-yloxy)phosphoryl)oxy)methyl)-3,4-dihydroxytetrahydrofuran-2-yl)-3-carbamoylpyridin-1-ium trifluoroacetate salt (59%).

$^1$H NMR (ACN-d$_3$) (For several of the proton signals, the diastereomers were clearly differentiated, as noted): δ 8.8-7.3 (m, 17H); 6.6 (d, 1H); 6.0 and 5.9 (d, 1H); 5.2 and 5.1 (s, 2H); 4.9-4.5 (m, 5H); 1.4 and 1.2 (d, 3H).

$^{31}$P NMR (ACN-d$_3$): 5.5 and 5.3 ppm.

MS (ES-API$^+$) m/z=622 (M+).

Example 9: 2-Ethylbutyl ((((3S,4R,5R)-5-(3-carbamoyl-1λ$^4$-pyridin-1-yl)-3,4-dihydroxytetrahydrofuran-2-yl)methoxy)(phenoxy)phosphoryl)alaninate Trifluoroacetate salt (Compound 9)

Example 9A: 2-Ethylbutyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)alaninate

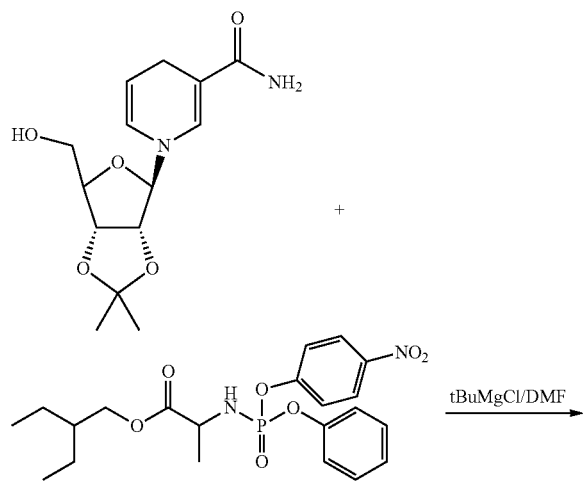

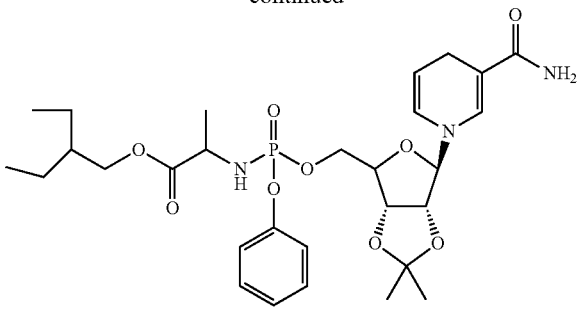

A 250 mL flask was charged with 1.83 gm (6.2 mmol)$_1$-((3aR,4R,6aR)-6-(hydroxymethyl)-2,2-dimethyltetrahydrofuro[3,4-d][1,3]dioxol-4-yl)-1,4-dihydropyridine-3-carboxamide and it was flushed with nitrogen. The compound was dissolved in 30 mL dry DMF and treated with 7.4 mL (7.4 mmol) tert-butylmagnesium chloride (1M in THF)) and stirred for 30 minutes. The resulting solution was treated with a solution of 3.34 gm (7.4 mmol) 2-ethylbutyl ((4-nitrophenoxy)(phenoxy)phosphoryl)alaninate (Mayes, et al., WO 2013/177219) in 5 mL dry DMF and the reaction was stirred at room temperature and monitored by HPLC. After one hour, the reaction was complete and the solvent was evaporated using high vacuum. The residue was then co-evaporated from ACN (2×) and from toluene (1×) and dried on high vacuum to give ~18 gm as a bright yellow semi-solid (still containing some solvent). The solid was purified via flash chromatography with a gradient of 0-5% MeOH in DCM. The pooled product fractions were stripped to give 4.4 gm 2-ethylbutyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)alaninate as a clear yellow oil (106%: material contains DMF and p-nitrophenol, neither of which affect the subsequent reactions.)

$^1$H NMR (CDCl$_3$): δ 7.9 (s, 1H); 7.3-7.1 (m, 5H); 5.7 (m, 1H); 4.7-4.0 (7H); 3.1 (d, 2H); 1.5 (d, 3H); 1.4-1.2 (m, 10H); 1.16 (s, 3H); 0.8 (dt, 6H).

$^{31}$P NMR (CDCl$_3$): 3.5 and 3.6 ppm.

MS (ES-API$^+$) m/z=608 (M$^+$).

Example 9B: 2-Ethylbutyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(phenoxy)phosphoryl)alaninate acetate salt

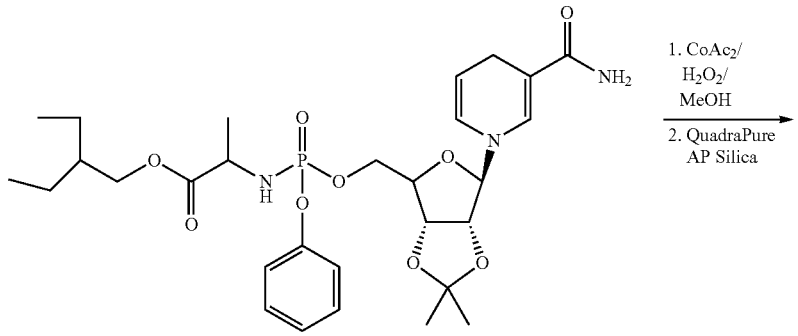

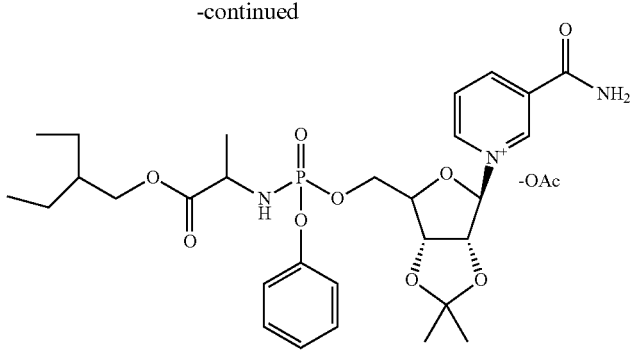

A 250 mL flask was charged 3 gm (4.93 mmol) 2-ethylbutyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)alaninate dihydroacetonide and dissolved in 100 mL MeOH. The solution was treated with a solution of 1.23 gm (4.93 mmol) CoAc$_2$·4H$_2$O in 25 mL MeOH. The solution was treated with 2 mL 30% aqueous H$_2$O$_2$ and the mixture was allowed to stir at room temperature. The reaction was monitored by HPLC and was nearly complete in 30 minutes; an additional 100 μl peroxide was added to drive it to completion. After 30 minutes, the dark solution was treated with 12 gm QuadraSil AP resin and 10 mL water. After stirring for 15 minutes, the resin was removed by filtration and the solid washed with MeOH and water. The filtrate was stripped to remove the MeOH and the aqueous solution frozen and lyophilized to afford 2.54 gm 2-ethylbutyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(phenoxy)phosphoryl)alaninate acetate salt, as a dark solid, which was used directly in the next reaction.

Example 9C: 2-Ethylbutyl ((((3S,4R,5R)-5-(3-carbamoyl-1λ$^4$-pyridin-1-yl)-3,4-dihydroxytetrahydrofuran-2-yl)methoxy)(phenoxy)phosphoryl)alaninate Trifluoroacetate salt (Compound 9)

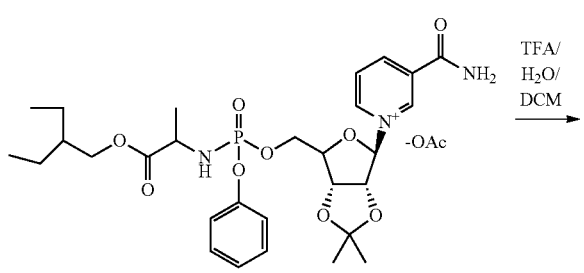

A 250 mL flask was charged with 2.5 gm crude 2-ethylbutyl ((((3aR,6R,6aR)-6-(3-carbamoyl-1λ$^4$-pyridin-1-yl)-2,2-dimethyltetrahydrofuro[3,4-d][1,3]dioxol-4-yl)methoxy)(phenoxy)phosphoryl)alaninate acetate salt and it was dissolved in 40 mL DCM. The solution was treated with 40 mL 90% TFA/10% H$_2$O and the solution was stirred at 37° C. After 45 minutes, the solvent was stripped and the residue evaporated on high vacuum, then co-evaporated with ACN (2×). The crude product was diluted with water, frozen and lyophilized to give 3.19 gm as a dark solid. The solid was purified via flash chromatography with a gradient of 10-15% MeOH in DCM, (containing 1% formic acid and 2% H$_2$O). The pooled fractions were stripped and then co-evaporated with water (3×) to remove residual formic acid. The product was the taken up in water/ACN, frozen and lyophilized to give 1.54 2-ethylbutyl ((((3S,4R,5R)-5-(3-carbamoyl-1λ$^4$-pyridin-1-yl)-3,4-dihydroxytetrahydrofuran-2-yl)methoxy)(phenoxy)phosphoryl)alaninate trifluoroacetate salt, as a tan solid (36% 2-step yield).

$^1$H NMR (D$_2$O) (For several of the proton signals, the diastereomers were clearly differentiated, as noted): δ 9.4 and 9.3 (s, 1H); 9.2 and 9.1 (d, 1H); 9.0 and 8.9 (d, 1H); 8.3 and 8.2 (t, 1H); 7.3 (m, 2H); 7.2 (m, 1H); 7.1 (m, 2H); 6.3 and 6.2 (d, 1H); 4.75 (m, 1H); 4.65 (m, 1H); 4.55 (m, 0.5H); 4.45 (m, 0.5H); 4.33 (m, 0.5H); 4.25 (m, 0.5H); 4.05 (m, 3H); 1.5 (m, 1H); 1.4 (d, 3H); 1.3 (m, 4H).

$^{31}$P NMR (D$_2$O): 5.3 and 5.1 ppm.

MS (ES-API$^+$) m/z=566 (M+).

Example 10: Neopentyl ((((3S,4R,5R)-5-(3-carbamoyl-1λ$^4$-pyridin-1-yl)-3,4-dihydroxytetrahydrofuran-2-yl)methoxy)(phenoxy)phosphoryl)alaninate Trifluoroacetate salt (Compound 10)

Example 10A: Neopentyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)alaninate

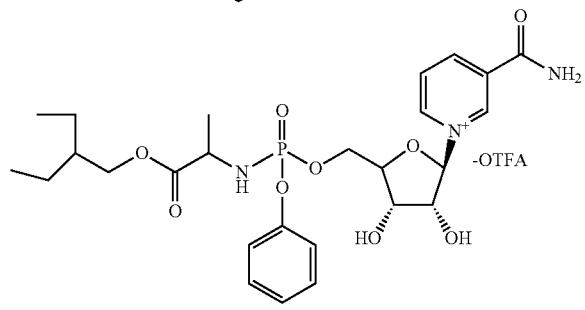

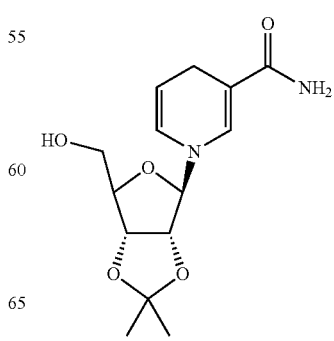

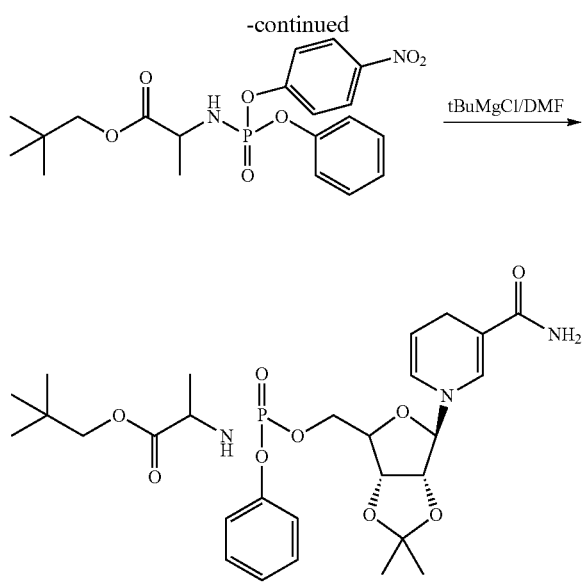

A 100 mL flask was charged with 792 mg (2.7 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and it was flushed with nitrogen. The compound was dissolved in 20 mL dry DMF and treated with tert-butylmagnesium chloride (1M in THF)) and stirred for 30 minutes and then treated with a solution of 1.4 gm (3.2 mmol) neopentyl ((4-nitrophenoxy)(phenoxy)phosphoryl)alaninate (Menghesso, et al., *Antiviral Res.,* 94, 35 (2012)) 5 mL dry DMF. The reaction was stirred at room temperature overnight. The solvent was stripped to give an oil that was co-evaporated from toluene (2×) and dried on high vacuum to give 3.1 gm. The product was pooled with product from a previous reaction and purified via flash chromatography using a gradient of 0-10% MeOH in DCM. The pooled product fractions were evaporated to dryness to give 2.8 gm neopentyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)alaninate as an oil.

$^1$H NMR (CDCl$_3$): δ 8.0 and 7.9 (s, 2H); 7.3-7.1 (m, 5H); 6.8 and 6.7 (s, 1H); 5.8 (m, 1H); 4.6 (m, 2H); 4.5 (m, 1H); 4.3 (m, 3H); 3.8 (m, 1H); 3.7 (m, 1H); 3.0 (m, 2H); 1.5 (s, 3H); 1.4 (s, 3H); 1.2 d, 3H); 0.9 (9H). (Contains DMF 2.9 and 2.8 ppm)

$^{31}$P (CDCl$_3$): 3.6 ppm (bd).

MS (ES-API$^+$) m/z=593 (M+).

Example 10B: Neopentyl (((((3aR,6R,6aR)-6-(3-carbamoyl-1λ$^4$-pyridin-1-yl)-2,2-dimethyltetrahydrofuro[3,4-d][1,3]dioxol-4-yl)methoxy)(phenoxy)phosphoryl)alaninate acetate salt

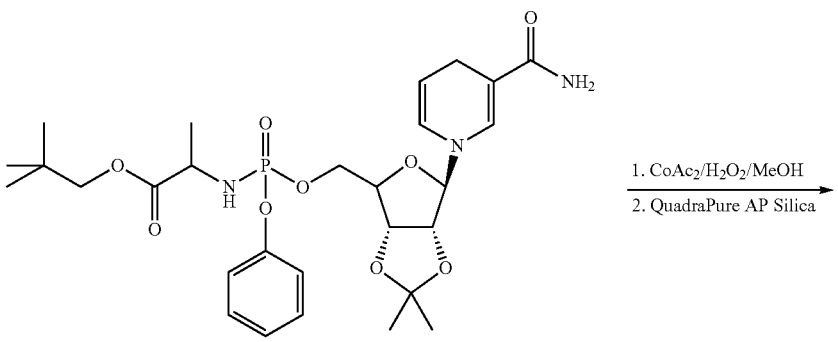

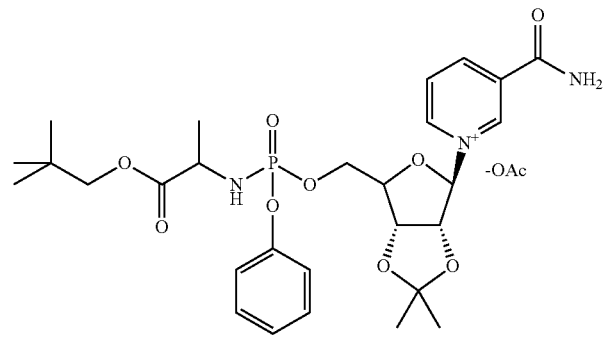

A 250 mL flask was charged with 2.7 gm (4.5 mmol) neopentyl ((((3aR,6R,6aR)-6-(3-carbamoylpyridin-1(4H)-yl)-2,2-dimethyltetrahydrofuro[3,4-d][1,3]dioxol-4-yl)methoxy)(phenoxy)phosphoryl)alaninate and it was dissolved in MeOH. The solution was treated with 1.13 gm (4.5 mmol) CoAc$_2$·4H$_2$O and the mixture was stirred briefly to dissolve and treated with 2 mL 30% aqueous H$_2$O$_2$. The dark solution was stirred at room temperature and the reaction monitored by HPLC. After 25 minutes, the reaction was complete. The solution was treated with 13 gm QuadraSil resin and 5 mL water and allowed to stir 45 minutes. The resin was filtered and washed with MeOH and water. The filtrate was evaporated in vacuo, diluted with water, frozen and lyophilized to afford 2.25 gm neopentyl (((((3aR,6R,6aR)-6-(3-carbamoyl-1λ$^4$-pyridin-1-yl)-2,2-dimethyltetrahydrofuro[3,4-d][1,3]dioxol-4-yl)methoxy)(phenoxy)phosphoryl)alaninate acetate salt as a dark solid. This solid was used directly in the next reaction.

MS (ES-API$^+$) m/z=592 (M+).

Example 10C: Neopentyl (((((3S,4R,5R)-5-(3-carbamoyl-1λ$^4$-pyridin-1-yl)-3,4-dihydroxytetrahydrofuran-2-yl)methoxy)(phenoxy)phosphoryl)alaninate Trifluoroacetate salt (Compound 10)

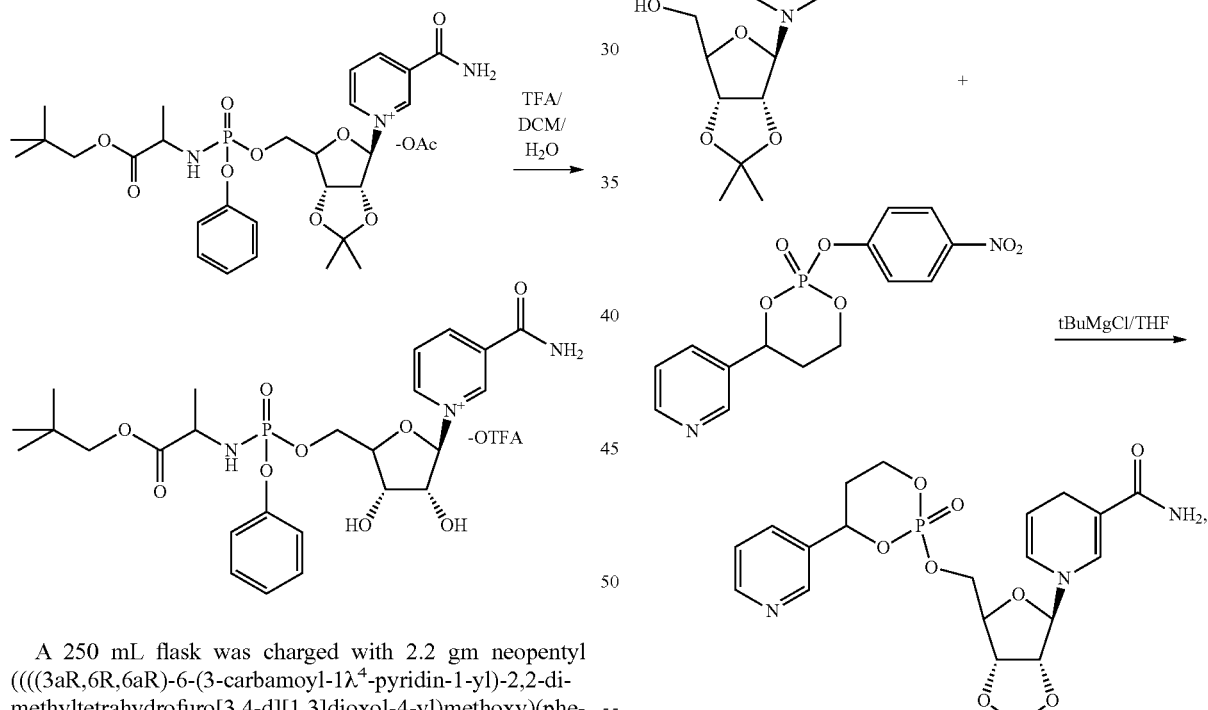

A 250 mL flask was charged with 2.2 gm neopentyl (((((3aR,6R,6aR)-6-(3-carbamoyl-1λ$^4$-pyridin-1-yl)-2,2-dimethyltetrahydrofuro[3,4-d][1,3]dioxol-4-yl)methoxy)(phenoxy)phosphoryl) alaninate acetate salt and was dissolved in 25 mL DCM. The solution was treated with 25 mL 90% TFA/H$_2$O and stirred at 37° C. After 45 minutes, the solvent was stripped on high vacuum and the residue co-evaporated with ACN (2×), then diluted with water, frozen and lyophilized to give 3.19 gm as a dark solid. The crude product was purified via flash chromatography with a gradient of 5-15% MeOH in DCM, containing 1% HCO$_2$H-2% H$_2$O. The pooled fractions were stripped and co-evaporated with water (3×) to remove formic acid. The product was taken up in water and ACN, frozen and lyophilized to give 496 mg neopentyl (((((3S,4R,5R)-5-(3-carbamoyl-1λ$^4$-pyridin-1-yl)-3,4-dihydroxytetrahydrofuran-2-yl)methoxy)(phenoxy)phosphoryl)alaninate trifluoroacetate salt as a tan solid.

$^1$H NMR (ACN-d$_3$) (For some of the proton signals, the diastereomers were clearly differentiated, as noted): δ 9.7 and 9.6 (bd s, 1H); 9.2 and 9.0 (m, 1H); 8.6 (m, 1H); 8.2 (d, 1H); 7.4-7.1 (m, 5H); 6.2 and 6.1 (m, 1H); 4.85 (m, 2H); 4.6-3.9 (5H); 3.7 (m, 1H); 1.37 and 1.36 (d, 3H); 0.95 (9H).

$^{31}$P NMR (ACN-d$_3$): 5.4 ppm (bd)

MS (ES-API$^+$) m/z=552 (M+).

Example 11: 1-((2R,3R,4S)-3,4-Dihydroxy-5-(((2-oxido-4-(pyridin-3-yl)-1,3,2-dioxaphosphinan-2-yl)oxy)methyl)tetrahydrofuran-2-yl)-1λ$^4$-pyridine-3-carboxamide Trifluoroacetate salt (Compound 11)

Example 11A: 1-((3aR,4R,6aR)-2,2-Dimethyl-6-(((2-oxido-4-(pyridin-3-yl)-1,3,2-dioxaphosphinan-2-yl)oxy)methyl)tetrahydrofuro[3,4-d][1,3]dioxol-4-yl)-1,4-dihydropyridine-3-carboxamide

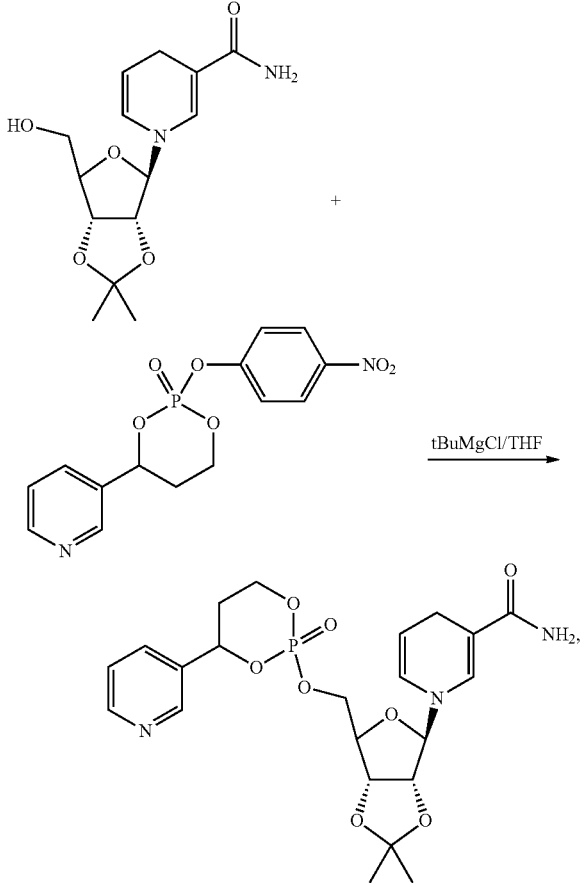

A 250 mL flask was charged with 2.0 gm (6.76 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and flushed with nitrogen. The compound was dissolved in 25 mL dry DMF and treated with 10.1 mL (10.1 mmol) tert-butylmagnesium chloride (1M in THF) and stirred for 30 minutes. The dark solution was treated with a solution of 2.5 gm (7.44 mmol) (±)-2-(4-nitrophenoxy)-4-(pyridin-3-yl)-1,3,2-dioxaphosphinane 2-oxide (Reddy, et al., *J. Med. Chem.*, 51, 666 (2008) in 12 mL dry DMF and the reaction was stirred at room temperature overnight. The solvent was stripped to give a dark oil which was co-evaporated from ACN (2×). A precipitate formed upon the addition of ACN, which was removed by filtration and washed with ACN. The combined filtrates were evaporated to give 1.3 gm as an oil. The oil was purified via flash chromatography with 5-25% MeOH in DCM. The pooled product fractions were evaporated to afford 1.3 gm 1-((3aR,4R,6aR)-2,2-dimethyl-6-(((2-oxido-4-(pyridin-3-yl)-1,3,2-dioxaphosphinan-2-yl)oxy)methyl)tetrahydrofuro[3,4-d][1,3]dioxol-4-yl)-1,4-dihydropyridine-3-carboxamide as a pale yellow solid that was used directly in the next reaction.

$^1$H NMR (DMSO-$d_6$): δ 8.7 (d, 1H); 8.6 (d, 1H); 7.9 (d, 1H); 7.5 (dd, 1H); 6.1 (d, 1H); 4.9 (d, 1H); 4.7-3.2 (10H); 2.4 (m, 1H); 2.3 (m, 1H); 1.4 (s, 3H); 1.3 (s, 3H).

$^{31}$P NMR (DMSO-$d_6$): −6.1 and −6.2 ppm.

MS (ES-API$^+$) m/z=493 (M$^+$).

Example 11B: 1-((3aR,4R,6aR)-2,2-Dimethyl-6-(((2-oxido-4-(pyridin-3-yl)-1,3,2-dioxaphosphinan-2-yl)oxy)methyl)tetrahydrofuro[3,4-d][1,3]dioxol-4-yl)-1λ$^4$-pyridine-3-carboxamide acetate salt

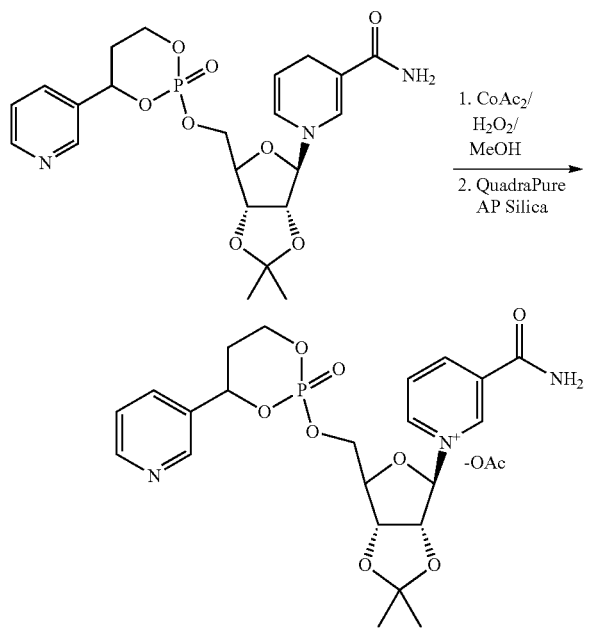

A flask was charged with a solution of 1.8 gm (2.5 mmol) 1-((3aR,4R,6aR)-2,2-dimethyl-6-(((2-oxido-4-(pyridin-3-yl)-1,3,2-dioxaphosphinan-2-yl)oxy)methyl)tetrahydrofuro[3,4-d][1,3]dioxol-4-yl)-1,4-dihydropyridine-3-carboxamide in 50 mL MeOH. This was treated with 613 mg (2.5 mmol) CoAc$_2$·4H$_2$O and stirred to dissolve, then treated with 750 uL 30% aqueous H$_2$O$_2$. The dark solution was stirred at room temperature and the reaction monitored by LC/MS. After 45 minutes, the solution was treated with 4.5 gm QuadaSil AP resin and 5 mL water. The mixture was stirred for 90 minutes, filtered, and the resin washed with water and MeOH. The filtrate as stripped, frozen and lyophilized to afford 1.8 gm 1-((3aR,4R,6aR)-2,2-dimethyl-6-(((2-oxido-4-(pyridin-3-yl)-1,3,2-dioxaphosphinan-2-yl)oxy)methyl)tetrahydrofuro[3,4-d][1,3]dioxol-4-yl)-1λ$^4$-pyridine-3-carboxamide acetate salt, as a colored solid that was used directly in the next reaction. LC/MS shows a single product peak with MS (ES-API$^+$) m/z=493 (M$^+$).

Example 11C: 1-((2R,3R,4S)-3,4-Dihydroxy-5-(((2-oxido-4-(pyridin-3-yl)-1,3,2-dioxaphosphinan-2-yl)oxy)methyl)tetrahydrofuran-2-yl)-1λ$^4$-pyridine-3-carboxamide Trifluoroacetate salt (Compound 11)

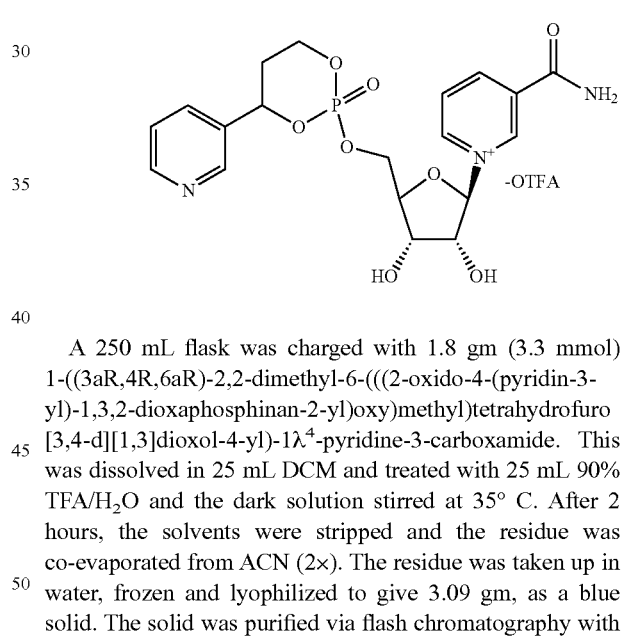

A 250 mL flask was charged with 1.8 gm (3.3 mmol) 1-((3aR,4R,6aR)-2,2-dimethyl-6-(((2-oxido-4-(pyridin-3-yl)-1,3,2-dioxaphosphinan-2-yl)oxy)methyl)tetrahydrofuro[3,4-d][1,3]dioxol-4-yl)-1λ$^4$-pyridine-3-carboxamide. This was dissolved in 25 mL DCM and treated with 25 mL 90% TFA/H$_2$O and the dark solution stirred at 35° C. After 2 hours, the solvents were stripped and the residue was co-evaporated from ACN (2×). The residue was taken up in water, frozen and lyophilized to give 3.09 gm, as a blue solid. The solid was purified via flash chromatography with a gradient of 15-20% MeOH in DCM, containing 1% formic acid and 3% water. The product fractions were pooled and stripped and co-evaporated from water (2×). The product was taken up in water, frozen and lyophilized to give 620 mg 1-((2R,3R,4S)-3,4-dihydroxy-5-(((2-oxido-4-(pyridin-3-yl)-1,3,2-dioxaphosphinan-2-yl)oxy)methyl)tetrahydrofuran-2-yl)-1λ$^4$-pyridine-3-carboxamide trifluoroacetate salt, as a pale blue solid (33%).

$^1$H NMR (D$_2$O): δ 9.3 and 9.2 (s, 1H); 9.1 (m, 1H); 8.8 (m, 1H); 8.5 (m, 1H); 8.1 (m, 1H); 7.9 (m, 1H); 7.5 (m, 1H); 6.1 and 6.0 (d, 1H); 4.6-4.3 (9H); 2.4-2.2 (2H).

$^{31}$P NMR (D$_2$O): −4.7 and −4.9 ppm.

MS (ES-API$^+$) m/z=452 (M$^+$).

Example 12: 1-((2R,3R,4S)-5-(((4-(3-Chloro-4-fluorophenyl)-2-oxido-1,3,2-dioxaphosphinan-2-yl)oxy)methyl)-3,4-dihydroxytetrahydrofuran-2-yl)-1λ⁴-pyridine-3-carboxamide Trifluoroacetate salt (Compound 12)

Example 12A: 1-((3aR,4R,6aR)-6-(((4-(3-Chloro-4-fluorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide

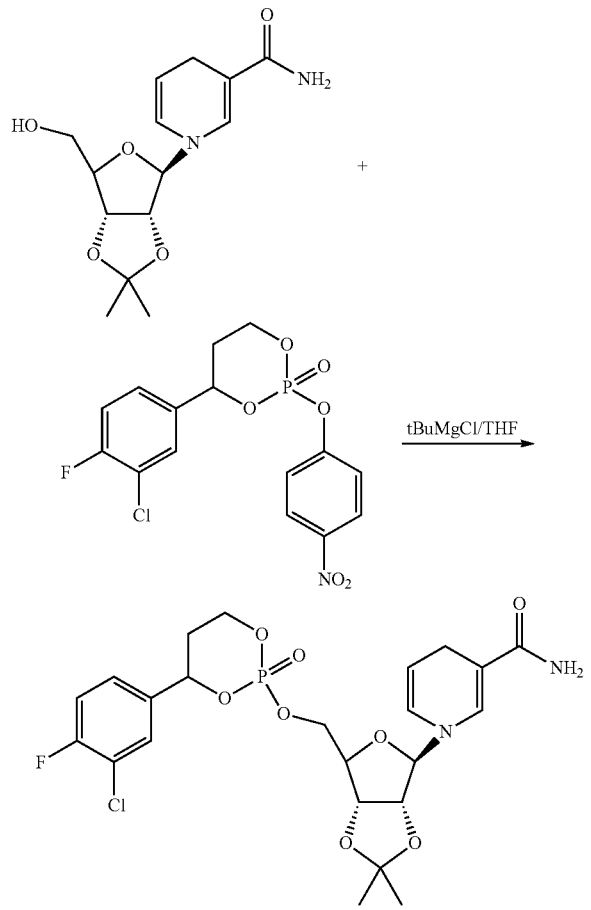

A 500 mL round-bottomed flask was charged with 2.89 gm (9.8 mmol) 1-((3aR,4R,6aR)-6-(hydroxymethyl)-2,2-dimethyltetrahydrofuro[3,4-d][1,3]dioxol-4-yl)-1,4-dihydropyridine-3-carboxamide and it was flushed with nitrogen. This material was dissolved in 75 mL dry DMF and treated with 14.7 mL (14.7 mmol) tert-butylmagnesium chloride (1M in THF) and the solution was stirred for 30 minutes. This solution was treated with a solution of the 4.16 gm (10.7 mmol) (±)-4-(3-chloro-4-fluorophenyl)-2-(4-nitrophenoxy)-1,3,2-dioxaphosphinane 2-oxide (Erion, et al. PCT Int. Appl., 2007/022073) in 75 mL dry DMF and the reaction was warmed to 45° C. and stirred. The reaction was monitored by HPLC and was seen to be complete after 3 hours, whereupon it was cooled to room temperature. The reaction was stripped under high vacuum to give a thick oil. This was taken up in ~250 mL DCM and extracted with 3× 200 mL water, then brine. The organic layer was dried over sodium sulfate, filtered and evaporated to give 5 gm as a dark solid. This was purified via flash chromatography using a gradient of 0-10% MeOH in DCM. The product fractions were pooled and evaporated to give 2.65 gm 1-((3aR,4R,6aR)-6-(((4-(3-chloro-4-fluorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide as a yellow/orange solid.

$^1$H NMR (CDCl$_3$): δ 8.0 (s, ~2H); 7.5-7.0 (m, 5H); 5.6 (d, 1H); 4.9-4.2 (m, 9H); 3.1 (d, 2H); 2.3 (m, 1H); 2.1 (m, 1H); 1.5 (s, 3H); 1.3 (s, 3H). Residual DMF also present.

$^{31}$P NMR (CDCl$_3$): −4.8 and −5.0 ppm.

MS (ES-API$^+$) m/z=545 (M+).

Example 12B: 1-((3aR,4R,6aR)-6-(((4-(3-chloro-4-fluorophenyl)-2-oxido-1,3,2-dioxaphosphinan-2-yl)oxy)methyl)-2,2-dimethyltetrahydrofuro[3,4-d][1,3]dioxol-4-yl)-1λ⁴-pyridine-3-carboxamide acetate salt

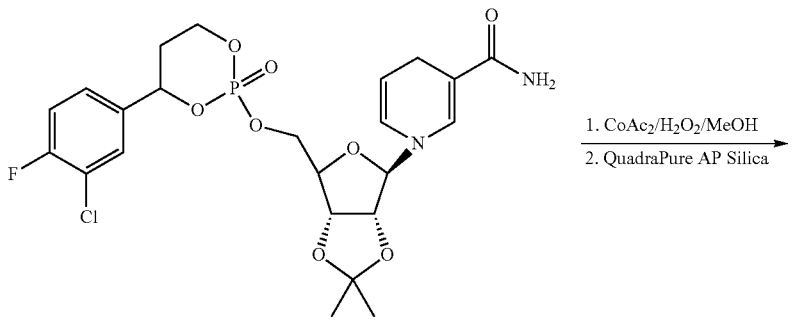

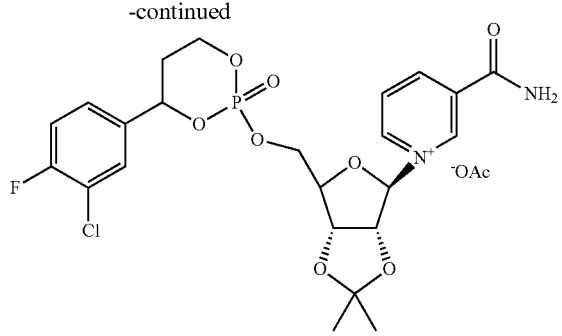

A 250 mL flask was charged with 2.15 gm (3.95 mmol) 1-((3aR,4R,6aR)-6-(((4-(3-chloro-4-fluorophenyl)-2-oxido-1,3,2-dioxaphosphinan-2-yl)oxy)methyl)-2,2-dimethyltetrahydrofuro[3,4-d][1,3]dioxol-4-yl)-1,4-dihydropyridine-3-carboxamide and treated with a solution of 982 mg (3.95 mmol) $CoAc_2 \cdot 4H_2O$ in 100 mL MeOH that had been cooled to 0° C. The solution was treated with 900 µL 30% $H_2O_2$, and the mixture was allowed to warm to room temperature and the reaction monitored by HPLC. The reaction was ~50% complete after 1 hour and was treated with an additional 950 µL $H_2O_2$ over the next three hours. The reaction was then treated with 10 gm Quadrasil AP and 10 mL water and stirred at room temperature for 90 minutes. The resin was removed by filtration, the solid washed with water and MeOH and the filtrate stripped to afford 3 gm 1-((3aR,4R,6aR)-6-(((4-(3-chloro-4-fluorophenyl)-2-oxido-1,3,2-dioxaphosphinan-2-yl)oxy)methyl)-2,2-dimethyltetrahydrofuro[3,4-d][1,3]dioxol-4-yl)-1$\lambda^4$-pyridine-3-carboxamide acetate salt as a dark solid. The crude product was used directly in next reaction.

MS (ES-API$^+$) m/z=543 (M+)

Example 12C: 1-((2R,3R,4S)-5-(((4-(3-Chloro-4-fluorophenyl)-2-oxido-1,3,2-dioxaphosphinan-2-yl)oxy)methyl)-3,4-dihydroxytetrahydrofuran-2-yl)-1$\lambda^4$-pyridine-3-carboxamide Trifluoroacetate salt (Compound 12)

A 500 mL flask was charged with 2.4 gm (3.92 mmol) 1-((3aR,4R,6aR)-6-(((4-(3-chloro-4-fluorophenyl)-2-oxido-1,3,2-dioxaphosphinan-2-yl)oxy)methyl)-2,2-dimethyltetrahydrofuro[3,4-d][1,3]dioxol-4-yl)-1$\lambda^4$-pyridine-3-carboxamide acetate salt. This compound was dissolved 25 mL DCM and treated with 25 mL 90% TFA/$H_2O$. The dark solution was stirred at 35° C. for 1 hour. The solvent was stripped on high-vacuum and co-evaporated with ACN (2×). The residue was diluted with water, frozen, and lyophilized to give 3 gm of a dark semi-solid. This was purified via flash chromatography using a gradient of 10-30% MeOH in DCM, containing 1% formic acid and 2% water. The pooled product fractions were pooled, stripped, co-evaporated from water, taken up in water, frozen and lyophilized to give 510 mg 1-((2R,3R,4S)-5-(((4-(3-chloro-4-fluorophenyl)-2-oxido-1,3,2-dioxaphosphinan-2-yl)oxy)methyl)-3,4-dihydroxytetrahydrofuran-2-yl)-1$\lambda^4$-pyridine-3-carboxamide trifluoroacetate salt, as a pale yellow solid (21%). LC/MS shows two peaks corresponding to the two diastereomers, each with the same mass. MS (ES-API$^+$) m/z=503 (M+).

$^1$H NMR ($D_2O$) (For several of the proton signals, the diastereomers were clearly differentiated, as noted): δ 9.3 and 9.2 (s, 1H); 9.1 and 9.0 (d, 1H); 8.6 (m, 1H); 8.1 (m, 1H); 7.3 (m, 3H); 6.2 and 6.1 (d, 1H); 4.5-3.6 (m, 10H); 2.1 (m, 1H); 1.9 (m, 1H).

$^{31}$P NMR ($D_2O$): 4.5 and 4.9 ppm; 5.9 and 6.3 ppm. These signals correspond to the four diastereomers generated from chiral centers produced at the racemic diol and the phosphorus.

Example 13: ((2R,3S,4R,5R)-5-(3-Carbamoylpyridin-1-ium-1-yl)-3,4-dihydroxytetrahydrofuran-2-yl)methyl isopropyl phosphate (Compound 13)

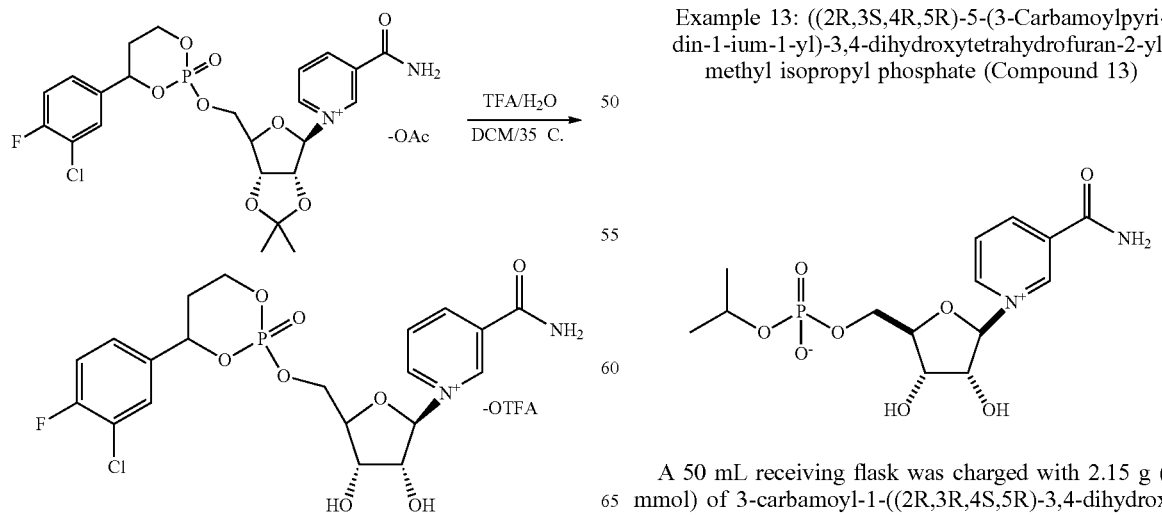

A 50 mL receiving flask was charged with 2.15 g (5.32 mmol) of 3-carbamoyl-1-((2R,3R,4S,5R)-3,4-dihydroxy-5-(hydroxymethyl)tetrahydrofuran-2-yl)pyridin-1-ium trifluoromethanesulfonate (nicotinamide riboside trifluoromethanesulfonate salt). (Sauve et al. WO2007061798) This material was suspended in 12 mL of anhydrous acetonitrile, then concentrated in vacuo (35° C., ca. 1 torr) to a foam. A stir bar was added, and the flask was placed under argon. To this was added 13 mL of trimethylphosphate. The mixture was cooled with an ice bath, then 973 microliters (10.6 mmol) of phosphorus oxychloride was added via syringe, in one portion. The reaction was stirred while cooling with an ice bath for 6.75 h, then 3.5 g (58.2 mmol) of isopropanol was added in one portion. This was allowed to stand at 4° C. for 24 h, then 5 mL of water was added in one portion, and the mixture was allowed to stand at 4° C. for an additional 15 h.

Immediately prior to chromatography, the reaction mixture was diluted with 30 mL of ethyl acetate. A 100 g Quadrasil AP column was conditioned according to the procedure described in J. Org. Chem., 2012, 77, 7319-7329. Following conditioning, the column was pre-equilibrated with ethyl acetate, and topped with 10 mL of ethyl acetate. The crude reaction mixture in ethyl acetate was added to the top of the column, then eluted onto the column. The column was eluted sequentially with 200 mL of ethyl acetate, then with 550 mL of 60:40 (v:v) ethyl acetate: methanol, collecting 35 mL fractions. Fractions were monitored by LCMS for the presence of product (m/z=377 (M+H)$^+$). Fractions that were >98% pure by LCMS were pooled and concentrated in vacuo to a white foam. An additional 35 mL of 60:40 ethyl acetate: methanol was added to the foam, and crystals formed. The crystals were filtered, and dried in vacuo to give 197 mg (10%) of the title product. The supernatant was concentrated in vacuo. This concentration residue was stirred with 80:20 ethyl acetate: methanol to give additional crystals. These crystals were filtered, washed with 90:10 ethyl acetate: methanol, then dried in vacuo to give 329 mg (17%) of the title product. The total yield was 526 mg (27%) of a colorless, crystalline solid.

$^1$H NMR (500 MHz, D$_2$O) δ 9.42 (d, 1H, J=1.5 Hz), 9.24 (d, 1H, J=6.3 Hz), 8.95 (dt, 1H, J=8.1, 1.5 Hz), 8.26 (dd, 1H, J=8.1, 6.3 Hz), 6.18 (d, 1H, J=5.5 Hz), 4.59 (quintet, 1H, J=2.5 Hz), 4.50 (t, 1H, J=5.2 Hz), 4.39 (dd, 1H, J=5.0, 3.0 Hz), 4.38-4.32 (m, 1H), 4.26 (ddd, 1H, J=12.0, 4.5, 2.4 Hz), 4.10 (ddd, 1H, J=12.0, 5.1, 2.2 Hz), 1.19 (dd, 6H, J=6.2, 2.3 Hz).

MS (ES-API$^+$) m/z=377.0 (M+H$^+$).

Example 14: ((2R,3S,4R,5R)-5-(3-Carbamoylpyridin-1-ium-1-yl)-3,4-dihydroxytetrahydrofuran-2-yl) methyl ethyl phosphate (Compound 14)

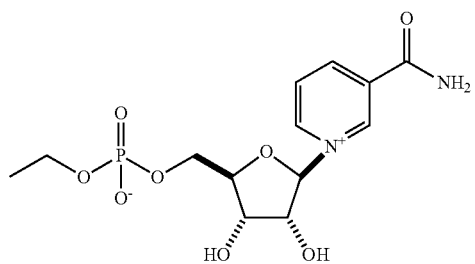

This compound was prepared according to Example 13, substituting ethyl alcohol for isopropanol. The product was purified in a similar way, eluting over a 100 g Quadrasil AP column first with ethyl acetate to remove the reaction solvent, then with 50:50 ethyl acetate: methanol to remove impurities, and finally with 30:70 ethyl acetate: methanol to isolate the product. Concentration of the product containing fractions followed by dissolution of the residue in water and lyophilization gave 293 mg (15%) of the product as a white solid.

$^1$H NMR (500 MHz, D$_2$O) δ 9.41 (d, 1H, J=1.6 Hz), 9.23 (dd, 1H, J=6.3, 1.2 Hz), 8.95 (dt, 1H, J=8.1, 1.6 Hz), 8.26 (dd, 1H, J=8.1, 6.3 Hz), 6.18 (d, 1H, J=5.4 Hz), 4.60 (quintet, 1H, J=2.6 Hz), 4.50 (t, 1H, J=5.2 Hz), 4.39 (dd, J=5.1, 2.7 Hz), 4.27 (ddd, 1H, J=12.0, 4.4, 2.4 Hz), 4.11 (ddd, 1H, J=12.0, 5.2, 2.3 Hz), 3.87 (quintet, 2H, J=7.2 Hz), 1.19 (td, 3H, J=7.1, 0.5 Hz).

MS (ES-API$^+$) m/z=362.9 (M+H$^+$).

Example 15: ((2R,3S,4R,5R)-5-(3-Carbamoylpyridin-1-ium-1-yl)-3,4-dihydroxytetrahydrofuran-2-yl) methyl propyl phosphate (Compound 15)

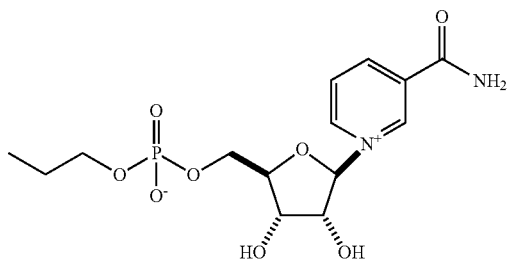

This compound was prepared according to Example 13, substituting n-propyl alcohol for isopropanol and stirring for 1.25 h instead of 24 h before the addition of water. The product was purified in a similar way, eluting over a 100 g Quadrasil AP column first with ethyl acetate to remove the reaction solvent, then with 70:30 ethyl acetate: methanol to elute the product. The product from the column was recrystallized from 70:30 ethyl acetate: methanol to give 771 mg (40%) of the product as a colorless crystalline solid.

$^1$H NMR (500 MHz, D$_2$O) δ 9.42 (m, 1H), 9.23 (m, 1H), 8.95 (dt, 1H, J=8.1, 1.5 Hz), 8.26 (dd, 1H, J=8.1, 6.4 Hz), 6.18 (d, 1H, J=5.4 Hz), 4.60 (quintet, 1H, J=2.5 Hz), 4.50 (t, 1H, J=5.2 Hz), 4.40 (dd, 1H, J=5.1, 2.7 Hz), 4.27 (ddd, J=12.0, 4.4, 2.4 Hz), 4.11 (ddd, 1H, J=12.0, 5.2, 2.2 Hz), 3.76 (m, 2H), 1.56 (m, 2H), 0.84 (t, 3H, J=7.4 Hz).

MS (ES-API$^+$) m/z=377.0 (M+H$^+$).

Example 16: ((2R,3S,4R,5R)-5-(3-Carbamoylpyridin-1-ium-1-yl)-3,4-dihydroxytetrahydrofuran-2-yl) methyl phosphate (Compound 16)

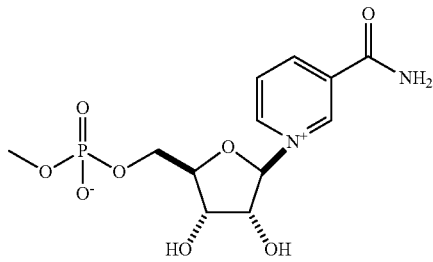

A 100 mL receiving flask was charged with 4.62 g (11 mmol) of 3-carbamoyl-1-((2R,3R,4S,5R)-3,4-dihydroxy-5-

(hydroxymethyl)tetrahydrofuran-2-yl)pyridin-1-ium trifluoromethanesulfonate (nicotinamide riboside trifluoromethanesulfonate salt). To this was added 50 mL of anhydrous acetonitrile, then the mixture was stirred at ambient temperature for 15 min, and concentrated in vacuo to a light yellow foam. The foam was maintained under an argon atmosphere. To the foam was added 25 mL of trimethylphosphate via syringe at ambient temperature. The mixture was stirred at ambient temperature for 5 min, then cooled with an ice bath. To this was added 4.2 mL (45.9 mmol) of $POCl_3$. The mixture was stirred with ice cooling for 3 h, then the solution of 3-carbamoyl-1-((2R,3R,4S,5R)-5-(((dichlorophosphoryl)oxy)methyl)-3,4-dihydroxytetrahydrofuran-2-yl)pyridin-1-ium chloride/trifluoromethanesulfonate was used in subsequent phosphate ester preparations.

A 9.5 g quantity of the above reaction mixture was placed into a 50 mL receiving flask under argon and cooled with an ice bath. To this was added 1.0 mL of methanol, then the mixture was stirred for 10 min. Next, 6 mL of water was added, then the solution was stored at 4° C. for three days. The product was purified by eluting over a 100 g Quadrasil AP column which had been conditioned according to the procedure described in J. Org. Chem. 2012, 77, 7319-7329, and subsequently placed in ethyl acetate. The reaction mixture was diluted with 60 mL of ethyl acetate and 10 mL of methanol. This was eluted onto the column, then the column was eluted with 100 mL of 80:20 (v:v) ethyl acetate: methanol, followed by 450 mL of 30:70 ethyl acetate: methanol. Approximately 20 mL fractions were collected during the 30:70 ethyl acetate: methanol elution. Product containing fractions were identified by LCMS. These were pooled and concentrated in vacuo to an oily residue. This was followed by 2×3 mL with water to remove the residual organic solvents. The residue was taken up in 3 mL of water and filtered through a cotton plug, then the cotton plug was rinsed with an additional 7 mL of water. The aqueous solution was frozen and lyophilized to give 263 mg (18%) of a colorless solid. The product purity was >98% by LCMS, monitoring at 214 nm.

$^1$H NMR (500 MHz, $D_2O$) δ 9.41 (m, 1H), 9.22 (m, 1H), 8.95 (dt, 1H, J=8.1, 1.5 Hz), 8.26 (dd, 1H, J=8.0, 6.4 Hz), 6.18 (d, 1H, J=5.4 Hz), 4.60 (quintet, 1H, J=2.6 Hz), 4.50 (t, 1H, J=5.2 Hz), 4.40 (dd, 1H, J=5.1, 2.8 Hz), 4.27 (ddd, 1H, J=12.0, 4.4, 2.4 Hz), 4.11 (ddd, 1H, J=12.0, 5.2, 2.3 Hz), 3.52 (d, 3H, J=10.8 Hz).

MS (ES-API$^+$) m/z=349.0 (M+H$^+$).

Example 17: 3-Carbamoyl-1-((2R,3R,4S,5R)-5-(((dimethoxyphosphoryl)oxy)methyl)-3,4-dihydroxytetrahydrofuran-2-yl)pyridin-1-ium Acetate salt (Compound 17)

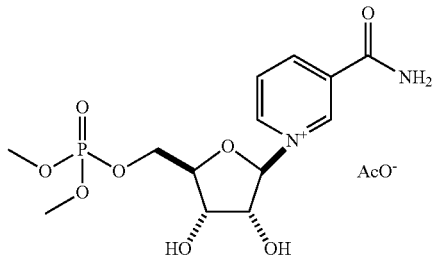

A 100 mL receiving flask was charged with 4.62 g (11 mmol) of 3-carbamoyl-1-((2R,3R,4S,5R)-3,4-dihydroxy-5-(hydroxymethyl)tetrahydrofuran-2-yl)pyridin-1-ium trifluoromethanesulfonate (nicotinamide riboside trifluoromethanesulfonate salt). To this was added 50 mL of anhydrous acetonitrile, then the mixture was stirred at ambient temperature for 15 min, and concentrated in vacuo to a light yellow foam. The foam was maintained under an argon atmosphere. To the foam was added 25 mL of trimethylphosphate, via syringe at ambient temperature. The mixture was stirred at ambient temperature for 5 min, then cooled with an ice bath. To this was added 4.2 mL (45.9 mmol) of $POCl_3$. The mixture was stirred with ice cooling for 3 h, then the solution of 3-carbamoyl-1-((2R,3R,4S,5R)-5-(((dichlorophosphoryl)oxy)methyl)-3,4-dihydroxytetrahydrofuran-2-yl)pyridin-1-ium chloride/trifluoromethanesulfonate was used in subsequent phosphate ester preparations. A 10 g quantity of this solution was added to 10 mL of ice-cold methanol. The solution was stirred with ice cooling for 45 min.

The product was purified by eluting over a 100 g Quadrasil AP column which had been conditioned according to the procedure described in J. Org. Chem. 2012, 77, 7319-7329, and subsequently placed in ethyl acetate. The reaction mixture was diluted with 90 mL of ethyl acetate and eluted onto the column. The column was then eluted with 250 mL of ethyl acetate, followed by 400 mL of 70:30 ethyl acetate: methanol, and collecting 20 mL fractions during the ethyl acetate: methanol elution. The product containing fractions were identified by LCMS. The product containing fractions were pooled and concentrated in vacuo to an oily residue. This was followed by 3 mL of water, followed by 3 mL of methanol to give the product as a hygroscopic amorphous solid, 133 mg (8%).

$^1$H NMR (500 MHz, $D_2O$) δ 9.38 (m, 1H), 9.15 (m, 1H), 8.95 (dt, 1H, J=8.1, 1.5 Hz), 8.26 (dd, 1H, J=8.1, 6.3 Hz), 6.23 (d, 1H, J=4.6 Hz), 4.62 (dt, 1H, J=6.5, 3.2 Hz), 4.55 (ddd, 1H, J=12.0, 4.9, 2.5 Hz), 4.44 (t, 1H, J=4.8 Hz), 4.40 (ddd, 1H, J=12.0, 5.6, 3.1 Hz), 4.36 (dd, 1H, J=5.0, 4.1 Hz), 3.77 (d, 3H, J=5.3 Hz), 3.75 (d, 3H, J=5.3 Hz), 1.87 (s, 3H).

MS (ES-API$^+$) m/z=363.0 (M$^+$).

Example 18: 3-Carbamoyl-1-((2R,3R,4S,5R)-5-(((diisopropoxyphosphoryl)oxy)methyl)-3,4-dihydroxytetrahydrofuran-2-yl)pyridin-1-ium Acetate salt (Compound 18)

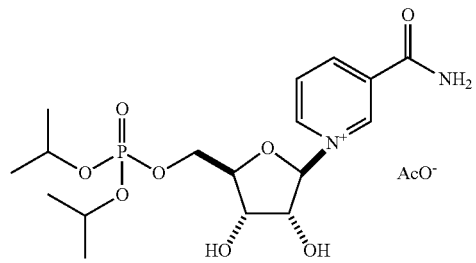

A 100 mL receiving flask was charged with 4.62 g (11 mmol) of 3-carbamoyl-1-((2R,3R,4S,5R)-3,4-dihydroxy-5-(hydroxymethyl)tetrahydrofuran-2-yl)pyridin-1-ium trifluoromethanesulfonate (nicotinamide riboside trifluoromethanesulfonate salt). To this was added 50 mL of anhydrous acetonitrile, then the mixture was stirred at ambient temperature for 15 min, and concentrated in vacuo to a light yellow foam. The foam was maintained under an argon atmosphere. To the foam was added 25 mL of trimethylphosphate via syringe at ambient temperature. The mixture was stirred at ambient temperature for 5 min, then cooled with an ice bath. To this was added 4.2 mL (45.9 mmol) of POCl$_3$. The mixture was stirred with ice cooling for 3 h, then the solution of 3-carbamoyl-1-((2R,3R,4S,5R)-5-(((dichlorophosphoryl)oxy)methyl)-3,4-dihydroxytetrahydrofuran-2-yl)pyridin-1-ium chloride/trifluoromethanesulfonate was used in subsequent phosphate ester preparations. An aliquot of this solution containing approximately 1.15 g of the dichlorophosphoryl intermediate was diluted with 7 mL of isopropanol, then the mixture was stirred at ambient temperature for two days.

The product was purified by eluting over a 100 g Quadrasil AP column using a sequence similar to that used to purify 3-carbamoyl-1-((2R,3R,4S,5R)-5-(((dimethoxyphosphoryl)oxy)methyl)-3,4-dihydroxytetrahydrofuran-2-yl) pyridin-1-ium acetate. After concentration of the product containing fractions, the residue was chased 2×5 mL water, avoiding concentrating to dryness and concentrating to about 2 mL residual volume each time. The residual solution was diluted with 5 mL of water, filtered through a 0.45 micron filter, then the filter was washed 2×3 mL water. The combined filtrate and washings were frozen and lyophilized to give 413 mg (28%) of an amorphous solid. $^1$H NMR (500 MHz, D$_2$O) δ 9.38 (m, 1H), 9.16 (m, 1H), 8.97 (dt, 1H, J=8.1, 1.5 Hz), 8.27 (m, 1H), 6.23 (d, 1H, J=4.7 Hz), 4.63 (m, 3H), 4.49 (ddd, 1H, J=12.0, 4.7, 2.5 Hz), 4.42 (t, 1H, J=4.9 Hz), 4.34 (m, 2H), 1.89 (s, 3H), 1.27 (m, 9H), 1.23 (d, 3H, J=6.2 Hz). MS (ES-API$^+$) m/z=419.0 (M$^+$).

Example 19: 3-Carbamoyl-1-(5-(((diethoxyphosphoryl)oxy)methyl)-3,4-dihydroxytetrahydro furan-2-yl) pyridin-1-ium Chloride (Compound 19)

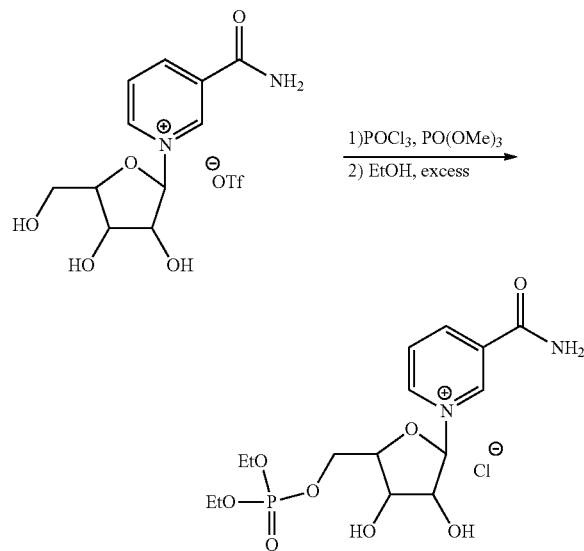

Nicotinamide Riboside Triflate salt (1.3 g, 3.22 mmoles) was placed into a 10 ml single necked round bottomed flask under N$_2$. Freshly distilled trimethyl phosphate (2.6 ml) was added via syringe and this was stirred until a solution formed (15 min). This solution was placed under vacuum for 15 minutes to remove volatiles then placed under N$_2$. The solution was cooled in an ice-water bath for 10 minutes then phosphorous oxychloride (1.30 ml, 2.14 g, 13.8 mmols, 4.3 equivalents) was added dropwise over 10 minutes. The reaction was stirred at 0° C. for 1 hour, placed into a 4° C. refrigerator and allowed to react overnight. The reaction was checked by HPLC for completeness and then placed into an ice-water bath and ethanol (5.0 ml, 3.95 gm, 85.6 mmoles, 26.6 equivalents) was added dropwise over 6 minutes. The reaction was removed from the cold bath and it was allowed to warm to room temperature for 4 hours. At this time, the reaction was added dropwise to a well stirred solution of diethyl ether (100 ml). The stirring was stopped and the upper layer decanted off. The heavy oil was dissolved in a minimum of ethanol and added dropwise to well-stirred diethyl ether. The stirring was stopped and the ether layer decanted. The resulting heavy oil was placed under vacuum and the resulting foam was purified using a silica gel preparative chromatography plate using 7:3:0.5 DCM:MeOH:formic acid. This gave 0.760 g of a clear oil, which still contained a small amount of trimethyl phosphate, but which was identified as diethyl NMN by HPLC/MS, $^1$H and $^{31}$P NMR.

$^1$HNMR (D$_2$O) δ 9.31 (bs, 1H), 9.08 (m, 1H), 8.88 (1H, d), 8.21 (m, 2H), 6.15 (1H, d), 4.55-4.45 (2H, m), 4.34-4.25 (3H, m), 4.04 (4H, m), 1.22-1.13 (6H, m)

$^{31}$P NMR (D$_2$O) δ -2.21

MS(ESI+) m/z=391(M+)

Example 20: 3-Carbamoyl-1-(5-(((dibutoxyphosphoryl)oxy)methyl)-3,4-dihydroxytetrahydro furan-2-yl)pyridin-1-ium Chloride (Compound 20)

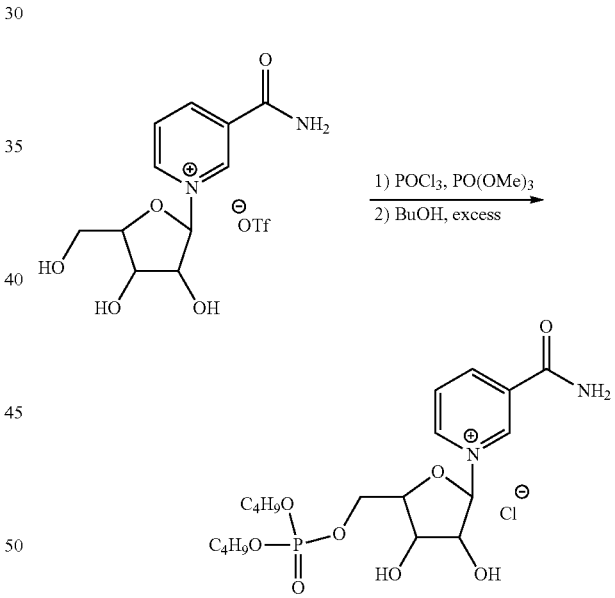

Nicotinamide riboside triflate salt (1.57 g, 3.90 mmols) was placed into a 10 ml single necked round bottomed flask and co evaporated with dry ACN (2 ml). Freshly distilled trimethyl phosphate (2.0 ml) was added via syringe and this was stirred until homogeneous (approximately 30 minutes). The solution was degassed for 5 minutes then placed under N$_2$. It was cooled in an ice water bath for 10 minutes then phosphorous oxychloride (0.73 ml, 1.20 g, 7.8 mmols, 2 equiv.) was added dropwise via syringe over 5 minutes. The reaction was kept in the cold bath for 30 minutes then placed in a 4° C. refrigerator overnight. The reaction was monitored by an H$_2$O quench followed by HPLC, once complete, the reaction was placed into an ice water bath and n-BuOH (2 ml, 1.62 g, 21.9 mmoles, 5.6 equiv.) was added dropwise via syringe. It was stirred for 30 minutes then placed into the refrigerator for 2 days. At this time HPLC analysis showed approximately 60% of the diester had formed so diethyl ether was added and the resulting clear heavy oil was placed under vacuum. Isolation of the product was accomplished by preparative silica gel separation using a 7:3:0.5 DCM:MeOH:formic acid system.

$^1$H NMR (D$_2$O) δ ppm 9.37 (1H, bs), 9.13 (1H, d), 8.95 (1H, d), 8.23 (1H, m), 6.18 (1H, d), 4.56-4.28 (5H, m), 3.99 (4H, q), 1.51 (4H, q), 1.31-1.18 (4H, m), 0.78 (6H, t).

$^{31}$P (D$_2$O) δ -0.27.

MS(ESI+) m/z=447.10 (M+)

Example 21: 3-Carbamoyl-1-(3,4-dihydroxy-5-(((methoxy(3-(pentadecyloxy)propoxy) phosphoryl) oxy)methyl)tetrahydrofuran-2-yl)pyridin-1-ium Trifluoroacetate salt (Compound 21)

Example 21A: 3-(pentadecyloxy)propan-1-ol

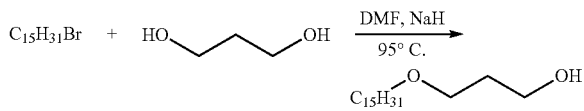

Reference Bioorg & Med Chem. 20(2012), 3658, Yamano et al

This intermediate was prepared according to Yamano et al., Bioorg & Med. Chem. 20, 3658 2012.

$^1$H NMR (CDCl$_3$) δ ppm 3.77 (2H, t), 3.61 (2H, t), 3.42 (2H, t), 1.83 (2H, t), 1.562H, m), 1.31-1.25 (24H, m), 0.88 (3H, t).

Example 21B: 3-(nonyloxy)propan-1-ol

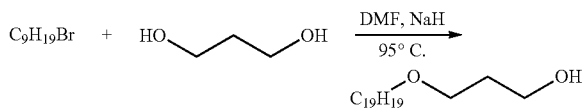

Reference Bioorg & Med Chem. 20(2012), 3658, Yamano et al

This intermediate was prepared according to Yamano et al., Bioorg & Med. Chem. 20, 3658 2012.

$^1$HNMR (CDCl$_3$) δ 3.78 (2H, t), 3.61 (2H, t), 3.43 (2H, t), 1.83 (2H, dt), 1.57 (2H, dd), 1.33-1.25 (12H, m), 0.88 (3H, t).

Example 21C: Methyl (4-nitrophenyl)(3-(pentadecyloxy)propyl) phosphate

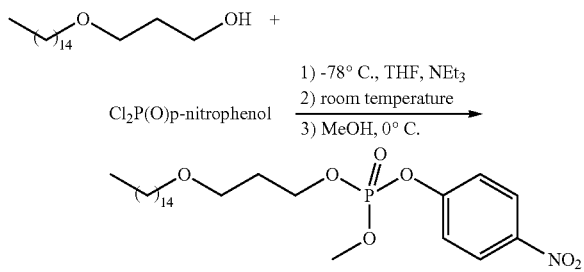

Dichloro-4-nitrophenylphosphate (1.0 g, 3.91 mmols) was placed into a dry 25 ml single necked round bottomed flask equipped with a septum under N$_2$. Dry THF (6 ml) was added via syringe. This solution was stirred and cooled to -78° C. Triethylamine (1.64 ml, 1.19 g, 11.7 mmols) was added dropwise to the stirred reaction mixture, giving a yellow color to the reaction. The C-15 ether (1.12 g, 3.91 mmoles), dissolved in dry THF (3 ml), was added dropwise to the reaction mixture over 5 minutes. The cold bath was then removed and the reaction allowed to slowly warm to room temperature. A thick precipitate of triethylamine hydrochloride formed. After 40 minutes at room temperature, the reaction was cooled with an ice bath, and dry methanol (0.158 ml, 0.125 g, 3.91 mmols) was added dropwise over 2 minutes. The cold bath was then removed and the reaction allowed to warm to room temperature for 1 hour. The reaction was then concentrated in vacuo, dissolved in ethyl acetate, filtered, re-concentrated, dissolved in hexanes, re-filtered and concentrated in vacuo to give a thick oil, 1.95 g. This was dissolved in a minimum of dichloromethane and purified using 20 g silica gel, eluting with 5:1 dichloromethane:ethyl acetate. This gave 1.54 g of the title intermediate (78.6% yield).

$^1$H NMR (CDCl$_3$) δ ppm 8.24-8.21 (2H, m), 7.38-7.35 (2H, m), 4.30-4.26 (2H, m), 3.90-3.86 (3H, m), 3.47 (2H, t), 3.36 (2H, t), 1.95 (2H, td), 1.51 (2H, t), 1.27-1.23 (24H, m), 0.85 (3H, t).

$^{31}$P NMR (CDCl$_3$) δ -5.38

Example 21D: Methyl (4-nitrophenyl)(3-(nonyloxy)propyl) phosphate

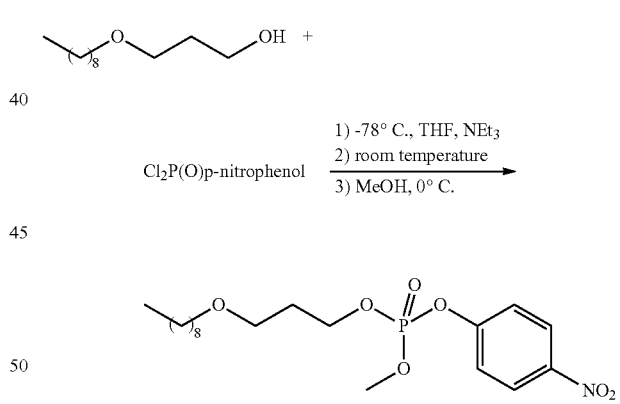

The title intermediate was prepared using the Example 23C procedure utilizing 6.33 g (24.7 mmols) of the dicholoro 4-nitrophenylphosphate, 7.94 ml (5.75 g, 56.8 mmols) of triethylamine, 5.00 g (24.7 mmols) of 3-(nonyloxy)propan-1-ol and 1.00 ml (0.79 g, 24.7 mmols) of anhydrous methanol. After purification using 70 g of silica gel and 2:1 hexanes:ethyl acetate as eluent, 5.00 g of the title intermediate was obtained (48.5%).

$^1$H NMR (CDCl$_3$) δ ppm 8.27-8.25 (2H, m), 7.41-7.39 (2H, m), 4.33-4.29 (2H, m), 3.91 (3H, dd), 3.50 (2H, t), 3.39 (2H, m), 2.00-1.97 (2H, m), 1.55 (2H, t), 1.33-1.27 (12H, m), 0.89 (3H, t).

MS(ES-API) m/z=418(M+H+)

Example 21E: (6-(3-Carbamoylpyridin-1(4H)-yl)-2,2-dimethyltetrahydrofuro[3,4-d][1,3]dioxol-4-yl) methyl methyl (3-(pentadecyloxy)propyl) phosphate

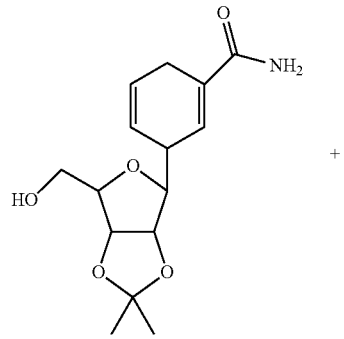

Example 21F: 6-(3-Carbamoylpyridin-1(4H)-yl)-2,2-dimethyltetrahydrofuro[3,4-d][1,3]dioxol-4-yl) methyl methyl (3-(nonyloxy)propyl) phosphate

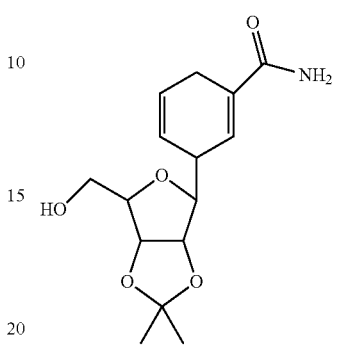

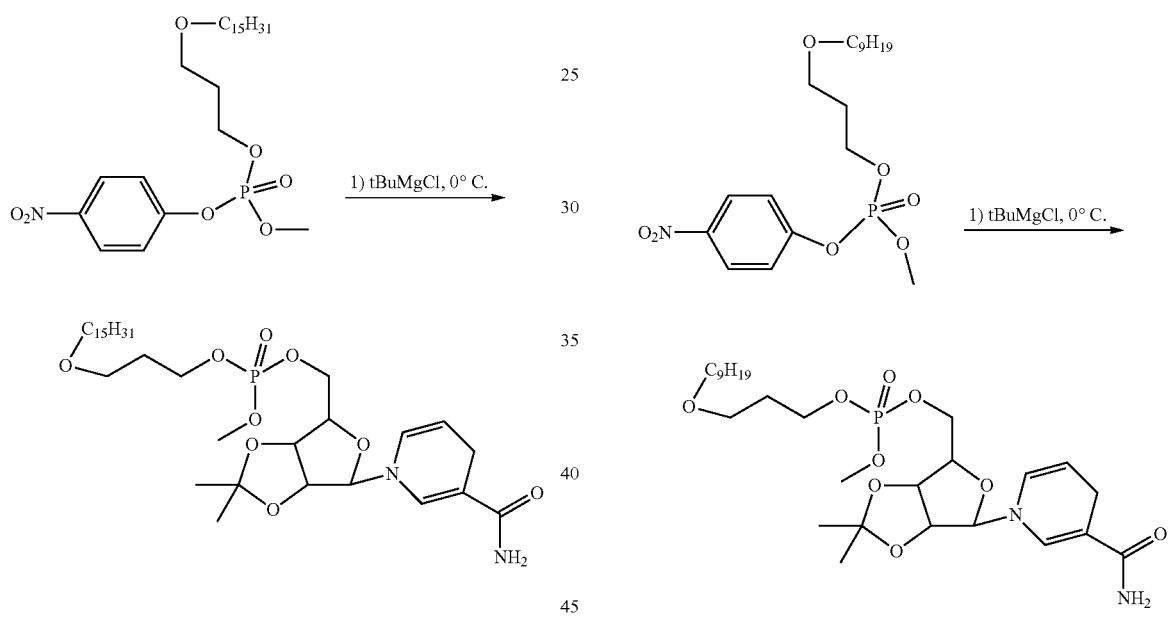

The title intermediate was prepared according to the procedure of Example 6B. Using 1-(6-(hydroxymethyl)-2,2-dimethyltetrahydrofuro[3,4-d][1,3]dioxol-4-yl)-1,4-dihydropyridine-3-carboxamide (0.759 g, 2.53 mmols), 2.93 ml of 1M t-Butyl magnesium chloride in THF and 1.33 g (2.66 mmols) of methyl (4-nitrophenyl) (3-(pentadecyloxy)propyl) phosphate, the desired crude product was obtained (2.2 g). This was purified using 20 g of silica gel and a stepwise gradient of 0-10% methanol in dichloromethane as eluent. This gave 699 mg of product (40% yield).

$^1$H NMR (CDCl$_3$) δ ppm 7.05 (1H, s), 5.88-5.86 (1H, m), 5.61-5.58 (1H, m), 4.84-4.78 (1H, m), 4.68 (1H, ddd), 4.61-4.58 (1H, m), 4.22-4.08 (4H, m), 3.78-3.73 (3H, m), 3.48-3.35 (4H, m), 3.09-3.08 (1H, m), 1.93-1.89 (2H, m), 1.55-1.49 (5H, m), 1.34-1.19 (27H, m), 0.86 (3H, t).

$^{31}$P NMR(CDCl$_3$) δ −0.36.

MS(ES-API) m/z=659.3 (M+H+)

The title intermediate was prepared according to the procedure of Example 6B. Using 3.39 g (11.4 mmols) of 1-(6-(hydroxymethyl)-2,2-dimethyltetrahydrofuro[3,4-d][1,3]dioxol-4-yl)-1,4-dihydropyridine-3-carboxamide, 12.5 ml of 1M t-butyl magnesium chloride and 5.00 g (11.98 mmols) of methyl (4-nitrophenyl) (3-(nonyloxy)propyl) phosphate, the crude product was obtained (10.62 g). This was purified using 100 g of silica gel and a stepwise gradient of 0 to 10% methanol in dichloromethane resulting in the isolation of 2.35 g the product.

$^1$H NMR (CDCl$_3$) δ ppm 7.10 (1H, s), 5.914 (1H, d), 5.59-5.581H, m), 4.88-4.82 (2H, m), 4.73 (1H, m), 4.63 (1H, m), 4.26-4.12 (5H, m), 3.82-3.78 (3H, m), 3.52-3.49 (2H, m), 3.41 (2H, m), 1.98-1.93 (2H, m), 1.58-1.54 (5H, m), 1.39-1.28 (15H, m), 0.90 (3H, t).

MS (ES-API) m/z=575(M+H+)

Example 21 G: 3-Carbamoyl-1-(6-(((methoxy(3-(pentadecyloxy)propoxy)phosphoryl) oxy)methyl)-2,2-dimethyltetrahydrofuro[3,4-d][1,3]dioxol-4-yl) pyridin-1-ium acetate

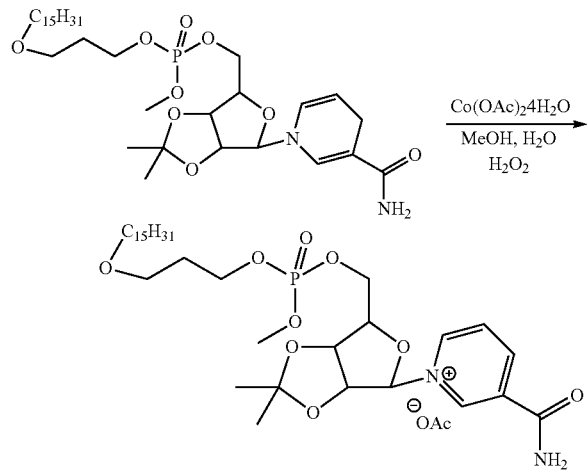

The title intermediate was prepared according to the procedure of Example 6C. Using 2.07 g (3.14 mmoles) of (6-(3-carbamoylpyridin-1(4H)-yl)-2,2-dimethyltetrahydrofuro[3,4-d][1,3]dioxol-4-yl)methyl methyl (3-(pentadecyloxy)propyl) phosphate, the starting material was oxidized and purified to give 1.18 g of product (52% yield).

$^1$H NMR (CDCl$_3$) δ ppm 9.86 (1H, d), 9.18-9.13 (2H, m), 8.19 (1H, s), 6.45-6.43 (1H, m), 6.24 (1H, d), 5.17-5.16 (1H, m), 4.91 (1H, d), 4.85 (1H, dt), 4.12 (2H, dd), 3.72 (3H, dd), 3.45 (2H, m), 3.38 (2H, m), 1.90 (3H, m), 1.65 (3H, bs), 1.55 (2H, m), 1.39 (3H, bs), 1.25 (24H, bs), 0.88 (3H, t).

MS(ES-API) m/z=657.5 (M+)

Example 21H: 3-Carbamoyl-1-(6-(((methoxy(3-(nonyloxy)propoxy)phosphoryl)oxy)methyl)-2,2-dimethyltetrahydrofuro[3,4-d][1,3]dioxol-4-yl)pyridin-1-ium acetate

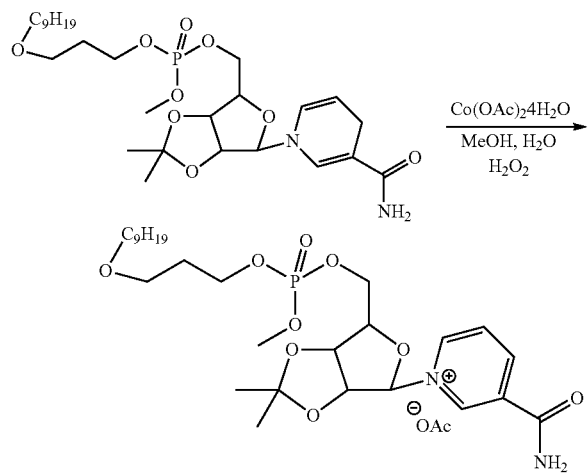

The title intermediate was prepared according to the procedure of Example 6C. Using 2.40 g, (4.17 mmoles) of 6-(3-carbamoylpyridin-1(4H)-yl)-2,2-dimethyltetrahydrofuro[3,4-d][1,3]dioxol-4-yl)methyl methyl (3-(nonyloxy)propyl) phosphate, the starting material was oxidized to give 2.05 g of a green foam (78% yield). The purity was assessed by HPLC to be sufficient to carry on to the final product, the MS confirmed its identity.

MS(ES_API) m/z=573(M+)

Example 21I: 3-carbamoyl-1-(3,4-dihydroxy-5-(((methoxy(3-(pentadecyloxy)propoxy) phosphoryl) oxy)methyl)tetrahydrofurantetrahydrofurantetrahydrofuran-2-yl)pyridin-1-ium Trifluoroacetate salt (Compound 21)

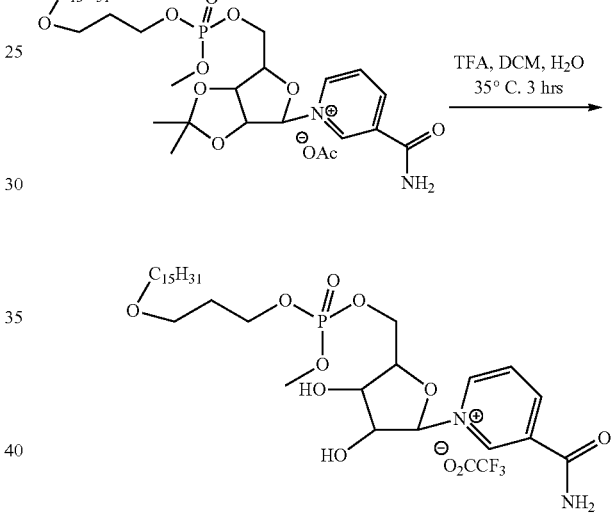

Compound 21 was prepared according to the procedure of Example 6D. 2.90 g (4.05 mmoles) of 3-carbamoyl-1-(6-(((methoxy(3-(pentadecyloxy)propoxy)phosphoryl)oxy) methyl)-2,2-dimethyltetrahydrofuro[3,4-d][1,3]dioxol-4-yl) pyridin-1-ium acetate was treated with triflic acid, dichloromethane and water (22:20:1.9 ml) at 35° C. for 2 hours. When the reaction was complete by HPLC, the reaction was concentrated in vacuo and co-evaporated with acetonitrile (2×15 ml), giving a dark green glass. This was dissolved in a minimum of dichloromethane and loaded onto a 50 g silica gel column and eluted with a step-wise gradient of 0 to 20% methanol in dichloromethane. Concentration of the product fractions gave 1.74 g (56% yield).

$^1$HNMR (CDCl$_3$) δ ppm 9.93 ((1H, bs), 9.42 (1H, bs), 9.09 (1H, bd), 9.00 (1H, bs), 8.16 (1H, m), 6.55 (1H, bs), 6.35 (bs), 4.64 (1H, bs), 4.48 (2H, bs), 4.37 (2H, bs), 4.23-4.14 (2H, m), 3.78 (3H, dd), 3.51 (2H, dt), 3.41 (2H, td), 1.95 (2H, td), 1.56 (2H, t), 1.32 (25H, m), 0.905 (3H, t).

$^{31}$P NMR (CDCl$_3$) δ 0.26 (bs).

MS(ES-API) m/z=617(M+)

Example 22: 3-Carbamoyl-1-(3,4-dihydroxy-5-(((methoxy(3-(nonyloxy)propoxy)phosphoryl) oxy)methyl)tetrahydrofuran-2-yl)pyridin-1-ium Trifluoroacetate salt (Compound 22)

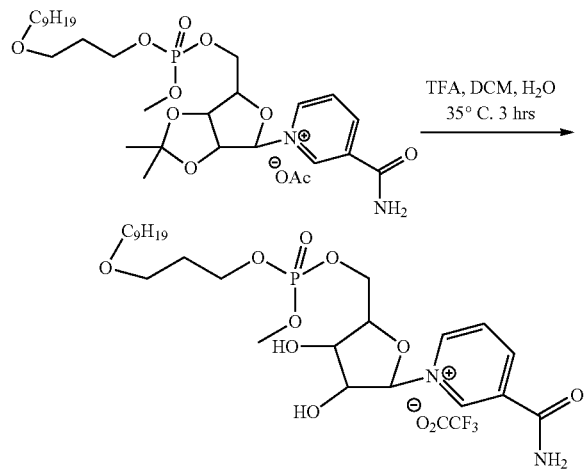

Compound 22 was prepared according to the procedure of Example 6D. 3-carbamoyl-1-(6-(((methoxy(3-(nonyloxy)propoxy)phosphoryl)oxy)methyl)-2,2-dimethyltetrahydrofuro[3,4-d][1,3]dioxol-4-yl)pyridin-1-ium acetate (2.05 g, 3.57 mmoles) was treated with trifluoroacetic acid, dichloromethane and water (14:15.5:1.34 ml) at 35° C. for 1.5 hours. The reaction was monitored by HPLC and when finished, it was concentrated in vacuo and co-evaporated 3 times with acetonitrile (15 ml each). This gave a dark green oil, 3.0 g. The oil was dissolved in a minimum of dichloromethane and purified on 30 g of silica gel utilizing a step-wise gradient of 0 to 20% methanol in dichloromethane. The product fractions were collected and concentrated to give 1.08 g of a brown glass, which was dissolved in 3 ml of water, frozen and lyophilized to give 1.00 g (41% yield) of a light brown foam.

$^1$H NMR (D$_2$O) δ ppm 9.39 (1H, bs), 9.17-9.15 (1H, m), 8.98 (1H, dd), 8.27 (1H, t), 6.24-6.23 (1H, m), 4.58-4.4.57 (1H, m), 4.51-4.46 (1H, m), 4.42-4.36 (2H, m), 4.32-4.29 (1H, m), 4.13 (2H, q), 3.74 (3H, dd), 3.49-3.45 (2H m), 3.39-3.30 (2H, m), 1.89 (2H, td), 1.48-1.47 (2H, m), 1.21 (12H, bs), 0.80 (3H, t).
$^{31}$P NMR (D$_2$O) δ 0.15 (d).
MS(ES-API) m/z=533(M+)

Example 23: Biological Assays for Determining Levels of NAD+

As the compounds disclosed herein can act as prodrugs for NMN, their biological activity was assessed in vivo by measuring the ability to elevate NAD+ levels in liver and skeletal muscle. These tissues were selected for pharmacodynamics studies due to their relevance for the treatment of metabolic diseases. In general, C57/BL6 mice were fasted from 16 hours, then administered a 500 mg/ml oral dose of a disclosed compound in PBS buffer by oral gavage. In some cases, the dose was 250 mg/kg or in an alternate vehicle: ethanol/PBS/PEG400 (10/30/60). After dosing, the mice were sacrificed at pre-set time points after dosing (generally 4, 8 and 24 hours). The liver and skeletal tissues were removed and flash frozen. After some period of frozen storage, tissue homogenates were prepared. The level of NAD+ was quantified using LC/MS methods.

For bioanalysis, a method of standard addition was used to quantify the NAD. Each homogenate was divided and certain aliquots had known concentrations of exogenous NAD added. The NAD present in the original sample was then calculated by linear regression. Data are presented as a ratio of mean NAD concentration in treated mouse tissues to mean NAD concentration in the vehicle control group tissues at the paired time points.

Example 23A: Study Design for Assaying Levels of NAD+ in Mice

Mixtures of compound and PBS, pH 7 were formulated ~1 hour before dosing and remained stirring until dose completion. Residual formulated test materials were stored at −20±5° C. until discarded. Naïve male C57/BL6 mice at ~25 g at dose initiation, age as appropriate for weight were assigned to dose groups of six animals per dose. Dosing treatments were administered via a single oral gavage dose (PO) The dose volume for each animal (5 mL/kg) was based on the most recent body measurements taken the morning of dosing. Animals were fasted at least 16 hrs prior to dose, with food returned at least 4 hours post dose.

Liver and skeletal muscle were collected and analyzed for nicotinamide adenine dinucleotide (NAD) at 0, 4, 8, and 24 hours post-dose. For each mouse, the entire liver was removed, rinsed with saline, blotted dry and frozen at −70° C. to store for NAD concentration analysis. Also, the soleus skeletal muscle was removed from the gastrocnemius, rinsed with saline, blotted dry and frozen at −70° C. to store for NAD concentration analysis.

After thawing samples for analysis, the tissues were homogenized and extracted as follows:
Tissue Homogenization Procedure
1. Add 5× (tissue wt.*5) mL 0.1M ZnSO$_4$ into all tubes.
2. Add 5× (tissue wt*5) mL Methanol into all tubes.
3. Homogenize each sample until completely liquid.
4. Vortex each sample.
Tissue Extraction Procedure
1. On ice, aliquot 20 µL of standards, control blanks, and matrix blanks into a 96-well plate.
2. Aliquot 20 µL of sample into sample wells.
3. Add 100 µL of IS in 80:20 Methanol:water into each well, except blanks add 100 µL of blank 80:20 Methanol:Water.
4. Cover plate and vortex samples. Centrifuge for 10 minutes at 3300 rpm.
5. Transfer 80 µL of supernatant into a clean 96-well plate.
6. Add 80 µL of LC-MS water to all wells.
7. Cover and vortex.
The concentration of NAD+ in the tissues was determined by LC/MS. The conditions are as follows:
LC Conditions:
LC: Shimadzu UPLC
Autosampler: Shimadzu SIL-30AC
Analytical Column: Chromolith C18 RP-e 3.0×100 mm
Flow Rate: Variable flow 0.8 mL/min and 1.4 mL/min
Mobile Phases: A: dH$_2$O B: 1.0% Formic Acid in 50:50 MeOH:ACN
Needle Rinse: dH$_2$O
Injection Volume: 2.0 µL
LC Gradient Program: A 1.0 min gradient was utilitized going from 0% to 98% of Mobile
Phase B with a total run time of 3.00 minutes.

Mass Spectrometer Conditions:
Instrument: AB Sciex QTRAP 6500
Scan: Multiple Reaction Monitoring (MRM)
Resolution: Q1 Unit/Q3 Unit
Scan Parameters:

| Analyte | MRM Transition (m/z) | Ionization Mode |
|---|---|---|
| Alprazolam (IS) | 309.100/281.100 Da | ESI+ |
| NAD | 664.000/427.900 Da | ESI+ |

The ratio of mean NAD+ concentration in the liver and skeletal tissues of treated mice compared to vehicle control mice are given in Table 5. The data is given for the 4, 8, and 24 hour time points.

TABLE 5

| Compound | 4 hr liver | 8 hr liver | 24 hr liver | 4 hr skeletal | 8 hr skeletal | 24 hr skeletal |
|---|---|---|---|---|---|---|
| 1 (Assay 1) | 2.6 | 2.7 | 0.6 | 1.2 | 1.1 | 1.1 |
| 1 (Assay 2) | 1.6 | 1.6 | 0.9 | 1.4 | 0.6 | 0.5 |
| 1 (Assay 3) | 1.4 | 1.1 | 1.3 | 1.8 | 1.6 | 2.3 |
| 2 | 2.0 | 1.6 | 1.8 | 0.9 | 1.0 | 1.4 |
| 3 (Assay 1) | 1.6 | 1.6 | 0.8 | 0.6 | 1.4 | 1.6 |
| 3 (Assay 2) | 2.1 | 0.8 | 0.9 | 0.5 | 0.5 | 0.4 |
| 3 (Assay 3) | 1.6 | 1.5 | 1.4 | 1.3 | 1.0 | 0.4 |
| 4 | 1.0 | 1.7 | 1.8 | 0.9 | 1.4 | 1.1 |
| 6 | 4.3 | 6.6 | 3.5 | 1.3 | 1.7 | 2.6 |
| 7 (Assay 1) | 1.5 | 1.7 | 1.2 | 1.4 | 1.1 | 0.5 |
| 7 (Assay 2) | 1.1 | 1.1 | 1.1 | 1.3 | 1.2 | 1.4 |
| 8 | 1.2 | 1.0 | 0.9 | 1.0 | 0.8 | 0.8 |
| 9 | 0.8 | 0.8 | 1.3 | 1.88 | 1.34 | 0.96 |
| 19 | 1 | 1 | 1 | 0.8 | 1.2 | 0.1 |
| 21 | 2.2 | 2.1 | 1.7 | 1.3 | 2.4 | 3.4 |

The invention claimed is:

1. A method of treating a disease or disorder associated with NAD+ biosynthesis, comprising administering a compound, or a stereoisomer or salt thereof, to a subject in need thereof; wherein the compound has a structure represented by formula I:

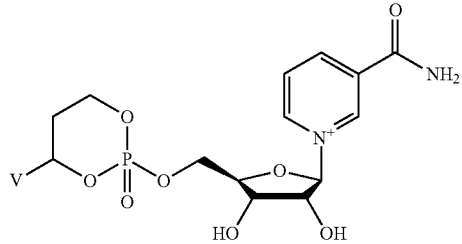

I wherein V is selected from hydrogen, phenyl and monocyclic heteroaryl, wherein (i) each said monocyclic heteroaryl contains five or six ring atoms of which 1 or 2 ring atoms are heteroatoms selected from N, S, and O, and the remainder of the ring atoms are carbon, and (ii) each said phenyl or monocyclic heteroaryl is unsubstituted or is substituted by one or two groups independently selected from halogen, trifluoromethyl, $C_1$-$C_6$ alkyl, $C_1$-$C_6$ alkoxy, and cyano; and wherein the disease or disorder is a mitochondrial disease or disorder.

2. The method of claim 1, wherein the compound js represented by formula I:

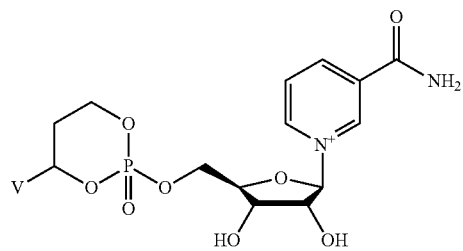

I wherein V is independently selected from the following substituents:

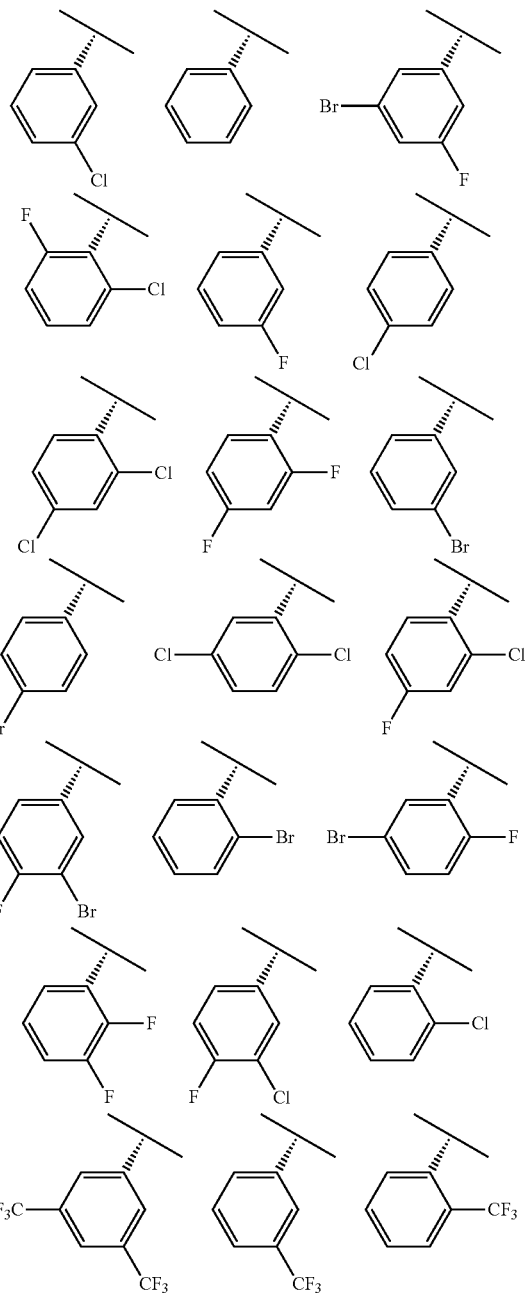

-continued

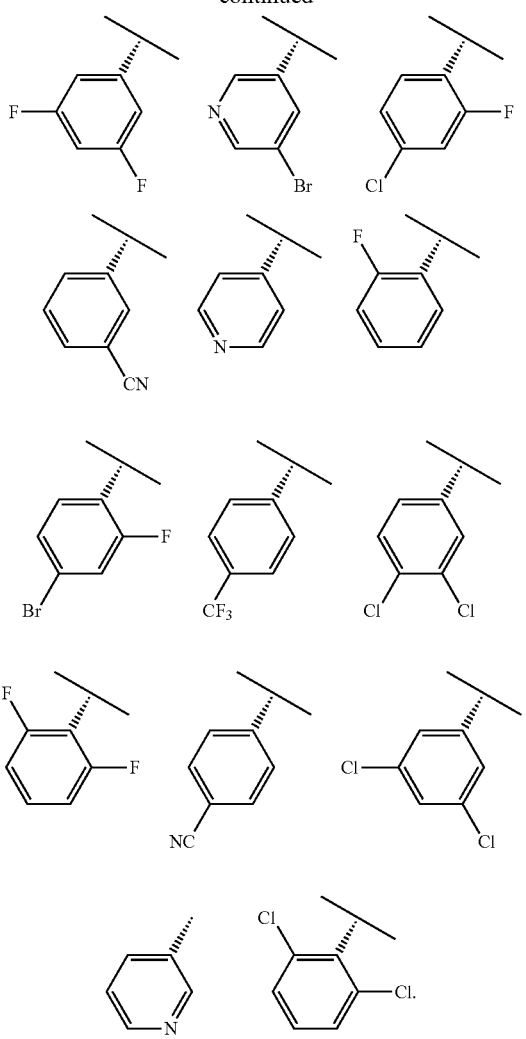

3. The method of claim 1, wherein the compound, or a stereoisomer or salt thereof, is selected from

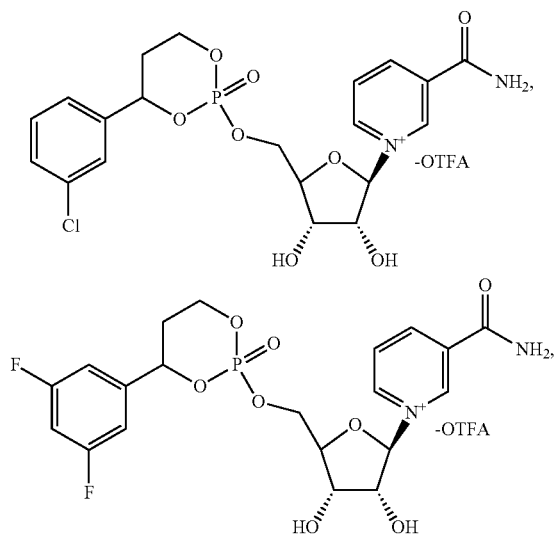

-continued

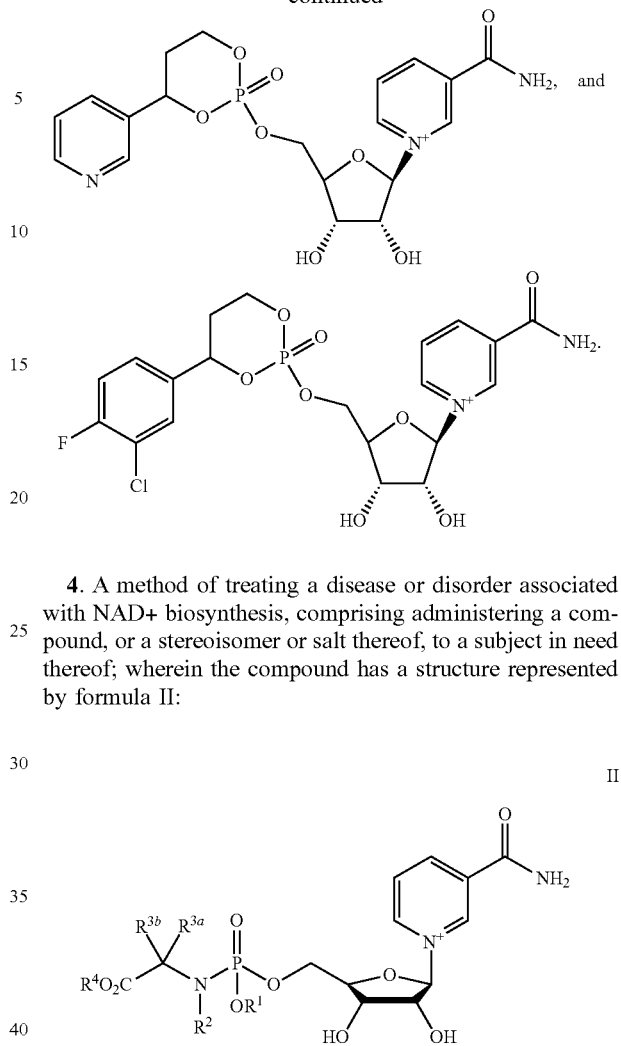

4. A method of treating a disease or disorder associated with NAD+ biosynthesis, comprising administering a compound, or a stereoisomer or salt thereof, to a subject in need thereof; wherein the compound has a structure represented by formula II:

II wherein
(a) each $R^1$ is independently hydrogen; n-alkyl; branched alkyl; cycloalkyl; or aryl, where aryl is optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —N(R$^1$)$_2$, $C_{1-6}$ acylamino, —NHSO$_2$C$_{1-6}$ alkyl, —SO$_2$N(R$^{1'}$)$_2$, COR$^{1''}$, and —SO$_2$C$_{1-6}$ alkyl;
each $R^{1'}$ is independently hydrogen or $C_{1-20}$alkyl, and $R^{1''}$ is —OR$^{1'}$ or —N(R$^{1'}$)$_2$;
(b) $R^2$ is hydrogen, $C_{1-10}$ alkyl or C(O)CR$^{3a}$R$^{3b}$NHR$^1$; or $R^2$ and either $R^{3a}$ or $R^{3b}$ together are (CH$_2$)$_n$, forming a ring that includes the intervening N and C atoms, where n is from 2 to 4;
(c) each $R^{3a}$ and $R^{3b}$ are
(i) independently selected from hydrogen, $C_{1-10}$ alkyl, cycloalkyl, —(CH$_2$)c(NR$^{3'}$)$_2$, $C_{1-6}$ hydroxyalkyl, —CH$_2$SH, —(CH$_2$)$_2$S(O)$_d$Me, —(CH$_2$)$_3$NHC(=NH)NH$_2$, (1H-indol-3-yl)methyl, (1H-imidazol-4-yl)methyl, —(CH$_2$)$_e$COR$^{3''}$, aryl and aryl $C_{1-3}$ alkyl, said aryl groups are optionally substituted with a group selected from hydroxyl, $C_{1-10}$ alkyl, $C_{1-6}$ alkoxy, halogen, nitro and cyano; or
(ii) $R^{3a}$ and $R^{3b}$ both are $C_{1-6}$ alkyl; or
(iii) $R^{3a}$ and $R^{3b}$ together are (CH$_2$)$_f$ so as to form a spiro ring; or (iv) $R^{3a}$ is hydrogen and $R^{3b}$ and $R^2$ together are $(CH_2)_n$ forming a ring that includes the adjoining N and C atoms; or (v) $R^{3b}$ is hydrogen and $R^{3a}$ and $R^2$ together are $(CH_2)_n$ forming a ring that includes the adjoining N and C atoms; or (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or $C_{3-7}$ cycloalkyl; or (vii) $R^{3a}$ is $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or $C_{3-7}$ cycloalkyl and $R^{3b}$ is H;

c is from 1 to 6, d is from 0 to 2, e is from 0 to 3, f is from 2 to 5, n is from 2 to 4, and (d) $R^4$ is hydrogen; $C_{1-10}$ alkyl optionally substituted with alkoxy, di($C_{1-6}$ alkyl)-amino, or halogen; $C_{1-10}$ haloalkyl; $C_{3-10}$ cycloalkyl; cycloalkyl alkyl; cycloheteroalkyl; aminoacyl; aryl; heteroaryl; substituted aryl; or substituted heteroaryl; and wherein the disease or disorder is a mitochondrial disease or disorder.

5. The method of treatment of claim 4, wherein the compound, or a stereoisomer or salt thereof, is selected from

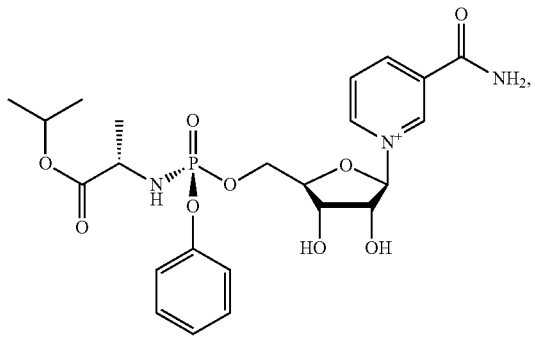

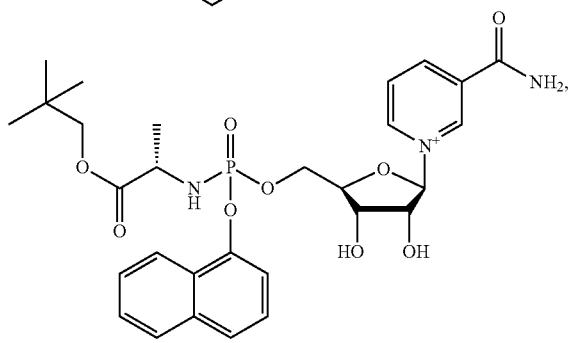

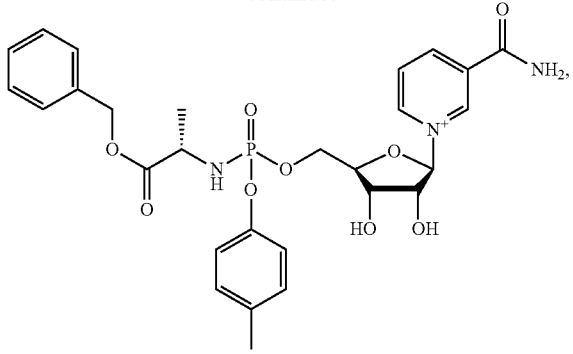

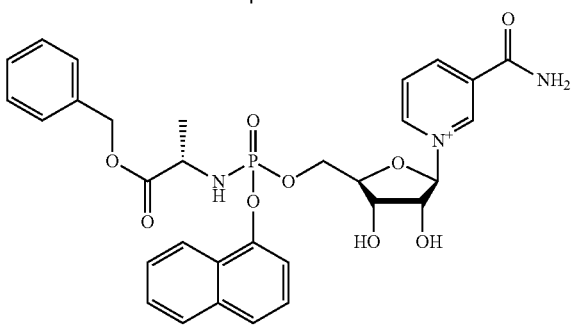

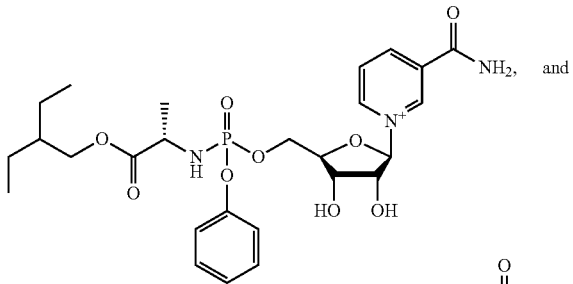

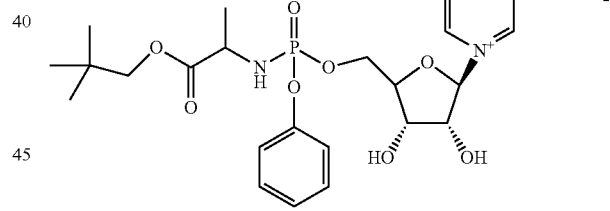

6. A method of treating a disease or disorder associated with NAD+ biosynthesis, comprising administering a compound, or a stereoisomer or salt thereof, to a subject in need thereof; wherein the compound has a structure represented by formula III:

III

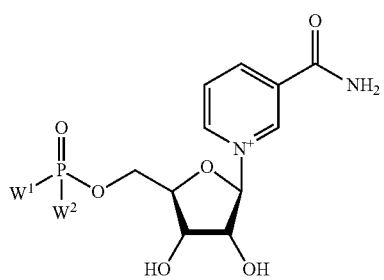

wherein each $W^1$ and $W^2$ is independently

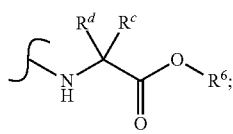

(i) each $R^c$ and $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl; or (ii) each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl; or (iii) each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S; or (iv) each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R; or (v) each $R^c$ is H and each $R^d$ is independently $(C_1-C_8)$alkyl; or (vi) each $R^c$ is H and each $R^d$ is independently $(C_1-C_8)$alkyl wherein the chirality of the carbon to which said $R^c$ and $R^d$ is attached is S; or (vii) each $R^c$ is H and each $R^d$ is independently $(C_1-C_8)$alkyl wherein the chirality of the carbon to which said $R^c$ and $R^d$ is attached is R; and each $R^6$ is independently $(C_1-C_8)$alkyl, $(C_2-C_8)$alkenyl, $(C_2-C_8)$alkynyl, $(C_3-C_8)$carbocyclyl or $(C_4-C_8)$carbocyclylalkyl; and wherein the disease or disorder is a mitochondrial disease or disorder.

7. A method of treating a disease or disorder associated with NAD+ biosynthesis, comprising administering a compound, or a stereoisomer or salt thereof, to a subject in need thereof; wherein the compound is represented by formula III:

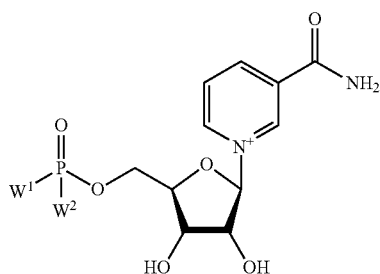

wherein $W^1$ and $W^2$ are independently selected from the substituents in Table 1, wherein
each $R^{21}$ is independently H or $(C_1-C_8)$alkyl;
each $R^{22}$ is independently H, $R^{21}$, $R^{23}$ or $R^{24}$, wherein each $R^{24}$ is independently substituted with 0 to 3 $R^{23}$;
each $R^{23}$ is independently $R^{23a}$, $R^{23b}$, $R^{23c}$ or $R^{23d}$, provided that when $R^{23}$ is bound to a heteroatom, then $R^{23}$ is $R^{23d}$ or $R^{23d}$;
each $R^{23a}$ is independently F, Cl, Br, I, —CN, —$N_3$ or —$NO_2$;
each $R^{23b}$ is independently $Y^{21}$;
each $R^{23c}$ is independently —$R^{2x}$, —$OR^{2x}$, —$N(R^{2x})(R^{2x})$, —$SR^{2x}$, —$S(O)R^{2x}$; —$S(O)_2R^{2x}$, —$S(O)(OR^{2x})$, —$S(O)_2(OR^{2x})$, —$OC(=Y^{21})R^{2x}$, —$OC(=Y^{21})OR^{2x}$, —$OC(=Y^{21})(N(R^{2x})(R^{2x}))$; —$SC(=Y^{21})R^{2x}$; —$SC(=Y^{21})OR^{2x}$, —$SC(=Y^{21})(N(R^{2x})(R^{2x}))$, —$N(R^{2x})C(=Y^{21})R^{2x}$, —$N(R^{2x})C(=Y^{21})OR^{2x}$, or —$N(R^{2x})C(=Y^{21})(N(R^{2x})(R^{2x}))$;
each $R^{23d}$ is independently —$C(=Y^{21})R^{2x}$; —$C(=Y^{21})OR^{2x}$ or —$C(=Y^{21})(N(R^{2x})(R^{2x}))$;
each $R^{2x}$ is independently H, $(C_1-C_8)$alkyl, $(C_2-C_8)$alkenyl, $(C_2-C_8)$alkynyl, aryl, heteroaryl; or two $R^{2x}$ taken together with a nitrogen or oxygen to which they are both attached form a 3 to 7 membered heterocyclic ring wherein any one carbon atom of said heterocyclic ring can optionally be replaced with —O—, —S— or —$NR^{21}$—; and wherein one or more of the non-terminal carbon atoms of each said $(C_1-C_8)$alkyl may be optionally replaced with —O—, —S— or —$NR^{21}$—;
each $R^{24}$ is independently $(C_1-C_8)$alkyl, $(C_2-C_8)$alkenyl, or $(C_2-C_8)$alkynyl;
each $R^{25}$ is independently $R^{24}$, wherein each $R^{24}$ is substituted with 0 to 3 $R^{23}$ groups;
each $R^{25a}$ is independently $(C_1-C_8)$alkylene, $(C_2-C_8)$alkenylene, or $(C_2-C_8)$alkynylene, any one of which said $(C_1-C_8)$alkylene, $(C_2-C_8)$alkenylene, or $(C_2-C_8)$alkynylene is substituted with 0-3 $R^{23}$ groups;
each $W^{23}$ is independently $W^{24}$ or $W^{25}$;
each $W^{24}$ is independently $R^{25}$, —$C(=Y^{21})R^{25}$, —$C(=Y^{21})W^{25}$, —$SO_2R^{25}$, or —$SO_2W^{25}$;
each $W^{25}$ is independently carbocycle or heterocycle wherein $W^{25}$ is independently substituted with 0 to 3 $R^{22}$ groups; and
each $Y^{21}$ is independently O or S; and
wherein the disease or disorder is a mitochondrial disease or disorder.

8. The method of claim 1, wherein treatment of the mitochondrial disease or disorder comprises increasing mitochondrial metabolism or increasing the activity level of SIRT3.

9. The method of claim 8, wherein increasing the activity level of SIRT3 has one or more effects selected from mimicking calorie restriction or exercise, increasing mitochodrial biogenesis, sensitizing a cell to glucose uptake, increasing fatty acid oxidation, decreasing reactive oxygen species, and promoting cell survival during genotoxic stress.

10. The method of claim 9, wherein increasing the activity level of SIRT3 increases metabolic activation of muscles selected from smooth muscles, gut and digestive muscles, skeletal muscles, and cardiac muscles; and/or treats cachexia and muscle wasting.

11. The method of claim 8, wherein the mitochondrial disease is selected from chronic progressive external ophthalmoplegia, myoclonus epilepsy associated with ragged-red fibers, Fukuhara syndrome, Leber's disease, Leigh encephalopathia and Pearson's disease.

12. The method of claim 4, wherein $R^1$ is optionally substituted phenyl or naphthyl.

13. The method of claim 4, wherein $R^{1'}$ is $C_{1-10}$ alkyl.

14. The method of claim 6, wherein

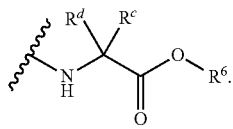

represents an ester of a naturally occurring α-amino acid.

15. The method of claim 6, wherein each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl.

16. The method of claim 6, wherein each $R^c$ is H and each $R^d$ is independently $(C_1-C_8)$alkyl.

17. The method of claim 6, wherein each $R^6$ is independently $(C_1-C_8)$alkyl.

18. A method of treating a disease or disorder associated with NAD+ biosynthesis, comprising administering a compound, or a stereoisomer or salt thereof, to a subject in need thereof; wherein the compound is represented by formula III:

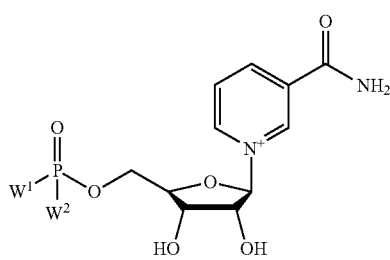

wherein one of $W^1$ and $W^2$ is $OR^5$, wherein
$R^5$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl; and
the other of $W^1$ and $W^2$ is

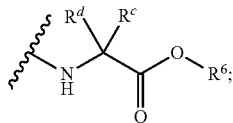

(i) each $R^c$ and $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl; or (ii) each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl; or (iii) each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S; or (iv) each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R; or (v) each $R^c$ is H and each $R^d$ is independently $(C_1-C_8)$alkyl; or (vi) each $R^c$ is H and each $R^d$ is independently $(C_1-C_8)$alkyl wherein the chirality of the carbon to which said $R^c$ and $R^d$ is attached is S; or (vii) each $R^c$ is H and each $R^d$ is independently $(C_1-C_8)$alkyl wherein the chirality of the carbon to which said $R^c$ and $R^d$ is attached is R; and each $R^6$ is independently $(C_1-C_8)$alkyl, $(C_2-C_8)$alkenyl, $(C_2-C_8)$alkynyl, $(C_3-C_8)$carbocyclyl or $(C_4-C_8)$carbocyclylalkyl; and wherein the disease or disorder is a mitochondrial disease or disorder.

19. The method of claim 18, wherein $R^5$ is $(C_6-C_{20})$aryl, $(C_2-C_{20})$heterocyclyl or heteroaryl.

20. The method of claim 18, wherein $R^5$ is unsubstituted phenyl.

21. The method of claim 18, wherein $R^5$ is pyridyl.

22. The method of claim 18, wherein one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl.

23. The method of claim 18, wherein one of $R^c$ or $R^d$ is H and the other of $R^c$ or $R^d$ is $(C_1-C_8)$alkyl.

24. The method of claim 18, wherein $R^5$ is unsubstituted phenyl, one of $R^c$ or $R^d$ is H and the other of $R^c$ or $R^d$ is methyl.

25. The method of claim 18, wherein $R^6$ is $(C_1-C_8)$alkyl.

26. The method of claim 18, wherein $R^5$ is unsubstituted phenyl and $R^6$ is $(C_1-C_8)$alkyl, $(C_2-C_8)$alkenyl, $(C_2-C_8)$alkynyl, $(C_3-C_8)$carbocyclyl, or $(C_4-C_8)$carbocyclylalkyl.

27. The method of claim 7, wherein the compound, or a stereoisomer or salt thereof, is selected from

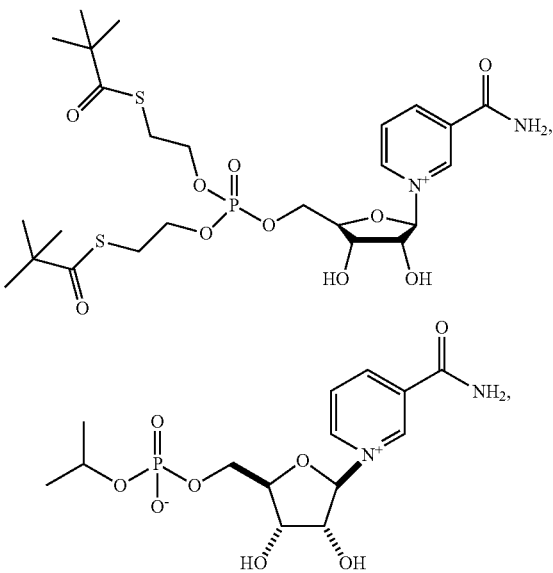

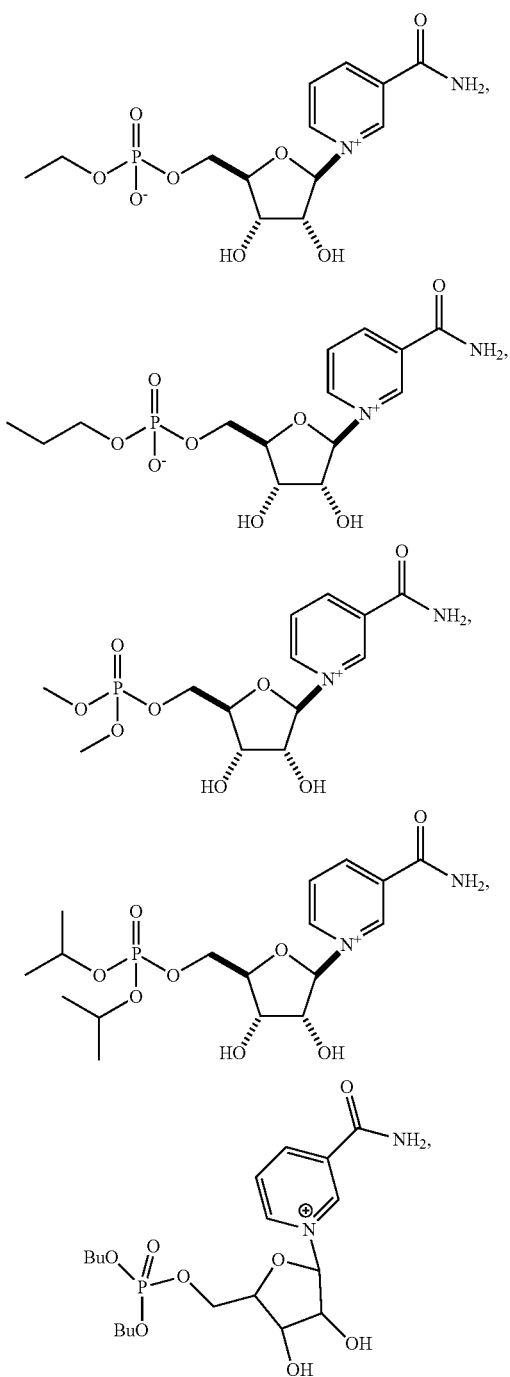

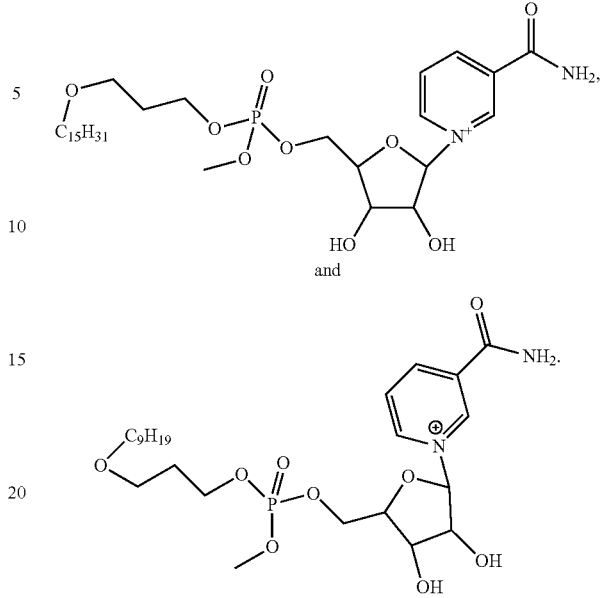

28. The method of claim 1, wherein the salt is formed with an anion selected from acetate, triflate, halide, trifluoroacetate, and formate.

29. The method of claim 4, wherein the salt is formed with an anion selected from acetate, triflate, halide, trifluoroacetate, and formate.

30. The method of claim 6, wherein the salt is formed with an anion selected from acetate, triflate, halide, trifluoroacetate, and formate.

31. The method of claim 7, wherein the salt is formed with an anion selected from acetate, triflate, halide, trifluoroacetate, and formate.

32. The method of claim 18, wherein the salt is formed with an anion selected from acetate, triflate, halide, trifluoroacetate, and formate.

33. The method of claim 1, wherein the salt is formed with an anion selected from $OH^-$, $H_2PO_4^-$, $HPO_4^{2-}$, $HSO_4^-$, $SO_4^{2-}$, $NO_3^-$, $HCO_3^-$, and $CO_3^{2-}$.

34. The method of claim 4, wherein the salt is formed with an anion selected from $OH^-$, $H_2PO_4^-$, $HPO_4^{2-}$, $HSO_4^-$, $SO_4^{2-}$, $NO_3^-$, $HCO_3^-$, and $CO_3^{2-}$.

35. The method of claim 6, wherein the salt is formed with an anion selected from $OH^-$, $H_2PO_4^-$, $HPO_4^{2-}$, $HSO_4^-$, $SO_4^{2-}$, $NO_3^-$, $HCO_3^-$, and $CO_3^{2-}$.

36. The method of claim 7, wherein the salt is formed with an anion selected from $OH^-$, $H_2PO_4^-$, $HPO_4^{2-}$, $HSO_4^-$, $SO_4^{2-}$, $NO_3^-$, $HCO_3^-$, and $CO_3^{2-}$.

37. The method of claim 18, wherein the salt is formed with an anion selected from $OH^-$, $H_2PO_4^-$, $HPO_4^{2-}$, $HSO_4^-$, $SO_4^{2-}$, $NO_3^-$, $HCO_3^-$, and $CO_3^{2-}$.

* * * * *

UNITED STATES PATENT AND TRADEMARK OFFICE
CERTIFICATE OF CORRECTION

PATENT NO. : 9,919,003 B2
APPLICATION NO. : 15/463683
DATED : March 20, 2018
INVENTOR(S) : Karl D. Normington et al.

Page 1 of 1

It is certified that error appears in the above-identified patent and that said Letters Patent is hereby corrected as shown below:

In the Claims

At Column 149, Line 66, please replace:
"js"
With:
--is--

Signed and Sealed this
Nineteenth Day of June, 2018

Andrei Iancu
*Director of the United States Patent and Trademark Office*